United States Patent
Fuchigami et al.

(10) Patent No.: US 12,152,045 B2
(45) Date of Patent: Nov. 26, 2024

(54) SILANE COUPLING COMPOUNDS AND MEDICAL AND/OR DENTAL CURABLE COMPOSITIONS COMPRISING THE SAME

(71) Applicant: KABUSHIKI KAISHA SHOFU, Kyoto (JP)

(72) Inventors: Kiyomi Fuchigami, Kyoto (JP); Kenzo Yamamoto, Kyoto (JP); Naoya Kitada, Kyoto (JP); Kazuya Shinno, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 511 days.

(21) Appl. No.: 17/141,376

(22) Filed: Jan. 5, 2021

(65) Prior Publication Data

US 2021/0122770 A1    Apr. 29, 2021

Related U.S. Application Data

(63) Continuation of application No. 16/364,410, filed on Mar. 26, 2019, now Pat. No. 10,975,229.

(30) Foreign Application Priority Data

| Mar. 30, 2018 | (JP) | 2018-067797 |
| Mar. 30, 2018 | (JP) | 2018-067798 |
| Mar. 30, 2018 | (JP) | 2018-067799 |

(51) Int. Cl.

| *C07F 7/18* | (2006.01) |
| *A61K 6/71* | (2020.01) |
| *A61K 6/887* | (2020.01) |
| *C08F 230/08* | (2006.01) |
| *C08K 9/06* | (2006.01) |
| *C08L 33/02* | (2006.01) |
| *C09C 3/12* | (2006.01) |
| *C08F 2/48* | (2006.01) |

(52) U.S. Cl.
CPC ............ *C07F 7/1892* (2013.01); *A61K 6/71* (2020.01); *A61K 6/887* (2020.01); *C07F 7/1804* (2013.01); *C08F 230/08* (2013.01); *C08K 9/06* (2013.01); *C08L 33/02* (2013.01); *C09C 3/12* (2013.01); *C08F 2/48* (2013.01); *C08L 2312/08* (2013.01)

(58) Field of Classification Search
CPC ................................... C09C 3/12; C08K 9/06
See application file for complete search history.

(56) References Cited

U.S. PATENT DOCUMENTS

| 5,192,815 A | 3/1993 | Okada et al. |
| 7,932,414 B2 | 4/2011 | Wolter |
| 2015/0343146 A1 | 12/2015 | Monrad et al. |

FOREIGN PATENT DOCUMENTS

| CN | 104768596 | 7/2015 |
| JP | 2-134307 | 5/1990 |
| JP | 3-70778 | 3/1991 |
| JP | 2007-238567 | 9/2007 |
| JP | 2010-229054 | 10/2010 |
| JP | 2015-182963 | 10/2015 |
| JP | 2015-530427 | 10/2015 |
| JP | 2015-196682 | 11/2015 |
| WO | 2014/025385 | 2/2014 |
| WO | 2017/104332 | 6/2017 |

OTHER PUBLICATIONS

Document explaining different types of forces on an adhesive from https://www.adhesives.org/adhesives-sealants/adhesives-sealants-overview/structural-design/types-of-stress (no date).
Office Action issued Dec. 7, 2021 in corresponding Japanese Patent Application No. 2018-067799, with English-language translation.

*Primary Examiner* — Marc S Zimmer
(74) *Attorney, Agent, or Firm* — Wenderoth, Lind & Ponack, L.L.P.

(57) ABSTRACT

The present invention relate to a novel silane coupling agent and a medical and/or dental curable composition comprising the same. It is an object of the present invention to provide a novel silane coupling agent that imparts high affinity to a radical polymerizable monomer, thereby imparting high mechanical strength, flexibility and durability when used for a medical and/or dental curable composition, and an inorganic filler surface-treated with the novel silane coupling agent and a novel medical and/or dental curable composition. A silane coupling agent including repeating units such as a urethane bond and polyethylene glycol (ether bond) at a specific position is used.

5 Claims, No Drawings

SILANE COUPLING COMPOUNDS AND MEDICAL AND/OR DENTAL CURABLE COMPOSITIONS COMPRISING THE SAME

BACKGROUND OF THE INVENTION

Field of the Invention

The present invention relates to a novel silane coupling agent and a medical and/or dental curable composition comprising the same.

Description of the Related Art

In the medical and/or dental field, metal prosthetic appliances and synthetic resin molded articles and the like have been used for repair of defects in bones and teeth. For adhesion thereof to living hard tissues, an adhesive containing an adhesive polymerizable monomer has been frequently used. In the medical and/or dental field, a medical and/or dental curable composition, so-called composite resin, has been used in clinical settings on a daily basis. An uncured body (before radical polymerization) paste is filled in a defect part such as teeth, and then external energy such as photoirradiation is imparted, thus obtaining a radical polymerization cured body.

Generally, in these adhesives and composite resins, (meth)acrylic acid derivative monomers such as methyl methacrylate, triethylene glycol dimethacrylate and urethan-based dimethacrylate have been used. In free radical polymerization (hereinafter referred to as radical polymerization) of vinyl monomers such as these (meth)acrylic acid derivative monomers, a carbon-carbon double bond is cleaved to become a single bond, thus forming a polymer and leading to cure. To this composite resin, not only vinyl monomers but also inorganic fillers are added for the purpose of improving the mechanical strength. Generally, these inorganic fillers are surface-treated with a silane coupling agent having a polymerizable group to attempt to improve the wettability and to improve the mechanical strength. In the medical and/or dental field, conventionally γ-methacryloxy-propyltrimethoxysilane (hereinafter referred to as KBM-503) as the silane coupling agent has been widely used. When a particle that is surface-treated with the compound is used, there were problems that hydrolysis tends to progress due to low hydrophobicity and that the durability of the material is low. Also, there was a drawback that sufficient mechanical strength cannot be obtained.

Therefore, in order to improve the durability and filling rate of the material, a method for using a silane coupling agent having a long alkyl chain (Patent literatures 1 to 3), a method for using a silane coupling agent using a fluoroalkylene group (Patent literature 4) and a method for using a silane coupling agent having many polymerizable groups (Patent literature 5) have been proposed.

Patent literature 1: JP 2-134307 A
Patent literature 2: JP 3-70778 A
Patent literature 3: JP 2015-196682 A
Patent literature 4: JP 2007-238567 A
Patent literature 5: JP 2010-229054 A

DISCLOSURE OF THE INVENTION

Problems to be Solved

However, when the methods mentioned in JP 2-134307 A, JP 3-70778 A and JP 2015-196682 A was applied to a medical and/or dental composite resin, which is one of medical and/or dental curable compositions, there was a room for improvement in the mechanical strength. In other words, simply a long alkyl chain led to lack of flexibility and pressure-sensitive adhesion/adhesion. When the method mentioned in JP 2007-238567 A was applied to a medical and/or dental material, the water resistance was low and the durability of the material was insufficient. Thus, it is insufficient to achieve both the durability and the mechanical strength of a material that used a silane coupling agent of the prior art was insufficient, and there was a room for further improvement.

It is an object of the present invention to provide a novel silane coupling agent that imparts high affinity to a radical polymerizable monomer, thereby imparting high mechanical strength, flexibility and durability when used for a medical and/or dental curable composition, and an inorganic filler surface-treated with the novel silane coupling agent and a novel medical and/or dental curable composition.

Means to Solve the Problems

The inventors of the present application have intensively studied and found that high affinity to a radical polymerizable monomer is imparted by surface-treating an inorganic filler with a silane coupling agent having a specific chemical structure. This enabled to imparting high mechanical strength, flexibility and pressure-sensitive adhesion/adhesion when the silane coupling agent is used for a medical and/or dental curable composition. This is considered to be due to low rotational energy barrier of the —C—O—C— bond. One aspect of the present invention is as follows.

[Item 1]
A silane coupling agent having:
a polymerizable group,
a reactive silyl group and
a spacer group connecting the polymerizable group and the reactive silyl group,
the spacer group having:
a first urethane group and
either an ether group or a second urethane group.

[Item 2]
The silane coupling agent according to item 1, which is represented by the following formula:

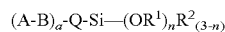

wherein
$(A-B)_a$— represents a polymerizable group, A represents a $H_2C\!=\!CH$—, $H_2C\!=\!C(CH_3)$— or $H_2C\!=\!CH\!-\!C_6H_4$— group ($C_6H_4$ represents a phenylene group), B represents —C(O)—O—, —C(O)—S—, —C(O)—NH—, —NH—C(O)—NH—, —NH—C(O)—S— or —NH—C(O)—O—, a represents an integer of 1 to 6,
—Si—$(OR^1)_n R^2_{(3-n)}$ represents a reactive silyl group, $R^1$ represents a C1-C6 linear or branched alkyl group, $R^2$ represents a C1-C16 linear or branched alkyl group, a phenyl group or a halogen atom, and n represents an integer of 0 to 3, and when n is 0, at least one or more halogen atoms are bonded to Si, and
Q- represents a spacer group.

[Item 3]
The silane coupling agent according to item 1 or 2, wherein the ether group is an ether group having a structure selected from —O—$CH_2$—$CH_2$—, —O—CH ($CH_3$)—$CH_2$— or —O—$CH_2$—CH($CH_3$)—.

[Item 4]

The silane coupling agent according to any one of items 1 to 3, wherein the spacer group is anyone selected from the group consisting of the following spacer groups I to III.

Spacer group I:

—$Z^1$—NH—C(O)$OR^3$—     Formula (I)

wherein
- $Z^1$ is a C2-C30 linear or branched saturated aliphatic hydrocarbon group, and has at least one or more of —$CH_2$—$CH_2$—O—, —O—CH($CH_3$)—$CH_2$— and —O—$CH_2$—CH($CH_3$)— groups,
- $R^3$ is a C7-C30 linear or branched alkylene group, and may have one or more of —S—, —NH—, —NR″— ($R″$ represents an alkylene group), —$CH_2$—$C_6H_4$— ($C_6H_4$ represents a phenylene group), —C(O)—O—, —O—, —$CH_2$—$CH_2$—O—, —O—CH($CH_3$)—$CH_2$— and —O—$CH_2$—CH($CH_3$)— groups.

Spacer group II:

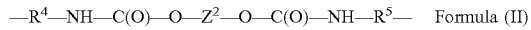
—$R^4$—NH—C(O)—O—$Z^2$—O—C(O)—NH—$R^5$—     Formula (II)

wherein
- $R^4$ is a C2-C100 linear or branched saturated aliphatic hydrocarbon group, and may have one or more of —O—$CH_2$—$CH_2$—, —O—CH($CH_3$)—$CH_2$— and —O—$CH_2$—CH($CH_3$)— groups,
- $Z^2$ is a C2-C100 linear or branched alkylene group, and has at least one or more of —O—$CH_2$—$CH_2$—, —O—CH($CH_3$)—$CH_2$— and —O—$CH_2$—CH($CH_3$)— groups,
- $R^5$ is a C2-C100 linear or branched alkylene group, and may have one or more of —S—, —NH—, —NR″— ($R″$ represents an alkylene group), —$CH_2$—$C_6H_4$— ($C_6H_4$ represents a phenylene group), —C(O)—O—, —O—, —O—$CH_2$—$CH_2$—, —O—CH($CH_3$)—$CH_2$— and —O—$CH_2$—CH($CH_3$)— groups.

Spacer group III:

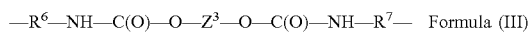
—$R^6$—NH—C(O)—O—$Z^3$—O—C(O)—NH—$R^7$—     Formula (III)

wherein
- $R^6$ is a C2-C100 linear or branched saturated aliphatic hydrocarbon group, and may have one or more of —O—$CH_2$—$CH_2$—, —O—CH($CH_3$)—$CH_2$— and —CH($CH_3$)—$CH_2$—O— groups,
- $Z^3$ is a C2-C100 linear or branched alkylene group,
- $R^7$ is a C2-C100 linear or branched alkylene group, and may have one or more of —S—, —NH—, —NR″— ($R″$ represents an alkylene group), —$CH_2$—$C_6H_4$— ($C_6H_4$ represents a phenylene group), —C(O)—O—, —O—, —O—$CH_2$—$CH_2$—, —O—CH($CH_3$)—$CH_2$— and —CH($CH_3$)—$CH_2$—O— groups.

[Item 5]

The silane coupling agent according to any one of items 1 to 4, which is synthesized using a compound having any one of the following structures (2-(2-isocyanatoethoxy)ethyl methacrylate or 2-(2-isocyanatoethoxy)ethyl acrylate):

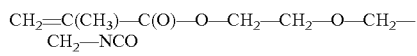
$CH_2$=C($CH_3$)—C(O)—O—$CH_2$—$CH_2$—O—$CH_2$—$CH_2$—NCO

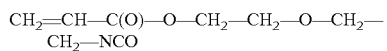
$CH_2$=CH—C(O)—O—$CH_2$—$CH_2$—O—$CH_2$—$CH_2$—NCO

[Item 6]

An inorganic filler which is surface-treated with the silane coupling agent according to any one of items 1 to 5.

[Item 7]

A medical and/or dental curable composition comprising the inorganic filler according to item 6, a radical polymerizable monomer other than the silane coupling agent, and either a polymerization initiator or a polymerization accelerator.

Effect of the Invention

By surface-treating an inorganic filler with the silane coupling agent of the present invention, high affinity to a radical polymerizable monomer is expressed, thus imparting high mechanical strength, flexibility and pressure-sensitive adhesion/adhesion to a medical and/or dental curable composition. Use of the present invention may also impart less polymerization shrinkage.

This high affinity effect remarkably appears when a radical polymerizable monomer has an urethane group. This is considered to be due to the fact that the silane coupling agent has an urethan bond. In other words, an inorganic filler surface-treated with the silane coupling agent of the present invention has a surface on which an urethane group is introduced, which is considered to express remarkable high affinity to a radical polymerizable monomer having an urethane group. The present invention enables highly filling of an inorganic filler, thus enabling achievement of high mechanical strength. Since the silane coupling agent molecule of the present invention has a repeating unit such as elastic polyethylene glycol (ether bond), the flexibility, pressure-sensitive adhesion and durability may be greatly improved.

DETAILED DESCRIPTION OF THE INVENTION

[Silane Coupling Agent]

The silane coupling agent having a radical polymerizable group in the present invention has a polymerizable group, a reactive silyl group and a spacer group connecting the polymerizable group and the reactive silyl group. The silane coupling agent may be used alone, or a plurality of silane coupling agents may be used in combination.

The silane coupling agent may be represented by the following formula:

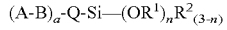
(A-B)$_a$-Q-Si—($OR^1$)$_n$$R^2_{(3-n)}$ wherein
- (A-B)$_a$— represents a polymerizable group, A represents a $H_2C$=CH—, $H_2C$=C($CH_3$)— or $H_2C$=CH—$C_6H_4$— group ($C_6H_4$ represents a phenylene group), B represents —C(O)—O—, —C(O)—S—, —C(O)—NH—, —NH—C(O)—NH—, —NH—C(O)—S— or —NH—C(O)—O—, a represents an integer of 1 to 6,
- —Si—($OR^1$)$_n$$R^2_{(3-n)}$ represents a reactive silyl group, $R^1$ represents a C1-C6 linear or branched alkyl group, $R^2$ represents a C1-C16 linear or branched alkyl group, a phenyl group or a halogen atom and n represents an integer of 0 to 3, and when n is 0, at least one or more halogen atoms are bonded to Si and
- Q- represents a spacer group.

(Polymerizable Group)

The polymerizable group is a group having a vinyl group, and, for example, a group having a (meth)acrylic group. "(Meth)acrylic" as used herein means "acrylic" and "methacrylic".

The polymerizable group may be a group represented by the following general formula:

(A-B)$_a$— wherein

A represents a H$_2$C=CH—, H$_2$C=C(CH$_3$)— or H$_2$C=CH—C$_6$H$_4$— group (C$_6$H$_4$ represents a phenylene group), B represents —C(O)—O—, —C(O)—S—, —C(O)—NH—, —NH—C(O)—NH—, —NH—C(O)—S— or —NH—C(O)—O—, and a represents an integer of 1 to 6 (for example, 1 to 4, and preferably 1 or 2).

(Reactive Silyl Group)

The reactive silyl group is a group that produces a silanol group by hydrolysis. The silanol group thus produced can, for example, form a hydrogen bond with a hydroxy group or form a chemical bond by a condensation reaction.

The reactive silyl group may be a group represented by the following general formula:

—Si—(OR$^1$)$_n$R$^2$$_{(3-n)}$ wherein

R$^1$ represents a C1-C6 linear or branched alkyl group, R$^2$ represents a C1-C16 linear or branched alkyl group, a phenyl group or a halogen atom, and n represents an integer of 0 to 3, and when n is 0, at least one or more halogen atoms are bonded to Si.

(Spacer Group)

The spacer group has at least one urethane group mentioned above (also referred to as first urethane group).

The spacer group further has at least either an ether group or a second urethane group. The ether group may be an ether group having a structure selected from —O—CH$_2$—CH$_2$—, —O—CH(CH$_3$)—CH$_2$— or —O—CH$_2$—CH(CH$_3$)—.

The spacer group may be selected from the following spacer groups I to III.

Spacer Group I

The spacer group I is represented by the following formula:

—Z$^1$—NH—C(O)OR$^3$—   Formula (I)

wherein

Z$^1$ is a C2-C30 linear or branched saturated aliphatic hydrocarbon group, and has at least one or more of —CH$_2$—CH$_2$—O—, —O—CH(CH$_3$)—CH$_2$— and —O—CH$_2$—CH(CH$_3$)—, R$^3$ is a C7-C30 linear or branched alkylene group, and may have one or more of —S—, —NH—, —NR″— (R″ represents an alkylene group), —CH$_2$—C$_6$H$_4$— (C$_6$H$_4$ represents a phenylene group), —C(O)—O—, —O—, —CH$_2$—CH$_2$—O—, —O—CH(CH$_3$)—CH$_2$— and —O—CH$_2$—CH(CH$_3$)— groups. The saturated aliphatic hydrocarbon group may be divalent to septivalent, and for example, is divalent to pentavalent, and preferably divalent or trivalent.

Representative chemical structures of compounds of the embodiments of the silane coupling agent having a spacer group I will be described below.

[Chemical Formula 1]

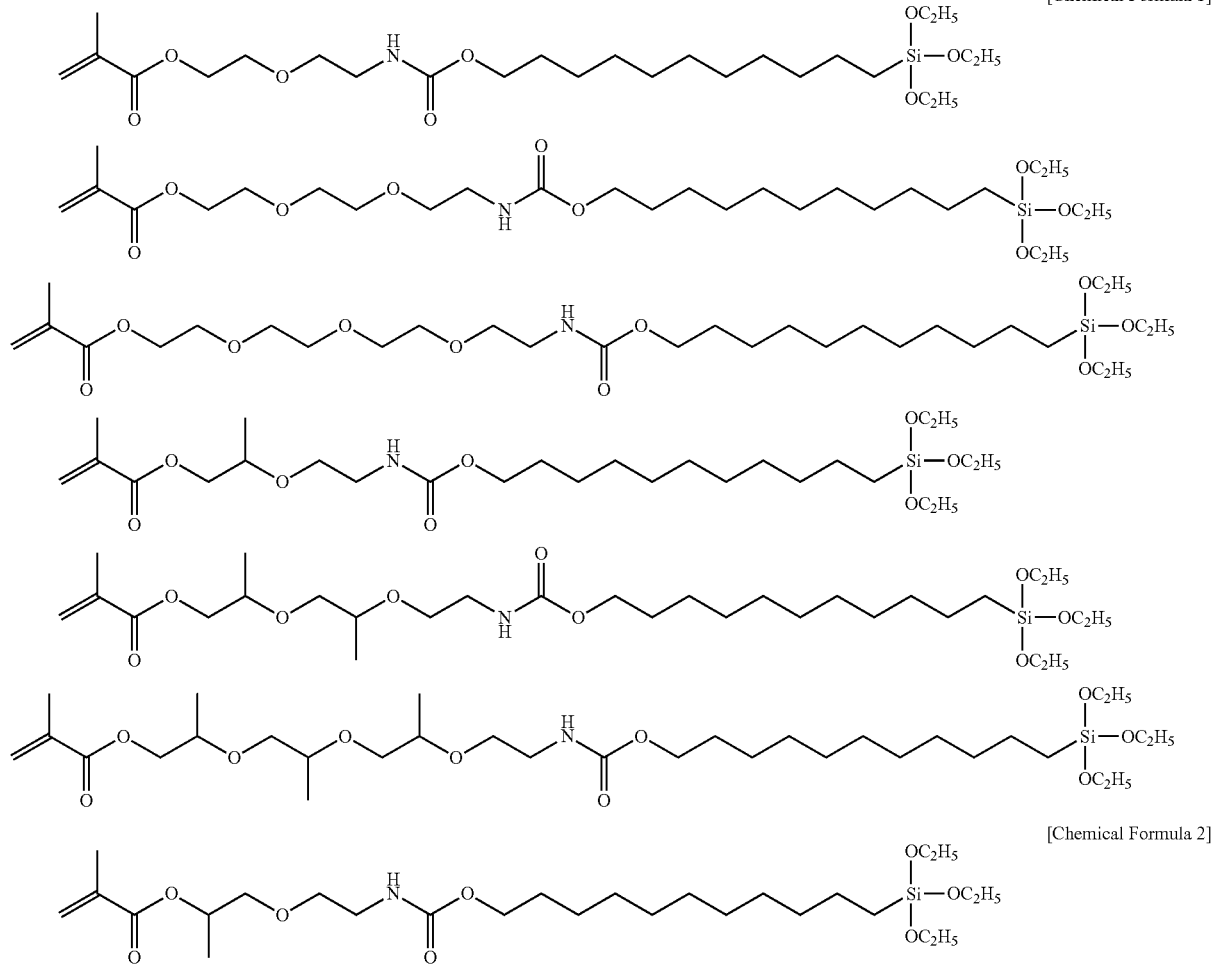

[Chemical Formula 2]

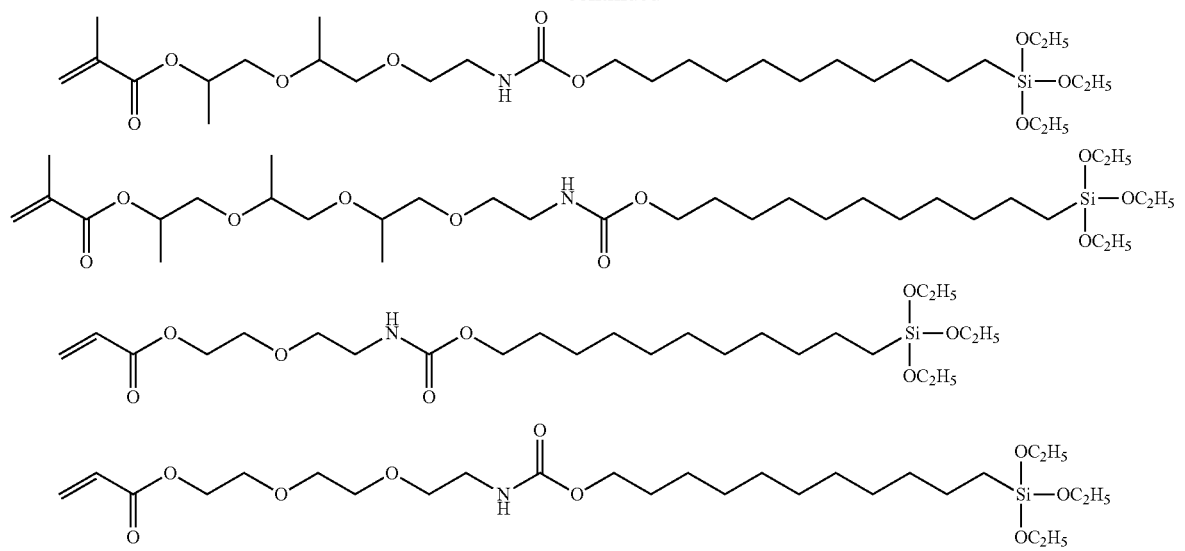
[Chemical Formula 3]
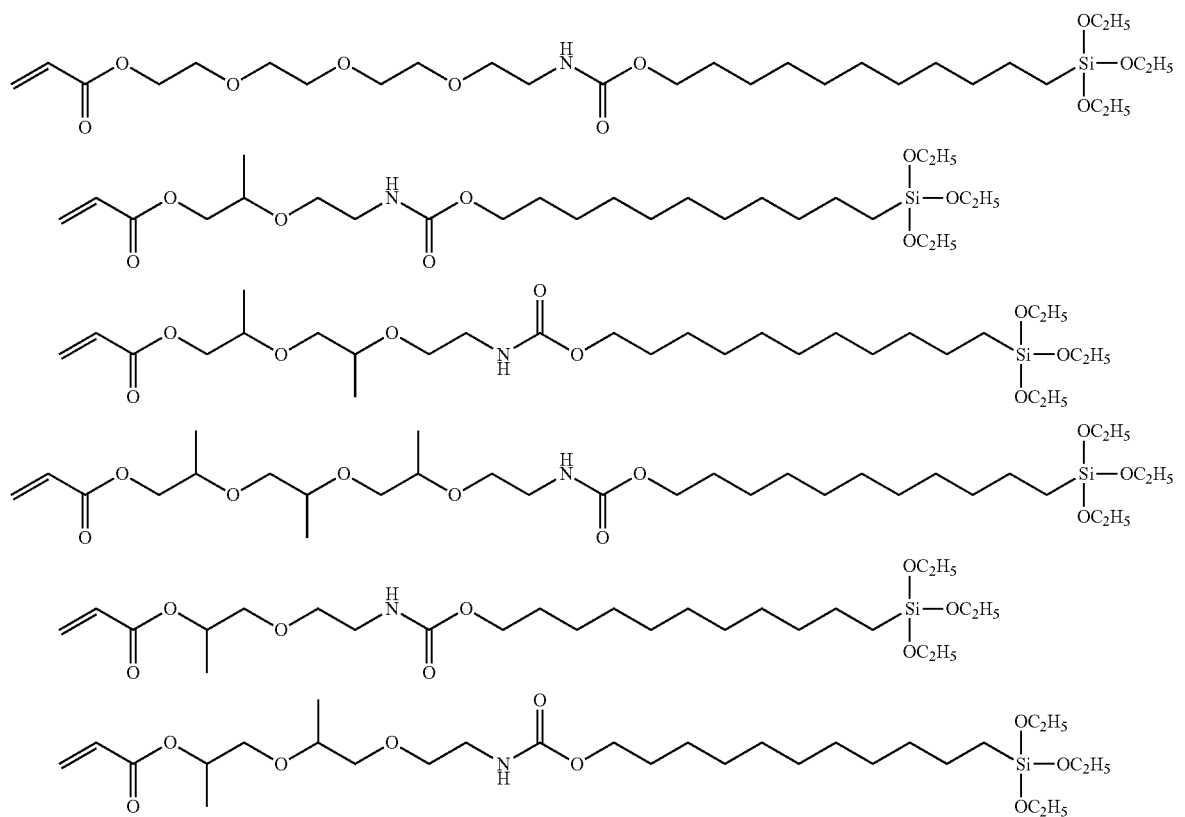
[Chemical Formula 4]
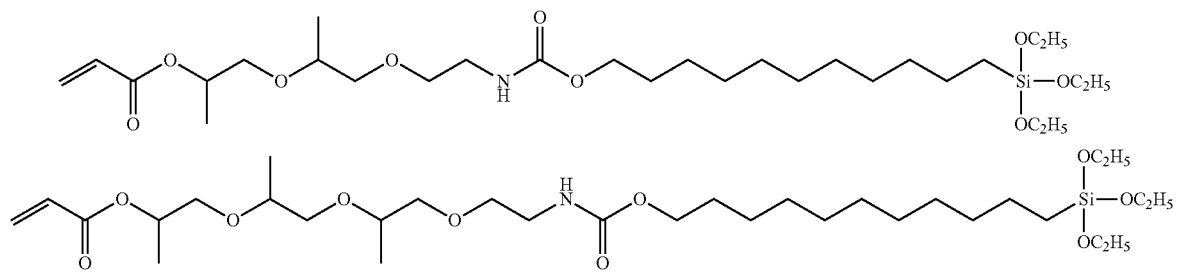

-continued

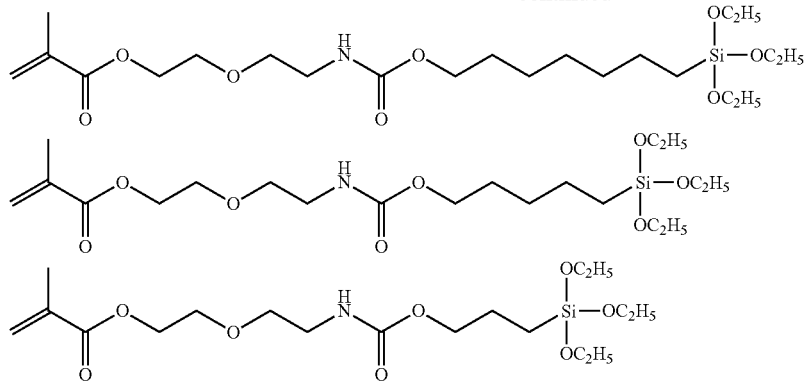

Spacer Group II

The spacer group II is represented by the following formula:

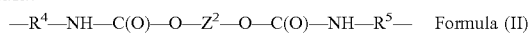

wherein $R^4$ is a C2-C100 linear or branched saturated aliphatic hydrocarbon group, and may have one or more of —O—CH$_2$—CH$_2$—, —O—CH(CH$_3$)—CH$_2$— and —O—CH$_2$—CH(CH$_3$)—, $Z^2$ is a C2-C100 linear or branched alkylene group, and has at least one or more of —O—CH$_2$—CH$_2$—, —O—CH(CH$_3$)—CH$_2$— and —O—CH$_2$—CH(CH$_3$)—, $R^5$ is a C2-C100 linear or branched alkylene group, and may have one or more of —S—, —NH—, —NR″— (R″ represents an alkylene group), —CH$_2$—C$_6$H$_4$— (C$_6$H$_4$ represents a phenylene group), —C(O)—O—, —O—, —O—CH$_2$—CH$_2$—, —O—CH(CH$_3$)—CH$_2$— and —O—CH$_2$—CH(CH$_3$)— groups.

The saturated aliphatic hydrocarbon group may be divalent to septivalent, and for example, is divalent to pentavalent, and preferably divalent or trivalent.

Representative chemical structures of compounds of the embodiments of the silane coupling agent having a spacer group II will be described below.

[Chemical Formula 5]

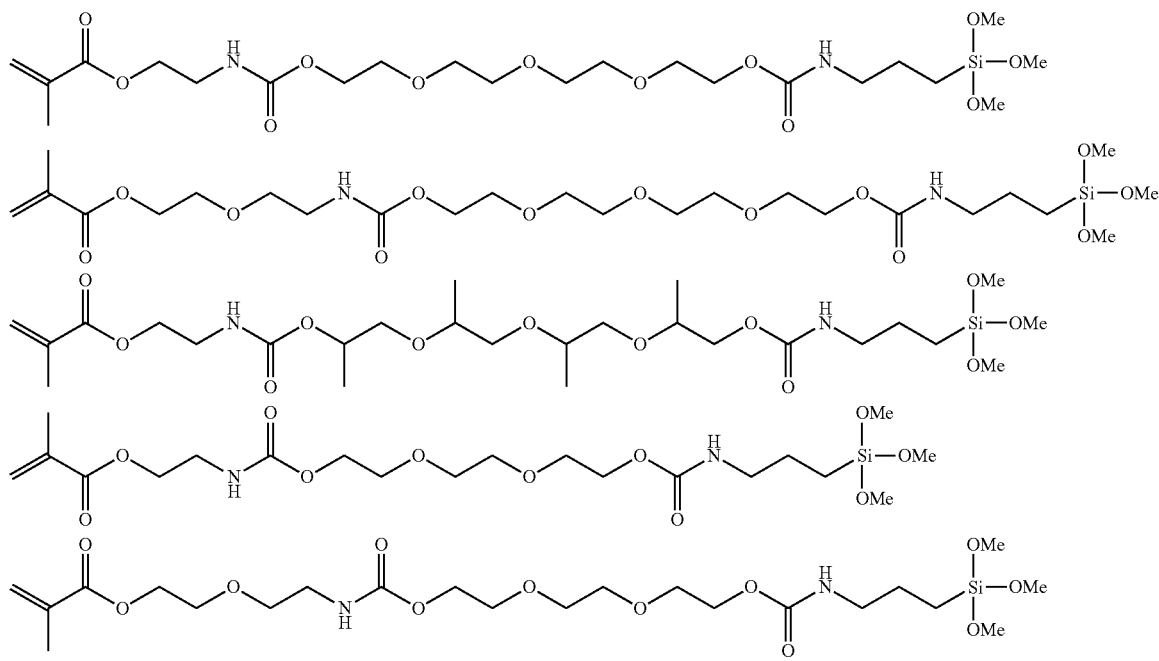

[Chemical Formula 6]

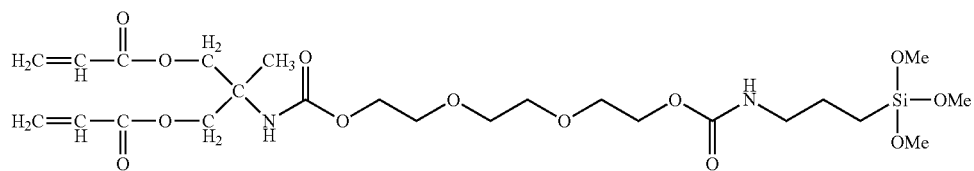

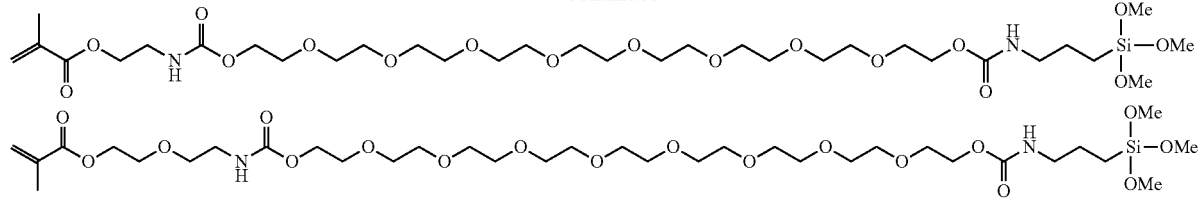

Spacer Group III

The spacer group III is represented by the following formula:

—R$^6$—NH—C(O)—O—Z$^3$—O—C(O)—NH—R$^7$—   Formula (III)

wherein

R$^6$ is a C2-C100 linear or branched saturated aliphatic hydrocarbon group, and may have one or more of —O—CH$_2$—CH$_2$—, —O—CH(CH$_3$)—CH$_2$— and —CH(CH$_3$)—CH$_2$—O—, Z$^3$ is a C2-C100 linear or branched alkylene group, R$^7$ is a C2-C100 linear or branched alkylene group, and may have one or more of —S—, —NH—, —NR″— (R″ represents an alkylene group), —CH$_2$—C$_6$H$_4$— (C$_6$H$_4$ represents a phenylene group), —C(O)—O—, —O—, —O—CH$_2$—CH$_2$—, —O—CH(CH$_3$)—CH$_2$— and —CH(CH$_3$)—CH$_2$—O— groups.

The saturated aliphatic hydrocarbon group may be divalent to septivalent, and for example, is divalent to pentavalent, and preferably divalent or trivalent.

Representative chemical structures of compounds of the embodiments of the silane coupling agent having a spacer group III will be described below.

[Chemical Formula 7]

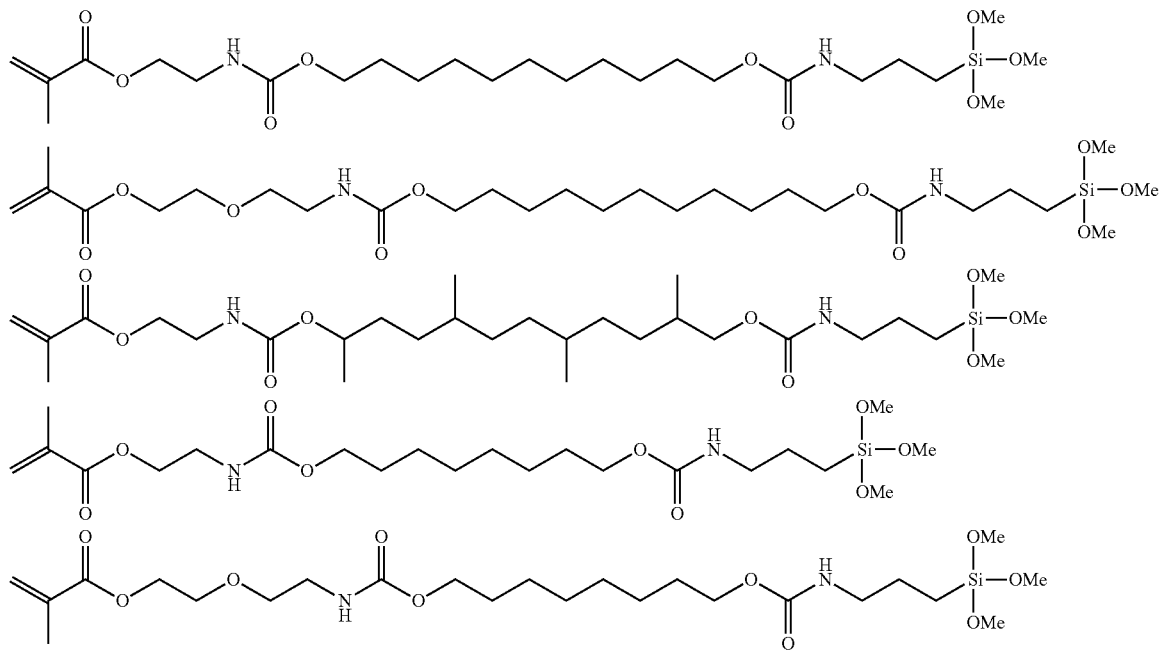

[Chemical Formula 8]

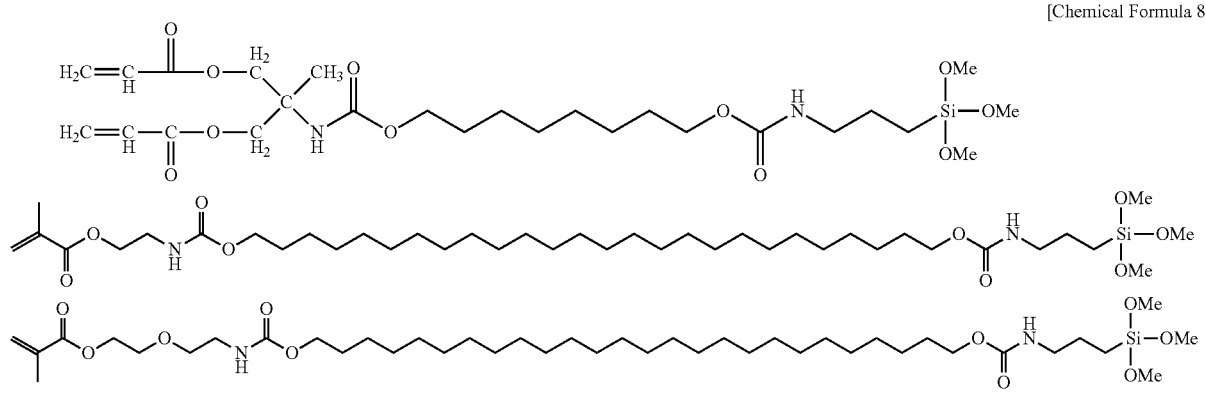

The silane coupling agent in the present invention may be a silane coupling agent synthesized using a compound having any one of the following structures (2-(2-isocyanatoethoxy)ethyl methacrylate or 2-(2-isocyanatoethoxy)ethyl acrylate):

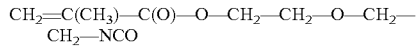

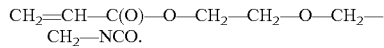

Therefore, the silane coupling agent may have the following structures:

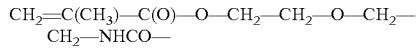

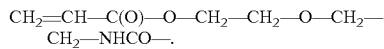

When an inorganic filler is surface-treated using the silane coupling agent of the embodiments of the present invention, the treatment concentration is generally preferably 0.05 mass time to 10 mass times the concentration of the inorganic filler although it depends on the density (mol/g) of the silanol group of the mother particle. Treatment with a concentration lower than 0.05 mass time is not preferable since the silane coupling agent cannot be sufficiently introduced, and a treatment with a concentration exceeding 10 mass times is not preferable since a condensate of only the silane coupling agent is produced, affecting the mechanical strength.

Although their chemical compositions are not particularly limited, examples of the inorganic filler treated with the silane coupling agent of the embodiments of the present invention include silicon dioxide, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, strontium calcium fluoroaluminosilicate glass and the like. Particularly, barium fluoroaluminosilicate glass, strontium fluoroaluminosilicate glass, fluoroaluminosilicate glass and the like, which are used in medical and/or dental glass ionomer cement, resin modified glass ionomer cement and resin cement and the like, can also be suitably used. The fluoroaluminosilicate glass as used herein has a basic structure of silicon oxide and aluminum oxide and contains an alkali metal for introducing non-crosslinked oxygen. The fluoroaluminosilicate glass further has an alkaline earth metal including strontium and fluorine as modified/coordinated ions. The fluoroaluminosilicate glass is also a composition in which a lanthanoid series element is incorporated into the skeleton in order to impart further radiopacity. This lanthanoid series element also participates in the composition as a modified/coordinated ion according to the composition range. These inorganic fillers may be used alone or as a mixture of two or more. The composition ratio of the inorganic filler treated with the silane coupling agent of the embodiments of the present invention in the medical and/or dental curable composition in the present invention is not particularly limited, and is preferably in the range of 25 to 90% by weight. It is not preferable that the composition ratio is 25% by weight or less since the mechanical (physical) strength of the cured product is low. It is not preferable that the composition ratio is 90% by weight or more since clinical operability is poor due to too high viscosity of the prepared paste. Furthermore, the average particle size of the inorganic filler is preferably 0.001 to 100 μm, and more preferably 0.001 to 10 μm. Furthermore, the shape of the inorganic filler may be either spherical or indefinite shape. "Average particle size" as used herein means a particle size at an integrated value of 50% in the particle size distribution determined by a laser diffraction/scattering method.

When the silane coupling agent of the embodiments of the present invention is applied to the medical and/or dental curable composition, the radical polymerizable monomer to be included is included in the medical and/or dental curable composition in the amount of preferably 10 to 60% by weight, and more preferably 15 to 30% by weight. When the amount is 10% by weight or less, the viscosity of the medical and/or dental curable composition is too high, which may cause defects, and when the ratio is 60% by weight or more, the strength of the medical and/or dental curable composition may decrease.

As the radical polymerizable monomer used in the medical and/or dental curable composition of the embodiments of the present invention, a radical polymerizable monomer that has been used in the medical and/or dental field can be used without limitation, and it is preferable that the molecular skeleton thereof has an urethan bond. The urethan bond (—NH—C(O)—O—) is for effectively forming a hydrogen bond with the silane coupling agent of the embodiments of the present invention. Examples of the radical polymerizable monomer as used herein include 7,7,9-trimethyl-4,13-dioxo-3,14-dioxa-5,12-diazahexadecane-1,16-diyl dimethacrylate (UDMA) synthesized by a urethan reaction of 2,2,4-trimethylhexamethylene diisocyanate with 2-hydroxyethyl methacrylate (HEMA), radical polymerizable monomers synthesized by a urethan reaction of HEMA or hydroxyethyl acrylate (HEA) with each of 2,4-toluylenediisocyanate, hydrogenated diphenylmethane diisocyanate, naphthalene diisocyanate or hexamethylene diisocyanate, urethan diacrylates obtained by reaction with aliphatic and/or aromatic diisocyanate glycerol (meth)acrylate or 3-methacrylol-2-hydroxypropyl ester, an urethan reactant of 1,3-bis(2-isocyanate,2-propyl)benzene with a compound having a hydroxy group and the like. More specific examples thereof include 2,7,7,9,15-pentamethyl-4,13-dioxo-3,14-dioxa-5,12-diazahexadecane-1,16-diyl diacrylate, 2,7,7,9,15-pentamethyl-4,13-18-trioxo-3,14,17-trioxa-5,12-diazaicos-19-enyl methacrylate, 2,8,10,10,15-pentamethyl-4,13,18-trioxo-3,14,17-trioxa-5,12-diazaicos-19-enyl methacrylate, 2,7,7,9,15-pentamethyl-4,13-dioxo-3,14-dioxa-5,12-diaza-hexadecane-1,16-diylbis(2-methylacrylate), 2,2'-(cyclohexane-1,2-diylbis(methylene))bis(azanediyl)bis(oxomethylene)bis(oxy)bis (propane-2,1-diyl)diacrylate, 2-((2-(((1-(acryloyloxy)propan-2-yloxy)carbonylamino)methyl)cyclohexyl)methylcarbamoyloxy)prop yl methacrylate, 2,2'-(cyclohexane-1,2-diylbis(methylene))bis(azanediyl)bis (oxomethylene)bis(oxy)bis(propane-2,1-diyl)bis(2-methylacrylate), 2,2'-(bicyclo[4.1.0]heptane-3,4-diylbis(methylene))bis(azanediyl)bis(oxomethylene)bis(oxy)bis (propane-2,1-diyl)diacrylate, 2-((4-(((1-(acryloyloxy)propan-2-yloxy)carbonylamino)methyl)bicyclo[4.1.0] heptan-3-yl)methylcarbamoyloxy)propyl methacrylate, 2,2'-(bicyclo[4.1.0]heptane-3,4-diylbis(methylene))bis (azanediyl)bis(oxomethylene)bis(oxy)bis(propane-2,1-diyl) bis(2-methylacrylate), 7,7,9-trimethyl-4,13-dioxo-3,14-dioxa-5,12-diazahexadecane-1,16-diyl diacrylate, 7,7,9-trimethyl-4,13,18-trioxo-3,14,17-trioxa-5,12-diazaicos-19-enyl methacrylate, 8,10,10-trimethyl-4,13,18-trioxo3,14,17-trioxa-5,12-diazaicos-19-enyl methacrylate, 7,7,9-trimethyl- 4,13-dioxo-3,14-dioxa-5,12-diazahexadecane-1,16-diylbis(2-methylacrylate), 4,13-dioxo-3,14-dioxa-5,12-diazahexadecane-1,16-diyl diacrylate, 4,13,18-trioxo-3,14,17-trioxa-5,12-diazaicos-19-enyl methacrylate, 4,13-dioxo-3,14-dioxa-5,12-diazahexadecane-1,16-diylbis(2-methylacrylate), 2-(1-(2-((2-(acryloyloxy)ethoxy)carbonylamino)-4,4-dimethylcyclohexyl)ethylcarbamoyloxy)ethyl methacrylate, 2-(1-(2-((2-(acryloyloxy)ethoxy)carbonylamino)ethyl)-5,5-dimethylcyclohexylcarbamoyloxy)ethyl methacrylate, 2-(2-(((1-(methacryloyloxy)propan-2-yloxy)carbonylamino)methyl)-2,5,5-trimethylcyclohexylcarbamoyloxy)propane-1,3-diylbis(2-methylacrylate), 2-(2-(((1-(methacryloyloxy)propan-2-yloxy)carbonylamino)methyl)-2,5,5-trimethylcyclohexylcarbamoyloxy)propane-1,3-diyl diacrylate, 2-(2-(((1-(acryloyloxy)propan-2-yloxy)carbonylamino)methyl)-2,5,5-trimethylcyclohexylcarbamoyloxy)propane-1,3-diylbis(2-methylacrylate), 3-(15-(2-(acryloyloxy)ethyl)-3,12,19-trioxo-2,13,18-trioxa-4,11-diazahenicos-20-enyl)pentane-1,5-diyl diacrylate, 3-(15-(2-(acryloyloxy)ethyl)-3,12,19-trioxo-2,13,18-trioxa-4,11-diazahenicos-20-enyl)pentane-1,5-diylbis(2-methylacrylate), 2,2'-(cyclihexane-1,2-diylbis(methylene))bis(azanediyl)bis(oxomethylene)bis(oxy)bis(ethane-2,1-diyl)diacrylate, 2-((2-(((2-(acryloyloxy)ethoxy)carbonylamino)methyl)cyclohexyl)methylcarbamoyloxy)ethyl methacrylate, 2,2'-(cyclihexane-1,2-diylbis(methylene))bis(azanediyl)bis(oxomethylene)bis(oxy)bis(ethane-2,1-diyl)bis(2-methylacrylate), 2,15-bis(cyclohexyloxymethyl)-4,13-dioxo-3,14-dioxa-5,12-diazahexadecane-1,16-diyl diacrylate, 2,15-bis(cyclohexyloxymethyl)-4,13-dioxo-3,14-dioxa-5,12-diazahexadecane-1,16-diylbis(2-methylacrylate), 2,15-bis(cyclohexyloxymethyl)-4,13,18-trioxo-3,14,17-trioxa-5,12-diazaicos-19-enyl methacrylate, 1,18-bis(cyclohexyloxy)-5,14-dioxo-4,15-dioxa-6,13-diazaoctadecane-2,17-diyl diacrylate, 1-(cyclohexyloxy)-17-(cyclohexyloxymethyl)-5,14,19-trioxo-4,15,18-trioxa-6,13-diazahenicos-20-en-2-yl methacrylate, 1,18-bis(cyclohexyloxy)-5,14-dioxo-4,15-dioxa-6,13-diazaoctadecane-2,17-diylbis(2-methylacrylate), 7,7,9-trimethyl-4,13-dioxo-3,14-dioxa-5,12-diazahexadecane-1,16-diylbis(2-methylacrylate), 7,7,9-trimethyl-4,13-dioxo-3,14-dioxa-5,12-diazahexadecane-1,16-diyl diacrylate, 2,2'-(1,3-phenylenebis(methylene))bis(azanediyl)bis(oxomethylene)bis(oxy)bis(ethane-2,1-diyl)bis(2-methacrylate), 2,2'-(1,3-phenylenebis(methylene))bis(azanediyl)bis(oxomethylene)bis(oxy)bis(ethane-2,1-diyl) diacrylate, 2-(3-(((2-(acryloyloxy)ethoxy)carbonylamino)methyl)benzylcarbamoyloxy)ethyl methacrylate, 2,2'-(1,3-phenylenebis(methylene))bis(methylazanediyl)bis(oxomethylene) bis(oxy)bis(ethane-2,1-diyl)bis(2-methacrylate), 2,2'-(1,3-phenylenebis(methylene))bis(methylazanediyl)bis(oxomethylene) bis(oxy)bis(ethane-2,1-diyl)diacrylate, 2-((3-((((2-(acryloyloxy)ethoxy)carbonyl)(methyl)amino)methyl)benzyl)(methyl)carbamoyloxy)ethyl methacrylate, 2,2'-(1,3-phenylenebis(methylene))bis(azanediyl)bis(oxomethylene)bis(oxy)bis(propane-2,1-diyl)bis(2-methylacrylate), 2,2'-(1,3-phenylenebis(methylene))bis(azanediyl)bis(oxomethylene)bis(oxy)bis(propane-2,1-diyl)diacrylate, 2-(3-(((2-(acryloyloxy)ethoxy)carbonylamino)methyl)benzylcarbamoyloxy)propyl methacrylate, 2-(3-(((1-(acryloyloxy)propan-2-yloxy)carbonylamino)methyl)benzylcarbamoyloxy)ethyl methacrylate, 4,4'-(1,3-phenylenebis(methylene))bis(azanediyl)bisoxomethylene)bis(oxy)bis(4,1-phenylene)bis(2-methylacrylate), 4,4'-(1,3-phenylenebis(methylene))bis(azanediyl)bisoxomethylene)bis(oxy)bis(4,1-phenylene)diacrylate, 4-(3-(((4-(acryloxy)phenoxy)carbonylamino)methyl)benzylcarbamoyloxy)phenyl methacrylate, 4,4'-(1,3-phenylenebis(methylene))bis(azanediyl)bis(oxomethylene)bis(oxy)bis(butane-4,1-diyl)bis(2-methylacrylate), 4,4'-(1,3-phenylenebis(methylene))bis(azanediyl)bis(oxomethylene)bis(oxy)bis(butane-4,1-diyl)diacrylate, 4-(3-(((4-(acryloyloxy)butoxy)carbonylamino)methyl)benzylcarbamoyloxy)butyl methacrylate, 2,2'-(1,3-phenylenebis(methylene))bis(azanediyl)bis(oxomethylene)bis(oxy)bis(3-phenoxypropane-2,1-diyl)bis(2-methylacrylate), 2,2'-(1,3-phenylenebis(methylene))bis(azanediyl)bis(oxomethylene)bis(oxy)bis(3-phenoxypropane-2,1-diyl)diacrylate, 2-(3-(((1-(acryloyloxy)-3-phenoxypropan-2-yloxy)carbonylamino)methyl)benzylcarbamoyloxy)-3-phenoxypropyl methacrylate, 2-2'-(1,3-phenylenebis(methylene))bis(azanediyl)bis(oxomethylene)bis(oxy)bis(3-(phenylamino)propane-2,1-diyl)bis(2-methylacrylate), 2-2'-(1,3-phenylenebis(methylene))bis(azanediyl)bis(oxomethylene)bis(oxy)bis(3-(phenylamino)propane-2,1-diyl)diacrylate, 2-(3-(((1-(acryloyloxy)-3-(phenylamino)propan-2-yloxy)carbonylamino)methyl)benzylcarbamoyloxy)-3-(phenylamino)propyl methacrylate, 2,2'-(1,3phenylenebis(methylene))bis(azanediyl)bis(oxomethylene)bis(oxy)bis(3-(phenylthio)propane-2,1-diyl)bis(2-methylacrylate), 2,2'-(1,3phenylenebis(methylene))bis(azanediyl)bis(oxomethylene)bis(oxy)bis(3-(phenylthio)propane-2,1-diyl)diacrylate, 2-(3-(((1-(acryloxy)-3-(phenylthio)propan-2-yloxy)carbonylamino)methyl)benzylcarbamoyloxy)-3-(phenylthio)propyl methacrylate, 2,2'-(1,3-phenylenebis(methylene))bis(azanediyl)bis(oxomethylene)bis(oxy)bis(3-(benzyloxy)propane-2,1-diyl)bis(2-methylacrylate), 2,2'-(1,3-phenylenebis(methylene))bis(azanediyl)bis(oxomethylene)bis(oxy)bis(3-(benzyloxy)propane-2,1-diyl)diacrylate, 2-(3-(((1-(acryloyloxy)-3-(benzyloxy)propan-2-yloxy)carbonylamino)methyl)benzylcarbamoyloxy)-3-(benzyloxy)propyl methacrylate, 2,2'-(1,3-phenylenebis(methylene))bis(azanediyl)bis(oxomethylene)bis(oxy)bis(3-(methacryloyloxy)propane-2,1-diyl)dibenzoate, 2,2'-(1,3-phenylenebis(methylene))bis(azanediyl)bis(oxomethylene)bis(oxy)bis(3-(acryloyloxy)propane-2,1-diyl)dibenzoate, 2,2'-(1,3-phenylenebis(methylene))bis(azanediyl)bis(oxomethylene)bis(oxy)bis(3-(2-phenylacetoxy)propane-2,1-diyl)bis(2-methylacrylate), 2,2'-(1,3-phenylenebis(methylene))bis(azanediyl)bis(oxomethylene)bis(oxy)bis(3-(2-phenylacetoxy)propane-2,1-diyl)diacrylate, 2-(3-(((1-(acryloyloxy)-3-(2-phenylacetoxy)propan-2-yloxy)carbonylamino)methyl)benzylcarbamoyloxy)-3-(2-phenylacetoxy)propyl methacrylate, 2,2'-(2,2'-(1,3-phenylene)bis(propane-2.2-diyl))bis(azanediyl)bis(oxomethylene)bis(oxy)bis(ethane-2,1-diyl)bis(2-methacrylate), 2,2'-(2,2'-(1,3-phenylene)bis(propane-2,2-diyl))bis(azanediyl)bis(oxomethylene)bis(oxy)bis(ethane-2,1-diyl)diacrylate, 2-(2-(3-(2-((2-(acryloyloxy)ethoxy)carbonylamino)propan-2-yl)phenyl)propan-2-ylcarbamoyloxy)ethyl methacrylate, 2,2'-(2,2'-(1,3-phenylene)bis(propane-2,2-diyl))bis(methylazanediyl)bis(oxomethylene)bis(oxy)bis(ethane-2,1-diyl)bis(2-methacrylate), 2,2'-(2,2'-(1,3-phenylene)bis(propane-2,2-diyl))bis(methylazanediyl)bis(oxomethylene)bis(oxy)bis(ethane-2,1-diyl)diacrylate, 2-((2-(3-(2-(((2-(acryloyloxy)ethoxy)carbonyl)(methyl)amino)propan-2-yl)phenyl)propan-2-yl)(methyl)carbamoyloxy)ethyl methacrylate, 2,2'-(2,2'-(1,3-phenylene)bis(propane-2,2-diyl))bis(azanediyl)bis(oxomethylene)bis(oxy)bis(propane-2,1-diyl)bis(2-methylacrylate), 2,2'-(2,2'-(1,3-phenylene)bis(propane-2,2-diyl))bis(azanediyl)bis(oxomethylene)bis(oxy)bis (propane-2,1-diyl)diacrylate, 2-(2-(3-(2-((2-(acryloyloxy)ethoxy)carbonylamino)propan-2-yl)phenyl)propan-2-ylcarbamoyloxy)propyl methacrylate, 2-(2-(3-(2-((1-(acryloyloxy)propan-2-yloxy)carbonylamino)propan-2-ylcarbamoylxy)ethyl methacrylate, 4,4'-(2,2'-(1,3-phenylene)bis(propane-2,2-diyl))bis(azanediyl)bis(oxomethylene)bis(oxy)bis(4,1-phenylene)bis(2-methylacrylate), 4,4'-(2,2'-(1,3-phenylene)bis(propane-2,2-diyl))bis(azanediyl)bis(oxomethylene)bis(oxy)bis(4,1-phenylene)diacrylate, 4-(2-(3-(2-((4-(acryloyloxy)phenoxy)carbonylamino)propan-2-yl)phenyl)propan-2-ylcarbamoylxy)phenyl methacrylate, 4,4'-(2,2'-(1,3-phenylene)bis(propane-2,2-diyl))bis(azanediyl)bis(oxomethylene)bis(oxy)bis(butane-4,1-diyl)bis(2-methacrylate), 4,4'-(2,2'-(1,3-phenylene)bis(propane-2,2-diyl))bis(azanediyl)bis(oxomethylene)bis(oxy)bis(butane-4,1-diyl)diacrylate, 4-(2-(3-(2-((4-acryloyloxy)butoxy)carbonylamino)propan-2-yl)phenyl)propan-2-ylcarbamoylxy)butyl methacrylate, 2,2'-(2,2'-(1,3-phenylene)bis(propane-2,2-diyl))bis(azanediyl)bis(oxomethylene)bis(oxy)bis(3-phenoxypropane-2,1-diyl)bis(2-methacrylate), 2,2'-(2,2'-(1,3-phenylene)bis(propane-2,2-diyl))bis(azanediyl)bis(oxomethylene)bis(oxy)bis(3-phenoxypropane-2,1-diyl)diacrylate, 2-(2-(3-(2-((1-(acryloyloxy)-3-phenoxypropan-2-yloxy)carbonylamino)propan-2-yl)phenyl)propan-2-ylcarbamoylxy)-3-phenoxypropyl methacrylate, 2,2'-(2,2'-(1,3-phenylene)bis(propane-2,2-diyl))bis(azanediyl)bis(oxomethylene)bis(oxy)bis(3-(phenylamino)propane-2,1-diyl)bis(2-methacrylate), 2,2'-(2,2'-(1,3-phenylene)bis(propane-2,2-diyl))bis(azanediyl)bis(oxomethylene)bis(oxy)bis(3-(phenylamino)propane-2,1-diyl)diacrylate, 2-(2-(3-(2-((1-(acryloyloxy)-3-(phenylamino)propan-2-yloxy)carbonylamino)propan-2-yl)phenyl)propan-2-ylcarbamoyloxy)-3-(phenylamino)propyl methacrylate, 2,2'-(2,2'-(1,3-phenylene)bis(propane-2,2-diyl))bis(azanediyl)bis(oxomethylene)bis(oxy)bis(3-(phenylthio)propane-2,1-diyl)bis(2-methylacrylate), 2,2'-(2,2'-(1,3-phenylene)bis(propane-2,2-diyl))bis(azanediyl)bis(oxomethylene)bis(oxy)bis(3-(phenylthio)propane-2,1-diyl) diacrylate, 2-(2-(3-(2-((1-(acryloyloxy)-3-(phenylthio)propan-2-yloxy)carbonylamino)propan-2-yl)phenyl)propan-2-ylcarbamoyloxy)-3-(phenylthio)propyl methacrylate, 2-'-(2,2'-(1,3-phenylene)bis(propane-2,2-diyl))bis(azanediyl)bis(oxomethylene)bis(3-(benzyloxy)propane-2,1-diyl)bis(2-methylacrylate), 2-'-(2,2'-(1,3-phenylene)bis(propane-2,2-diyl))bis(azanediyl)bis(oxomethylene)bis(3-(benzyloxy)propane-2,1-diyl) diacrylate, 2-(2-(3-(2-((1-(acryloyloxy)-3-(benzyloxy)propan-2-yloxy)carbonylamino)propan-2-yl)phenyl)propan-2-ylcarbamoyloxy)-3-(benzyloxy)propyl methacrylate, 2,2'-(2,2'-(1,3-phenylene)bis(propane-2,2-diyl))bis(azanediyl)bis(oxomethylene)bis(oxy)bis(3-(methacryloyloxy)propane-2,1-diyl)dibenzoate, 2,2'-(2,2'-(1,3-phenylene)bis(propane-2,2-diyl))bis(azanediyl)bis(oxomethylene)bis(oxy)bis(3-(acryloyloxy)propane-2,1-diyl)dibenzoate, 2,2'-(2,2'-(1,3-phenylene)bis(propane-2,2-diyl))bis(azanediyl)bis(oxomethylene)bis(oxy)bis(3-(2-phenylacetoxy)propane-2,1-diyl)bis(2-methacrylate), 2,2'-(2,2'-(1,3-phenylene)bis(propane-2,2-diyl))bis(azanediyl)bis(oxomethylene)bis(oxy)bis(3-(2-phenylacetoxy)propane-2,1-diyl)diacrylate, 2-(2-(3-(2-((1-(acryloyloxy)-3-(2-phenylacetoxy)propan-2-yloxy)carbonylamino)propan-2-yl)phenyl)propan-2-ylcarbamoyloxy)-3-(2-phenylacetoxy)propyl methacrylate and the like.

When the silane coupling agent of the embodiments of the present invention is applied to the medical and/or dental curable composition, it is preferable that at least one of a polymerization initiator and a polymerization accelerator is included. Regarding the preferable mixing amount, the mixing amount of the polymerization initiator and the polymerization accelerator is preferably 0.5% by weight to 5% by weight based on the radical polymerizable monomer. When the concentration is lower than 0.5% by weight, the mechanical strength decreases since many unpolymerized radical polymerizable monomers occur. When the concentration is higher than 5% by weight, the degree of polymerization decreases and the mechanical strength decreases.

As the polymerization initiator included in the medical and/or dental curable composition of the embodiments of the present invention, a polymerization initiator selected from a polymerization initiator that have been used in the industrial world can be used. Of these polymerization initiators, a polymerization initiator that has been used for medical and/or dental applications is preferably used. Particularly, a polymerization initiator for photopolymerization and chemical polymerization is used alone or as an appropriate combination of two or more. Specific examples of the photopolymerization initiator among the polymerization initiators included in the medical and/or dental curable composition of the embodiments of the present invention include (bis)acylphosphine oxides, water-soluble acylphosphine oxides, thioxanthones or quaternary ammonium salts of thioxanthones, ketals, α-diketones, coumarins, anthraquinones, benzoinalkyl ether compounds, α-amino ketone-based compounds and the like.

Specific examples of the acylphosphine oxides used as the photopolymerization initiator include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyldi-(2,6-dimethylphenyl)phosphonate and the like. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, bis-(2,6-dimethoxybenzoyl)phenylphosphine oxide, bis-(2,6-dimethoxybenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, (2,5,6-trimethylbenzoyl)-2,4,4-trimethylpentylphosphine oxide and the like.

Specific examples of the thioxanthones or the quaternary ammonium salts of the thioxanthones used as the photopolymerization initiator include thioxanthone, 2-chlorthioxanthen-9-one, 2-hydroxy-3-(9-oxy-9H-thioxanthen-4-yloxy)-N,N,N-trimethyl-propane aluminum chloride, 2-hydroxy-3-(1-methyl-9-oxy-9H-thioxanthen-4-yloxy)-N,N,N-trimethyl-propane aluminum chloride, 2-hydroxy-3-(9-oxo-9H-thioxanthen-2-yloxy)-N,N,N-trimethyl-propane aluminum chloride, 2-hydroxy-3-(3,4-dimethyl-9-oxo-9H-thioxanthen-2-yloxy)-N,N,N-trimethyl-1-propane aluminum chloride, 2-hydroxy-3-(3,4-dimethyl-9H-thioxanthen-2-yloxy)-N,N,N-trimethyl-1-propane aluminum chloride, 2-hydroxy-3-(1,3,4-trimethyl-9-oxo-9H-thioxanthen-2-yloxy)-N,N,N-trimethyl-1-propane aluminum chloride and the like.

Specific examples of the α-diketones used as the photopolymerization initiator include diacetyl, dibenzyl, camphorquinone, 2,3-pentanedione, 2,3-octadione, 9,10- phenanthrenequinone, 4,4'-oxybenzyl, acenaphthenequinone and the like.

Specific examples of the coumarin compounds used as the photopolymerization initiator include compounds such as 3,3'-carbonylbis(7-diethylamino)coumarin, 3-(4-methoxybenzoyl)coumarin, 3-thenoylcoumarin, 3-benzoyl-5,7-dimethoxycoumarin, 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl)coumarin, 3-benzoyl-8-methoxycoumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f]coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f]coumarin, 7-methoxy-3-(p-nitrobenzoyl)coumarin, 3-(p-nitrobenzoyl)coumarin, 3-benzoyl-8-methoxycoumarin, 3-benzoyl-6-nitrocoumarin-3-benzoyl-7-diethylaminocoumarin, 7-dimethylamino-3-(4-methoxybenzoyl)coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f]coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphtho[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazoyl)-7-(diethylamino)coumarin, 3-(2-benzothiazoyl)-7-(dibutylamino)coumarin, 3-(2-benzoimidazolyl)-7-(diethylamino)coumarin, 3-(2-benzothiazoyl)-7-(dioctylamino)coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-1,1,7,7-tetramethyl1H,5H,11H-[1]benzopyrano[6,7,8-ij]quinolizin-1l-one and 10-(2-benzothiazoyl)-2,3,6,7-tetrahydro-1,1,7,7-tetramethyl1H,5H,11H-[1]benzopyrano[6,7,8-ij]quinolizin-11-one.

Of the coumarin compounds, particularly 3,3'-carbonylbis (7-diethylaminocoumarin) and 3,3'-carbonylbis(7-dibutylaminocoumarin) are suitable.

Specific examples of the anthraquinones used as the photopolymerization initiator include anthraquinone, 1-chloroanthraquinone, 2-chloroanthraquinone, 1-bromoanthraquinone, 1,2-benzanthraquinone, 1-methylanthraquinone, 2-ethylanthraquinone, 1-hydroxyanthraquinone and the like.

Specific examples of the benzoinalkyl ethers used as the photopolymerization initiator include benzoinmethyl ether, benzoinethyl ether, benzoinisopropyl ether, benzoinisobutyl ether and the like.

Specific examples of the α-amino ketones used as the photopolymerization initiator include 2-methyl-1-[4-(methylthio)phenyl]-2-morpholinopropan-1-one and the like.

Of the photopolymerization initiators, at least one selected from the group consisting of (bis)acylphosphine oxides and salts thereof, α-diketones and coumarin compounds is preferably used. As a result of this, a composition having excellent photocurability at visible and near-ultraviolet regions and that exhibits sufficient photocurability even when any light source of a halogen ramp, light-emitting diode (LED) and a xenon ramp is used.

As the chemical polymerization initiator among the polymerization initiators included in the medical and/or dental curable composition of the embodiments of the present invention, an organic peroxide is preferably used. The above-mentioned organic peroxide used in the chemical polymerization initiator is not particularly limited, and a known organic peroxide can be used. Examples of the representative organic peroxide include ketone peroxide, hydroperoxide, diacyl peroxide, dialkyl peroxide, peroxyketal, peroxy ester, peroxydicarbonate and the like.

Specific examples of the ketone peroxide used as the chemical polymerization initiator include methyl ethyl ketone peroxide, methyl isobutyl ketone peroxide, methylcyclohexanone peroxide and cyclohexanone peroxide and the like.

Specific examples of the hydroperoxide used as the chemical polymerization initiator include 2,5-dimethylhexane-2,5-dihydroperoxide, diisopropylbenzene hydroperoxide, cumene hydroperoxide, t-butyl hydroperoxide and 1,1,3,3-tetramethyl butyl hydroperoxide and the like.

Specific examples of the diacyl peroxide used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide and lauroyl peroxide and the like.

Specific examples of the dialkyl peroxide used as the chemical polymerization initiator include di-t-butyl peroxide, dicumyl peroxide, t-butylcumyl peroxide, 2,5-dimethyl-2,5-di(t-butylperoxy)hexane, 1,3-bis(t-butylperoxyisopropyl)benzene and 2,5-dimethyl-2,5-di(t-butylperoxy)-3-hexyne and the like.

Specific examples of the peroxyketal used as the chemical polymerization initiator include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane and 4,4-bis(t-butylperoxy)valeric acid-n-butyl ester and the like.

Specific examples of the peroxy ester used as the chemical polymerization initiator include α-cumylperoxyneodecanoate, t-butylperoxyneodecanoate, t-butylperoxypivalate, 2,2,4-trimethylpentylperoxy-2-ethylhexanoate, t-amylperoxy-2-ethylhexanoate, t-butylperoxy-2-ethylhexanoate, di-t-butylperoxyisophthalate, di-t-butylperoxyhexahydroterephthalate, t-butylperoxy-3,3,5-trimethylhexanoate, t-butylperoxyacetate, t-butylperoxybenzoate and t-butylperoxymaleic acid and the like.

Specific examples of the peroxydicarbonate used as the chemical polymerization initiator include di-3-methoxyperoxydicarbonate, di-2-ethylhexylperoxydicarbonate, bis(4-t-butylcyclohexyl)peroxydicarbonate, diisopropylperoxydicarbonate, di-n-propylperoxydicarbonate, di-2-ethoxyethylperoxydicarbonate and diallylperoxydicarbonate and the like.

Of the organic peroxides, diacyl peroxides are preferably used, and of the diacyl peroxides, benzoyl peroxides are particularly preferably used in terms of the comprehensive balance between safety, storage stability and radical formation ability.

Specific examples of the polymerization accelerator include amines, sulfinic acids and salts thereof, borate compounds, barbituric acid derivatives, triazine compounds, copper compounds, tin compounds, vanadium compounds, halogen compounds, aldehydes, thiol compounds and the like.

Amines used as the polymerization accelerator are divided into aliphatic amines and aromatic amines. Specific examples of the aliphatic amines include primary aliphatic amines such as n-butylamine, n-hexylamine and n-octylamine, secondary aliphatic amines such as diisopropylamine, dibutylamine and N-methyldiethanolamine, tertiary aliphatic amines such as N-methylethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine and tributylamine and the like. Of these amines, tertiary aliphatic amines are preferable, and of these tertiary aliphatic amines, N-methyldiethanolamine and triethanolamine are more preferably used in terms of the curability and the storage stability of the composition.

Specific examples of the aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, 4-N,N-dimethylaminobenzoic acid ethyl ester, 4-N,N-dimethylaminobenzoic acid methyl ester, N,N-dimethylaminobenzoic acid-n-butoxyethyl ester, 4-N,N-dimethylaminobenzoic acid-2-(methacryloyloxy)ethyl ester, 4-N,N-dimethylaminobenzophenone, 4-dimethylaminobenzoic acid butyl and the like. Of these aromatic amines, N,N-di(2-hydroxyethyl)-p-toluidine, 4-N,N-dimethylaminobenzoic acid ethyl ester, N,N-dimethylaminobenzoic acid-n-butoxyethyl ester and 4-N,N-dimethylaminobenzophenone and the like are exemplified in terms of capable of imparting excellent curability to the composition.

Specific examples of the sulfinic acids and salts thereof used as the polymerization accelerator include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, calcium 2,4,6-triisopropylbenzenesulfinate and the like, and benzenesulfinate sodium, p-toluenesulfinate sodium and 2,4,6-triisopropylbenzenesulfinate sodium are particularly preferable.

Regarding the borate compounds used as the polymerization accelerator, specific examples of the borate compounds having one aryl group in one molecule include sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts and butylquinolinium salts and the like of trialkylphenylboron, trialkyl(p-chlorophenyl)boron, trialkyl(p-phlorophenyl)boron, trialkyl(3,5-bistriphloromethyl)phenylboron, trialkyl[3,5-bis(1,1,1,3,3,3-hexaphloro-2-methoxy-2-propyl)phenyl]boron, trialkyl(p-nitrophenyl)boron, trialkyl(m-nitrophenyl)boron, trialkyl(p-butylphenyl)boron, trialkyl(m-butylphenyl)boron, trialkyl(p-butyloxyphenyl)boron, trialkyl(m-butyloxyphenyl)boron, trialkyl(p-octyloxyphenyl)boron and trialkyl(m-octyloxyphenyl)boron (the alkyl group is at least one selected from the group consisting of an n-butyl group, an n-octyl group and an n-dodecyl group and the like).

Specific examples of the borate compounds having two aryl groups in one molecule include sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts and butylquinolinium salts and the like of dialkyldiphenylboron, dialkyldi(p-chlorophenyl)boron, dialkyldi(p-phlorophenyl)boron, dialkyldi(3,5-bistriphloromethyl)phenylboron, dialkyldi[3,5-bis(1,1,1,3,3,3-hexaphloro-2-methoxy-2-propyl)phenyl]boron, dialkyldi(p-nitrophenyl)boron, dialkyldi(m-nitrophenyl)boron, dialkyldi(p-butylphenyl)boron, dialkyldi(m-butylphenyl)boron, dialkyldi(p-butyloxyphenyl)boron, dialkyldi(m-butyloxyphenyl)boron, dialkyldi(p-octyloxyphenyl)boron and dialkyldi(m-octyloxyphenyl)boron (the alkyl group is at least one selected from the group consisting of an n-butyl group, an n-octyl group and an n-dodecyl group and the like).

Furthermore, specific examples of the borate compounds having three aryl groups in one molecule include sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts, butylquinolinium salts and the like of monoalkyltriphenylboron, monoalkyltri(p-chlorophenyl)boron, monoalkyltri(p-phlorophenyl)boron, monoalkyltri(3,5-bistriphloromethyl)phenylboron, monoalkyltri[3,5-bis(1,1,1,3,3,3-hexaphloro-2-methoxy-2-propyl)phenyl]boron, monoalkyltri(p-nitrophenyl)boron, monoalkyltri(m-nitrophenyl)boron, monoalkyltri(p-butylphenyl)boron, monoalkyltri(m-butylphenyl)boron, monoalkyltri(p-butyloxyphenyl)boron, monoalkyltri(m-butyloxyphenyl)boron, monoalkyltri(p-octyloxyphenyl)boron and monoalkyltri(m-octyloxyphenyl)boron (the alkyl group is at least one selected from an n-butyl group, an n-octyl group or an n-dodecyl group or the like).

Furthermore, specific examples of the borate compounds having four aryl groups in one molecule include sodium salts, lithium salts, potassium salts, magnesium salts, tetrabutylammonium salts, tetramethylammonium salts, tetraethylammonium salts, methylpyridinium salts, ethylpyridinium salts, butylpyridinium salts, methylquinolinium salts, ethylquinolinium salts and butylquinolinium salts and the like of tetraphenylboron, tetrakis(p-chlorophenyl)boron, tetrakis(p-phlorophenyl)boron, tetrakis(3,5-bistriphloromethyl)phenylboron, tetrakis[3,5-bis(1,1,1,3,3,3-hexaphloro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis(p-butyloxyphenyl)boron, tetrakis(m-butyloxyphenyl)boron, tetrakis(p-octyloxyphenyl)boron, tetrakis(m-octyloxyphenyl)boron, (p-phlorophenyl)triphenylboron, (3,5-bistriphloromethyl)phenyltriphenylboron, (p-nitrophenyl)triphenylboron, (m-butyloxyphenyl)triphenylboron, (p-butyloxyphenyl)triphenylboron, (m-octyloxyphenyl)triphenylboron and (p-octyloxyphenyl)triphenylboron.

Of these arylborate compounds, borate compounds having three or four aryl groups in one molecule are preferably used in terms of storage stability. These arylborate compounds may be used as one or a mixture of two or more.

Specific examples of the barbituric acid derivatives used as the polymerization accelerator include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethylbarbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methylbarbituric acid, 5-propylbarbituric acid, 1,5-diethylbarbituric acid, 1-ethyl-5-methylbarbituric acid, 1-ethyl-5-isobutylbarbituric acid, 1,3-diethyl-5-butylbarbituric acid, 1-cyclohexyl-5-methylbarbituric acid, 1-cyclohexyl-5-ethylbarbituric acid, 1-cyclohexyl-5-octylbarbituric acid, 1-cyclohexyl-5-hexylbarbituric acid, 5-butyl-1-cyclohexylbarbituric acid, 1-benzyl-5-phenylbarbituric acid and thiobarbituric acids, and salts thereof (particularly alkali metals or alkaline earth metals are preferable). Examples of the salts of these barbituric acids include sodium 5-butylbarbiturate, sodium 1,3,5-trimethylbarbiturate and sodium 1-cyclohexyl-5-ethylbarbiturate and the like.

Specific examples of particularly suitable barbituric acid derivatives include 5-butylbarbituric acid, 1,3,5-trimethylbarbituric acid, 1-cyclohexyl-5-ethylbarbituric acid, 1-benzyl-5-phenylbarbituric acid, and sodium salts of these barbituric acids and the like.

Specific examples of the triazine compounds used as the polymerization accelerator include 2,4,6-tris(trichloromethyl)-s-triazine, 2,4,6-tris(tribromomethyl)-s-triazine, 2-methyl-4,6-bis(trichloromethyl)-s-triazine, 2-methyl-4,6-bis(tribromomethyl)-s-triazine, 2-phenyl-4,6-bis(trichloromethyl)-s-triazine, 2-(p-methoxyphenyl)-4,6-bis(trichloromethyl)-s-triazine, 2-(p-methylthiophenyl)-4,6-bis(trichloromethyl)-s-triazine, 2-(p-chlorophenyl)-4,6-bis(trichloromethyl)-s-triazine, 2-(2,4-dichlorophenyl)-4,6-bis(trichloromethyl)-s-triazine, 2-(p-bromophenyl)-4,6-bis(trichloromethyl)-s-triazine, 2-(p-tolyl)-4,6-bis(trichloromethyl)-s-triazine, 2-n-propyl-4,6-bis(trichloromethyl)-s-triazine, 2-($\alpha,\alpha,\beta$-trichloroethyl)-4,6-bis(trichloromethyl)-s-triazine, 2-styryl-4,6-bis(trichloromethyl)-s-triazine, 2-[2-(p-methoxyphenyl)ethenyl]-4,6-bis(trichloromethyl)-s-triazine, 2-[2-(o-methoxyphenyl)ethenyl]-4,6-bis(trichloromethyl)-s-triazine, 2-[2-(p-butoxyphenyl)ethenyl]-4,6-bis(trichloromethyl)-s-triazine, 2-[2-(3,4-dimethoxyphenyl)ethenyl]-4,6-bis(trichloromethyl)-s-triazine, 2-[2-(3,4,5-trimethoxyphenyl)ethenyl]-4,6-bis(trichloromethyl)-s-triazine, 2-(1-naphthyl)-4,6-bis(trichloromethyl)-s-triazine, 2-(4-biphenylyl)-4,6-bis(trichloromethyl)-s-triazine, 2-[2-{N,N-bis(2-hydroxyethyl)amino}ethoxy]-4,6-bis(trichloromethyl)-s-triazine, 2-[2-{N-hydroxyethyl-N-ethylamino}ethoxy]-4,6-bis(trichloromethyl)-s-triazine, 2-[2-{N-hydroxyethyl-N-methylamino}ethoxy]-4,6-bis(trichloromethyl)-s-triazine, 2-[2-{N,N-diallylamino}ethoxy]-4,6-bis(trichloromethyl)-s-triazine and the like.

Of the triazine compounds exemplified above, particularly preferable triazine compounds include 2,4,6-tris(trichloromethyl)-s-triazine in terms of polymerization activity and 2-phenyl-4,6-bis(trichloromethyl)-s-triazine, 2-(p-chlorophenyl)-4,6-bis(trichloromethyl)-s-triazine and 2-(4-biphenylyl)-4,6-bis(trichloromethyl)-s-triazine in terms of storage stability. The above-mentioned triazine compounds may be used as one or a mixture of two or more.

Specific examples of the copper compounds used as the polymerization accelerator include acetylacetone copper, cupric acetate, copper oleinate, cupric chloride, cupric bromide and the like.

Specific examples of the tin compounds used as the polymerization accelerator include di-n-butyltin dimaleate, di-n-octyltin dimaleate, di-n-octyltin dilaurate, di-n-butyltin dilaurate and the like. Particularly suitable tin compounds include di-n-octyltin dilaurate and di-n-butyltin dilaurate.

The vanadium compounds used as the polymerization accelerator are preferably tetravalent and/or pentavalent vanadium compounds. Specific examples of the tetravalent and/or pentavalent vanadium compounds include vanadium (IV) oxide, vanadium(IV) oxide acetylacetonate, vanadyl (IV) oxalate, vanadyl(IV) sulfate, oxobis(1-phenyl-1,3-butanedionate)vanadium(IV), bis(maltolato)oxovanadium (IV), vanadium(V) oxide, sodium metavanadate(V), ammonium metavanadate(V) and the like.

Specific examples of the halogen compounds used as the polymerization accelerator include dilauryldimethylammonium chloride, lauryldimethylbenzylammonium chloride, benzyltrimethylammonium chloride, tetramethylammonium chloride, benzyldimethylcetylammonium chloride, dilauryldimethylammonium bromide and the like.

Specific examples of the aldehydes used as the polymerization accelerator include terephthalaldehyde and benzaldehyde derivatives and the like. Examples of the benzaldehyde derivatives include dimethylaminobenzaldehyde, p-methyloxybenzaldehyde, p-ethyloxybenzaldehyde, p-n-octyloxybenzaldehyde and the like. Of these benzaldehyde derivatives, p-n-octyloxybenzaldehyde is preferably used in terms of curability.

Specific examples of the thiol compounds used as the polymerization accelerator include 3-mercaptopropyltrimethoxysilane, 2-mercaptobenzooxazole, decanethiol, thiobenzoic acid and the like.

Components that can be included in the medical and/or dental curable composition of the embodiments of the present invention is optional, and specific examples thereof include colorants such as dyes and pigments, thickeners, aromatics and the like.

EXAMPLES

A method for producing a silane coupling agent and a method for preparing a medical and/or dental curable composition comprising the same of the present invention, and physical properties will be described in detail below, but the present invention is in no way limited to the description thereof.

Synthesis Examples and Comparative Synthesis Examples (Synthesis Example 1-I) Synthesis of Silane Coupling Agent 1-I Having a Radical Polymerizable Group In a four-necked flask (volume of 100 mL) equipped with stirring blades, a thermometer, a dropping funnel and a condenser tube, 17.0 g (0.10 mol) of 10-undecen-1-ol, 36.9 mg (corresponding to 1,000 ppm) of dibutyltin(IV) dilaurate and 18.5 mg (corresponding to 500 ppm) of p-methoxyphenol were charged and dissolved. Subsequently, 19.9 g (0.10 mol) of 2-(2-isocyanatoethoxy)ethyl methacrylate was weighed in the dropping funnel. The four-necked flask was immersed in an oil bath heated to 75° C., 2-(2-isocyanatoethoxy)ethyl methacrylate was added dropwise while stirring so that the inner temperature did not exceed 80° C. After completion of the dropwise addition, the reaction was continued for 5 hours while maintaining the temperature of the oil bath, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 10-undecen-1-ol and 2-(2-isocyanatoethoxy)ethyl methacrylate as raw materials disappeared, and a new peak of 2-(2-(((undec-10-en-1-yloxy)carbonyl)amino)ethoxy)ethyl methacrylate (molecular weight of 369.5) was confirmed. As a result of the FT-IR measurement, the isocyanate absorption at 2,280 to 2,250 $cm^{-1}$ and the disappearance of the hydroxy group absorption at around 3,300 $cm^{-1}$ were confirmed, and the absorption attributed to a urethane group was newly confirmed at 1,250 $cm^{-1}$. Subsequently, in a four-necked flask (volume of 100 mL) equipped with stirring blades, a thermometer, a dropping funnel and a condenser tube, 37.0 g (0.10 mol) of a precursor compound synthesized by the above-mentioned operation and 5.3 mg (corresponding to 100 ppm) of platinum(0)-1,3-divinyl-1,1,3,3-tetramethyldisiloxane were added, followed by sufficient stirring so as to obtain a uniform mixture. Separately, 16.4 g (0.10 mol) of triethoxysilane was weighed in the dropping funnel. Triethoxysilane was added dropwise while stirring the four-necked flask at room temperature so that the inner temperature did not exceed 35° C. After completion of the dropwise addition, the reaction was continued at room temperature for 12 hours, leading to aging. After completion of the aging, HPLC and FT-IR measurements were performed. As a result of the HPLC measurement, peaks of 2-(2-(((undec-10-en-1-yloxy)carbonyl)amino)ethoxy)ethyl methacrylate and triethoxysilane as raw materials disappeared, and new peak of 4,4-diethoxy-17-oxo-3,16,21-trioxa-18-aza-4-silatricosan-23-yl methacrylate (molecular weight of 533.78) was confirmed. As a result of the FT-IR measurement, the disappearance of the silane group absorption at 2,190 $cm^{-1}$ was confirmed. The chemical structure of the compound synthesized in the present Synthesis Example is mentioned below.

ppm) and p-methoxyphenol: 20.7 mg (corresponding to 500 ppm) were charged and dissolved. Subsequently, 24.3 g (0.10 mol) of 2-(2-(2-isocyanatoethoxy)ethoxy)ethyl methacrylate was weighed in the dropping funnel. The four-necked flask was immersed in an oil bath heated to 75° C. and 2-(2-(2-isocyanatoethoxy)ethoxy)ethyl methacrylate was added dropwise while stirring so that the inner temperature did not exceed 80° C. After completion of the dropwise addition, the reaction was continued while maintaining the temperature of an oil bath for 5 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 10-undecen-1-ol and 2-(2-(2-isocyanatoethoxy)ethoxy)ethyl methacrylate as raw materials disappeared, and new peak of 10-oxo-3,6,11-trioxa-9-azadocos-21-en-1-yl methacrylate (molecular weight of 413.55) was confirmed. As a result of the FT-IR measurement, the isocyanate absorption at 2,280 to 2,250 $cm^{-1}$ and the disappearance of the hydroxy group absorption at around 3,300 $cm^{-1}$ were confirmed, and the absorption attributed to a urethane group was newly confirmed at 1,250 $cm^{-1}$. Subsequently, in a four-necked flask (volume of 200 mL) equipped with stirring blades, a thermometer, a dropping funnel and a condenser tube, 41.4 g (0.10 mol) of the precursor compound synthesized by the above-mentioned operation and 5.8 mg (corresponding to 100 ppm) of platinum(0)-1,3-divinyl-1,1,3,3-tetramethyldisiloxane were added, followed by sufficient stirring so as to obtain a uniform mixture. Separately, 16.4 g (0.10 mol) of triethoxysilane was weighed in the dropping funnel. In the four-necked flask, triethoxysilane was added dropwise at room temperature while stirring so that the inner temperature did not exceed 35° C. After completion of the dropwise addition, the reaction was continued at room temperature for 12 hours, leading to aging. After completion of the aging, HPLC and FT-IR measurements were performed. As a result of the HPLC measurement, peaks of 10-oxo-3,6,11-trioxa-9-azadocos-21-en-1-yl

[Chemical Formula 9]

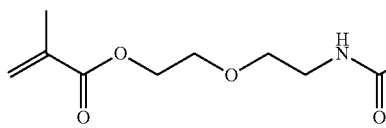 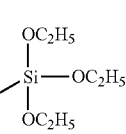

(Synthesis Example 2-I) Synthesis of Silane Coupling Agent 2-I Having a Radical Polymerizable Group In a four-necked flask (volume of 100 mL) equipped with stirring blades, a thermometer, a dropping funnel and a condenser tube, 17.0 g (0.10 mol) of 10-undecen-1-ol, dibutyltin(IV) dilaurate: 41.3 mg (corresponding to 1,000 methacrylate and triethoxysilane as raw materials disappeared, and new peak of 4,4-diethoxy-17-oxo-3,16,21,24-tetraoxa-18-aza-4-silahexacosan-26-yl methacrylate (molecular weight of 577.83) was confirmed. As a result of the FT-IR measurement, the disappearance of the silane group absorption at 2,190 $cm^{-1}$ was confirmed. The chemical structure of the compound synthesized in the present Synthesis Example is mentioned below.

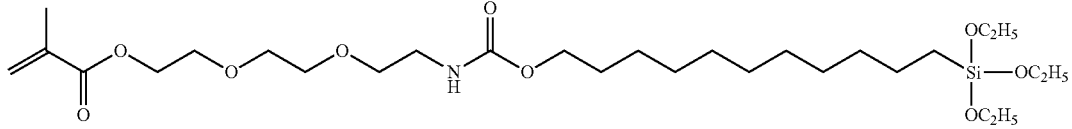

(Synthesis Example 3-I) Synthesis of Silane Coupling Agent 3-I Having a Radical Polymerizable Group In a four-necked flask (volume of 100 mL) equipped with stirring blades, a thermometer, a dropping funnel and a condenser tube, 17.0 g (0.10 mol) of 10-undecen-1-ol, 41.3 mg (corresponding to 1,000 ppm) of dibutyltin(IV) dilaurate and 20.7 mg (corresponding to 500 ppm) of p-methoxyphenol were charged and dissolved. Subsequently, 28.7 g (0.10 mol) of 2-(2-(2-(2-isocyanatoethoxy)ethoxy)ethoxy)ethyl methacrylate was weighed in the dropping funnel. The four-necked flask was immersed in an oil bath heated to 75° C., and 2-(2-(2-(2-isocyanatoethoxy)ethoxy)ethoxy)ethyl methacrylate added dropwise while stirring so that the inner temperature did not exceed 80° C. After completion of the dropwise addition, the reaction was continued while maintaining the temperature of an oil bath for 5 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 10-undecen-1-ol and 2-(2-(2-(2-isocyanatoethoxy)ethoxy)ethoxy)ethyl methacrylate as raw materials disappeared, and new peak of 13-oxo-3,6,9,14-tetraoxa-12-azapentacos-24-en-1-ylmethacrylate (molecular weight of 457.61) was confirmed. As a result of the FT-IR measurement, the isocyanate absorption at 2,280 to 2,250 cm$^{-1}$ and the disappearance of the hydroxy group absorption at around 3,300 cm$^{-1}$ were confirmed, and the absorption attributed to a urethane group was newly confirmed at 1,250 cm$^{-1}$. Subsequently, in a four-necked flask (volume of 200 mL) equipped with stirring blades, a thermometer, a dropping funnel and a condenser tube, 45.8 g (0.10 mol) of the precursor compound synthesized by the above-mentioned operation and 6.2 mg (corresponding to 100 ppm) of platinum(0)-1,3-divinyl-1,1,3,3-tetramethyldisiloxane were added, followed by sufficient stirring so as to obtain a uniform mixture. Separately, 16.4 g (0.10 mol) of triethoxysilane was weighed in the dropping funnel. In the four-necked flask, triethoxysilane was added dropwise at room temperature while stirring so that the inner temperature did not exceed 35° C. After completion of the dropwise addition, the reaction was continued at room temperature for 12 hours, leading to aging. After completion of the aging, HPLC and FT-IR measurements were performed. As a result of the HPLC measurement, peaks of 13-oxo-3,6,9,14-tetraoxa-12-azapentacos-24-en-1-ylmethacrylate and triethoxysilane as raw materials disappeared, and new peak of 4,4-diethoxy-17-oxo-3,16,21,24,27-pentaoxa-18-aza-4-silanonacosan-29-yl methacrylate (molecular weight of 621.88) was confirmed. As a result of the FT-IR measurement, the disappearance of the silane group absorption at 2,190 cm$^{-1}$ was confirmed. The chemical structure of the compound synthesized in the present Synthesis Example is mentioned below.

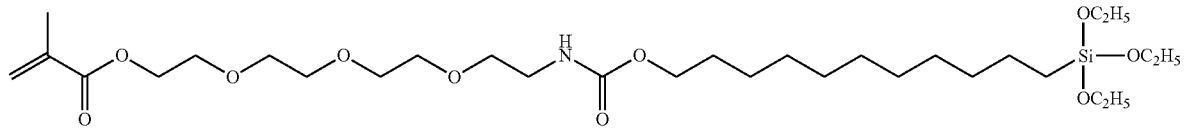

(Synthesis Example 4-I) Synthesis of Silane Coupling Agent 4-I Having a Radical Polymerizable Group In a four-necked flask (volume of 100 mL) equipped with stirring blades, a thermometer, a dropping funnel and a condenser tube, 11.4 g (0.10 mol) of hept-6-en-1-ol, 31.3 mg (corresponding to 1,000 ppm) of dibutyltin(IV) dilaurate and 15.7 mg (corresponding to 500 ppm) of p-methoxyphenol were charged and dissolved. Subsequently, 19.9 g (0.10 mol) of 2-(2-isocyanatoethoxy)ethyl methacrylate weighed in the dropping funnel. The four-necked flask was immersed in an oil bath heated to 75° C., and 2-(2-isocyanatoethoxy)ethyl methacrylate was added dropwise while stirring so that the inner temperature did not exceed 80° C. After completion of the dropwise addition, the reaction was continued while maintaining the temperature of an oil bath for 5 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of hept-6-en-1-ol and 2-(2-isocyanatoethoxy)ethyl methacrylate as raw materials disappeared, and new peak of 2-(2-(((hept-6-en-1-yloxy)carbonyl)amino)ethoxy)ethyl methacrylate (molecular weight of 313.39) was confirmed. As a result of the FT-IR measurement, the isocyanate absorption at 2,280 to 2,250 cm$^{-1}$ and the disappearance of the hydroxy group absorption at around 3,300 cm$^{-1}$ were confirmed, and the absorption attributed to a urethane group was newly confirmed at 1,250 cm$^{-1}$. Subsequently, in a four-necked flask (volume of 200 mL) equipped with stirring blades, a thermometer, a dropping funnel and a condenser tube, 31.3 g (0.10 mol) of the precursor compound synthesized by the above-mentioned operation and 4.8 mg (corresponding to 100 ppm) of platinum(0)-1,3-divinyl-1,1,3,3-tetramethyldisiloxane were added, followed by sufficient stirring so as to obtain a uniform mixture. Separately, 16.4 g (0.10 mol) of triethoxysilane was weighed in the dropping funnel. In the four-necked flask, triethoxysilane was added dropwise at room temperature while stirring so that the inner temperature did not exceed 35° C. After completion of the dropwise addition, the reaction was continued at room temperature for 12 hours, leading to aging. After completion of the aging, HPLC and FT-IR measurements were performed. As a result of the HPLC measurement, peaks of 2-(2-(((hept-6-en-1-yloxy) carbonyl)amino)ethoxy)ethyl methacrylate and triethoxysilane as raw materials disappeared, and new peak of 4,4-diethoxy-13-oxo-3,12,17-trioxa-14-aza-4-silanonadecan-19-yl methacrylate (molecular weight of 477.67) was confirmed. As a result of the FT-IR measurement, the disappearance of the silane group absorption at 2,190 cm$^{-1}$ was confirmed. The chemical structure of the compound synthesized in the present Synthesis Example is mentioned below.

new peak of 2-(2-(((pent-4-en-1-yloxy)carbonyl)amino) ethoxy)ethyl methacrylate (molecular weight of 285.34) was confirmed. As a result of the FT-IR measurement, the isocyanate absorption at 2,280 to 2,250 cm$^{-1}$ and the disappearance of the hydroxy group absorption at around 3,300 cm$^{-1}$ were confirmed, and the absorption attributed to a urethane group was newly confirmed at 1,250 cm$^{-1}$. Subsequently, in a four-necked flask (volume of 100 mL) equipped with stirring blades, a thermometer, a dropping funnel and a condenser tube, 28.5 g (0.10 mol) of the precursor compound synthesized by the above-mentioned operation and 4.5 mg (corresponding to 100 ppm) of platinum(0)-1,3-divinyl-1,1,3,3-tetramethyldisiloxane were added, followed by sufficient stirring so as to obtain a uniform mixture. Separately, 16.4 g (0.10 mol) of triethoxysilane was weighed in the dropping funnel. In the four-necked flask, triethoxysilane was added dropwise at room temperature while stirring so that the inner temperature did not exceed 35° C. After completion of the dropwise addition, the reaction was continued at room temperature for 12 hours, leading to aging. After completion of the aging, HPLC and FT-IR measurements were performed. As a result of the HPLC measurement, peaks of 2-(2-(((pent-4-en-1-yloxy) carbonyl)amino)ethoxy)ethyl methacrylate and triethoxysilane as raw materials disappeared, and new peak of 4,4-diethoxy-11-oxo-3,10,15-trioxa-12-aza-4-silaheptadecan-17-yl methacrylate (molecular weight of 449.62) was confirmed. As a result of the FT-IR measurement, the disappearance of the silane group absorption at 2,190 cm$^{-1}$

[Chemical Formula 12]

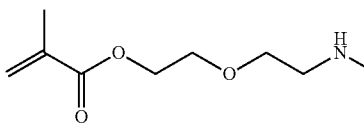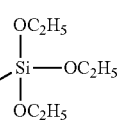

(Synthesis Example 5-I) Synthesis of Silane Coupling Agent 5-I Having a Radical Polymerizable Group In a four-necked flask (volume of 100 mL) equipped with stirring blades, a thermometer, a dropping funnel and a condenser tube, 8.6 g (0.10 mol) of pent-4-en-1-ol, 36.9 mg (corresponding to 1,000 ppm) of dibutyltin(IV) dilaurate and 18.5 mg (corresponding to 500 ppm) of p-methoxyphenol were charged and dissolved. Subsequently, 19.9 g (0.10 mol) of 2-(2-isocyanatoethoxy)ethyl methacrylate was weighed in the dropping funnel. The four-necked flask was immersed in an oil bath heated to 75° C., and 2-(2-isocyanatoethoxy) ethyl methacrylate was added dropwise while stirring so that the inner temperature did not exceed 80° C. After completion of the dropwise addition, the reaction was continued while maintaining the temperature of an oil bath for 5 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of pent-4-en-1-ol and 2-(2-isocyanato-ethoxy)ethyl methacrylate as raw materials disappeared, and was confirmed. The chemical structure of the compound synthesized in the present Synthesis Example is mentioned below.

[Chemical Formula 13]

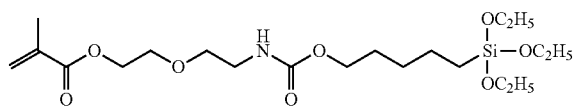

(Synthesis Example 6-I) Synthesis of Silane Coupling Agent 6-I Having a Radical Polymerizable Group In a four-necked flask (volume of 100 mL) equipped with stirring blades, a thermometer, a dropping funnel and a condenser tube, 5.8 g (0.10 mol) of prop-2-en-1-ol, 25.7 mg (corresponding to 1,000 ppm) of dibutyltin(IV) dilaurate and 12.9 mg (corresponding to 500 ppm) of p-methoxyphenol were charged and dissolved. Subsequently, 19.9 g (0.10 mol) of 2-(2-isocyanatoethoxy)ethyl methacrylate was weighed in the dropping funnel. The four-necked flask was immersed in an oil bath heated to 75° C., and 2-(2-isocyanatoethoxy) ethyl methacrylate was added dropwise while stirring so that the inner temperature did not exceed 80° C. After completion of the dropwise addition, the reaction was continued while maintaining the temperature of an oil bath for 5 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of prop-2-en-1-ol and 2-(2-isocyanatoethoxy)ethyl methacrylate as raw materials disappeared, and new peak of 2-(2-(((allyloxy)carbonyl)amino)ethoxy)ethyl methacrylate (molecular weight of 257.29) was confirmed. As a result of the FT-IR measurement, the isocyanate absorption at 2,280 to 2,250 cm$^{-1}$ and the disappearance of the hydroxy group absorption at around 3,300 cm$^{-1}$ were confirmed, and the absorption attributed to a urethane group was newly confirmed at 1,250 cm$^{-1}$. Subsequently, in a four-necked flask (volume of 100 mL) equipped with stirring blades, a thermometer, a dropping funnel and a condenser tube, 25.7 g (0.10 mol) of the precursor compound synthesized by the above-mentioned operation and 4.2 mg (corresponding to 100 ppm) of platinum(0)-1,3-divinyl-1,1,3,3-tetramethyldisiloxane were added, followed by sufficient stirring so as to obtain a uniform mixture. Separately, 16.4 g (0.10 mol) of triethoxysilane was weighed in the dropping funnel. In the four-necked flask, triethoxysilane was added dropwise at room temperature while stirring so that the inner temperature did not exceed 35° C. After completion of the dropwise addition, the reaction was continued at room temperature for 12 hours, leading to aging. After completion of the aging, HPLC and FT-IR measurements were performed. As a result of the HPLC measurement, peaks of 2-(2-(((allyloxy)carbonyl)amino)ethoxy)ethyl methacrylate and triethoxysilane disappeared, and new peak of 4,4-diethoxy-9-oxo-3,8,13-trioxa-10-aza-4-silapentadecan-15-yl methacrylate (molecular weight of 421.56) was confirmed. As a result of the FT-IR measurement, the disappearance of the silane group absorption at 2,190 cm$^{-1}$ was confirmed. The chemical structure of the compound synthesized in the present Synthesis Example is mentioned below.

[Chemical Formula 14]

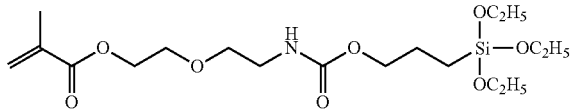

(Synthesis Example 7-I) Synthesis of Silane Coupling Agent 7-I Having a Radical Polymerizable Group In a four-necked flask (volume of 100 mL) equipped with stirring blades, a thermometer, a dropping funnel and a condenser tube, 5.8 g (0.10 mol) of prop-2-en-1-ol, 30.1 mg (corresponding to 1,000 ppm) of dibutyltin(IV) dilaurate and 15.1 mg (corresponding to 500 ppm) of p-methoxyphenol were charged and dissolved. Subsequently, 24.3 g (0.10 mol) of 2-(2-(2-isocyanatoethoxy)ethoxy)ethyl methacrylate was weighed in the dropping funnel. The four-necked flask was immersed in an oil bath heated to 75° C., and 2-(2-(2-isocyanatoethoxy)ethoxy)ethyl methacrylate was added dropwise while stirring so that the inner temperature did not exceed 80° C. After completion of the dropwise addition, the reaction was continued while maintaining the temperature of an oil bath for 5 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of prop-2-en-1-ol and 2-(2-(2-isocyanatoethoxy)ethoxy)ethyl methacrylate as raw materials disappeared, and new peak of 10-oxo-3,6,11-trioxa-9-azatetradec-13-en-1-yl methacrylate (molecular weight of 301.34) was confirmed. As a result of the FT-IR measurement, the isocyanate absorption at 2,280 to 2,250 cm$^{-1}$ and the disappearance of the hydroxy group absorption at around 3,300 cm$^{-1}$ were confirmed, and the absorption attributed to a urethane group was newly confirmed at 1,250 cm$^{-1}$. Subsequently, in a four-necked flask (volume of 100 mL) equipped with stirring blades, a thermometer, a dropping funnel and a condenser tube, 30.1 g (0.10 mol) of the precursor compound synthesized by the above-mentioned operation and 4.7 mg (corresponding to 100 ppm) of platinum(0)-1,3-divinyl-1,1,3,3-tetramethyldisiloxane were added, followed by sufficient stirring so as to obtain a uniform mixture. Separately, 16.4 g (0.10 mol) of triethoxysilane was weighed in the dropping funnel. In the four-necked flask, triethoxysilane was added dropwise at room temperature while stirring so that the inner temperature did not exceed 35° C. After completion of the dropwise addition, the reaction was continued at room temperature for 12 hours, leading to aging. After completion of the aging, HPLC and FT-IR measurements were performed. As a result of the HPLC measurement, peaks of 10-oxo-3,6,11-trioxa-9-azatetradec-13-en-1-yl methacrylate and triethoxysilane as raw materials disappeared, and new peak of 4,4-diethoxy-9-oxo-3,8,13,16-tetraoxa-10-aza-4-silaoctadecan-18-yl methacrylate (molecular weight of 465.61) was confirmed. As a result of the FT-IR measurement, the disappearance of the silane group absorption at 2,190 cm$^{-1}$ was confirmed. The chemical structure of the compound synthesized in the present Synthesis Example is mentioned below.

[Chemical Formula 15]

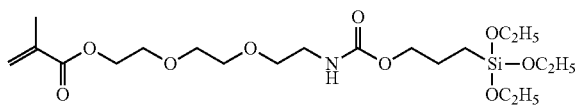

(Synthesis Example 1-II) Synthesis of Silane Coupling Agent 1-II Having a Radical Polymerizable Group In a four-necked flask (volume of 1 L) equipped with stirring blades, a thermometer, a dropping funnel and a condenser tube, 300 mL of tetrahydrofuran, 19.4 g (0.10 mol) of 2,2'-((oxybis(ethane-2,1-diyl))bis(oxy))bis(ethan-1-ol), 27.2 mg of dibutyltin(IV) dilaurate and 13.6 mg of p-methoxyphenol were charged and dissolved. Subsequently, 7.76 g (0.05 mol) of 2-isocyanatoethyl methacrylate was weighed in a beaker and 150 mL of tetrahydrofuran was added, followed by sufficient stirring and further liquid transfer to the dropping funnel. The four-necked flask was immersed in an oil bath heated to 75° C. and 2-isocyanatoethyl methacrylate was added dropwise so as not to cause boiling of tetrahydrofuran. After completion of the dropwise addition, the reaction was continued for 5 hours while maintaining the temperature of the oil bath, leading to aging. After completion of the aging, the four-necked flask was removed from the oil bath and the reaction product was returned to room temperature, and then HPLC and FT-IR measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 2,2'-((oxybis(ethane-2,1-diyl))bis(oxy))bis(ethan-1-ol) and 2-isocyanatoethyl methacrylate raw materials disappeared, and new peak of 16-hydroxy-4-oxo-5,8,11,14-tetraoxa-3-azahexadecyl methacrylate (molecular weight of 349.38) was confirmed. As a result of the FT-IR measurement, the disappearance of the isocyanate absorption at 2,280 to 2,250 cm$^{-1}$ and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 27.2 g (77.7 mmol) of the precursor compound synthesized by the above-mentioned operation, 16.0 g (77.7 mmol) of (3-isocyanatopropyl)trimethoxysilane was added dropwise while stirring so as not to cause boiling of tetrahydrofuran. After completion of the dropwise addition, the reaction was continued for 12 hours, leading to aging. After completion of the aging, HPLC and FT-IR measurements were performed. As a result of the HPLC measurement, peaks of 16-hydroxy-4-oxo-5,8,11,14-tetraoxa-3-azahexadecyl methacrylate and (3-isocyanatopropyl)trimethoxysilane as raw materials disappeared, and new peak of 3,3-dimethoxy-8,22-dioxo-2,9,12,15,18,21-hexaoxa-7,23-diaza-3-silapentacosan-25-yl methacrylate (molecular weight of 554.7) was confirmed. As a result of the FT-IR measurement, the disappearance of the hydroxy group absorption at around 3,300 cm$^{-1}$ was confirmed. The chemical structure of the compound synthesized in the present Synthesis Example is mentioned below.

condenser tube, 300 mL of tetrahydrofuran, 19.4 g (0.10 mol) of 2,2'-((oxybis(ethane-2,1-diyl))bis(oxy))bis(ethan-1-ol), 29.4 mg of dibutyltin(IV) dilaurate and 14.7 mg of p-methoxyphenol were charged and dissolved. Subsequently, 9.96 g (0.05 mol) of 2-(2-isocyanatoethoxy)ethyl methacrylate was weighed in a beaker and 150 mL of tetrahydrofuran was added, followed by sufficient stirring and further liquid transfer to the dropping funnel. The four-necked flask was immersed in an oil bath heated to 75° C., and 2-(2-isocyanatoethoxy)ethyl methacrylate was added dropwise so as not to cause boiling of tetrahydrofuran. After completion of the dropwise addition, the reaction was continued for 5 hours while maintaining the temperature of the oil bath, leading to aging. After completion of the aging, the four-necked flask was removed from the oil bath and the reaction product was returned to room temperature, and then HPLC and FT-IR measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 2,2'-((oxybis(ethane-2,1-diyl))bis(oxy))bis(ethan-1-ol) and 2-(2-isocyanatoethoxy)ethyl methacrylate as raw materials disappeared, and new peak of 19-hydroxy-7-oxo-3,8,11,14,17-pentaoxa-6-azanonadecyl methacrylate (molecular weight of 393.43) was confirmed. As a result of the FT-IR measurement, the disappearance of the isocyanate absorption at 2,280 to 2,250 cm$^{-1}$ and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 29.4 g (74.7 mmol) of the precursor compound synthesized by the above-mentioned operation, 15.3 g (74.7 mmol) of (3-isocyanatopropyl)trimethoxysilane was added dropwise while stirring so as not to cause boiling of tetrahydrofuran. After completion of the dropwise addition, the reaction was continued for 12 hours, leading to aging. After completion of the aging, HPLC and FT-IR measurements were performed. As a result of the HPLC measurement, peaks of 19-hydroxy-7-oxo-3,8,11,14,17-pentaoxa-6-azanonadecyl methacrylate and (3-isocyanatopropyl)trimethoxysilane as raw materials disappeared, and new peak of 3,3-dimethoxy-8,22-dioxo-2,9,

[Chemical Formula 16]

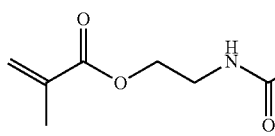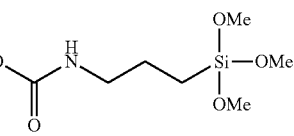

(Synthesis Example 2-II) Synthesis of Silane Coupling Agent 2-II Having a Radical Polymerizable Group In a four-necked flask (volume of 1 L) equipped with stirring blades, a thermometer, a dropping funnel and a 12,15,18,21,26-heptaoxa-7,23-diaza-3-silaoctacosan-28-yl methacrylate (molecular weight of 598.72) was confirmed. As a result of the FT-IR measurement, the disappearance of the hydroxy group absorption at around 3,300 cm$^{-1}$ was confirmed. The chemical structure of the compound synthesized in the present Synthesis Example is mentioned below.

[Chemical Formula 17]

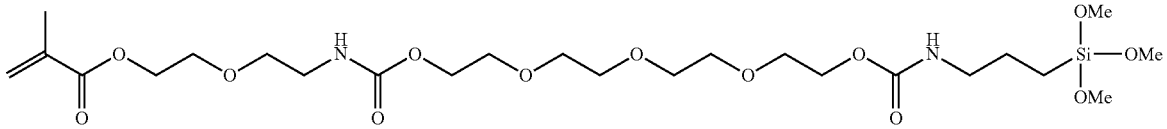

(Synthesis Example 3-II) Synthesis of Silane Coupling Agent 3-II Having a Radical Polymerizable Group In a four-necked flask (volume of 1 L) equipped with stirring blades, a thermometer, a dropping funnel and a condenser tube, 300 mL of tetrahydrofuran, 25.0 g (0.10 mol) of 2-(2-(2-(2-hydroxypropoxy)propoxy)propoxy)propan-1-ol, 32.8 mg of dibutyltin(IV) dilaurate and 16.4 mg of p-methoxyphenol were charged and dissolved. Subsequently, 7.76 g (0.05 mol) of 2-isocyanatoethyl methacrylate was weighed in a beaker and 150 mL of tetrahydrofuran was added, followed by sufficient stirring and further liquid transfer to the dropping funnel. The four-necked flask was immersed in an oil bath heated to 75° C., and 2-isocyanatoethyl methacrylate was added dropwise so as not to cause boiling of tetrahydrofuran. After completion of the dropwise addition, the reaction was continued for 5 hours while maintaining the temperature of the oil bath, leading to aging. After completion of the aging, the four-necked flask was removed from the oil bath and the reaction product was returned to room temperature, and then HPLC and FT-IR measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 2-(2-(2-(2-hydroxypropoxy)propoxy)propoxy)propan-1-ol and 2-isocyanatoethyl methacrylate as raw materials disappeared, and new peak of 16-hydroxy-6,9,12,15-tetramethyl-4-oxo-5,8,11,14-tetraoxa-3-azahexadecyl methacrylate (molecular weight of 405.49) was confirmed. As a result of the FT-IR measurement, the disappearance of the isocyanate absorption at 2,280 to 2,250 cm$^{-1}$ and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 32.8 g (80.8 mmol) of the precursor compound synthesized by the above-mentioned operation, 16.6 g (80.8 mmol) of (3-isocyanatopropyl)trimethoxysilane was added dropwise while stirring so as not to cause boiling of tetrahydrofuran. After completion of the dropwise addition, the reaction was continued for 12 hours, leading to aging. After completion of the aging, HPLC and FT-IR measurements were performed. As a result of the HPLC measurement, peaks of 16-hydroxy-6,9,12,15-tetramethyl-4-oxo-5,8,11,14-tetraoxa-3-azahexadecyl methacrylate and (3-isocyanatopropyl)trimethoxysilane as raw materials disappeared, and new peak of 3,3-dimethoxy-11,14,17,20-tetramethyl-8,22-dioxo-2,9,12,15,18,21-hexaoxa-7,23-diaza-3-silapentacosan-25-yl methacrylate (molecular weight of 610.77) was confirmed. As a result of the FT-IR measurement, the disappearance of the hydroxy group absorption at around 3,300 cm$^{-1}$ was confirmed. The chemical structure of the compound synthesized in the present Synthesis Example is mentioned below.

[Chemical Formula 18]

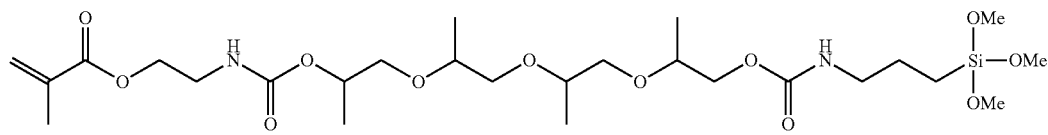

(Synthesis Example 4-II) Synthesis of Silane Coupling Agent 4-II Having a Radical Polymerizable Group In a four-necked flask (volume of 1 L) equipped with stirring blades, a thermometer, a dropping funnel and a condenser tube, 300 mL of tetrahydrofuran, 15.0 g (0.10 mol) of 2,2'-(ethane-1,2-diylbis(oxy))bis(ethan-1-ol), 22.8 mg of dibutyltin(IV) dilaurate and 11.4 mg of p-methoxyphenol were charged and dissolved. Subsequently, 7.76 g (0.05 mol) of 2-isocyanatoethyl methacrylate was weighed in a beaker, 150 mL of tetrahydrofuran was added, followed by sufficient stirring and further liquid transfer to the dropping funnel. The four-necked flask was immersed in an oil bath heated to 75° C., and 2-isocyanatoethyl methacrylate added dropwise so as not to cause boiling of tetrahydrofuran. After completion of the dropwise addition, the reaction was continued for 5 hours while maintaining the temperature of the oil bath, leading to aging. After completion of the aging, the four-necked flask was removed from the oil bath and the reaction product was returned to room temperature, and then HPLC and FT-IR measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 2,2'-(ethane-1,2-diylbis(oxy))bis(ethan-1-ol) and 2-isocyanatoethyl methacrylate as raw materials disappeared, and new peak of 13-hydroxy-4-oxo-5,8,11-trioxa-3- azatridecylmethacrylate (molecular weight of 305.33) was confirmed. As a result of the FT-IR measurement, the disappearance of the isocyanate absorption at 2,280 to 2,250 cm$^{-1}$ and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 22.8 g (74.5 mmol) of the precursor compound synthesized by the above-mentioned operation, 15.3 g (74.5 mmol) of (3-isocyanatopropyl)trimethoxysilane was added dropwise while stirring so as not to cause boiling of tetrahydrofuran. After completion of the dropwise addition, the reaction was continued for 12 hours, leading to aging. After completion of the aging, HPLC and FT-IR measurements were performed. As a result of the HPLC measurement, peaks of 13-hydroxy-4-oxo-5,8,11-trioxa-3-azatridecyl methacrylate and (3-isocyanatopropyl)trimethoxysilane as raw materials disappeared, and new peak of 3,3-dimethoxy-8,19-dioxo-2,9,12,15,18-pentaoxa-7,20-diaza-3-siladocosan-22-yl methacrylate (molecular weight of 510.61) was confirmed. As a result of the FT-IR measurement, the disappearance of the hydroxy group absorption at around 3,300 cm$^{-1}$ was confirmed. The chemical structure of the compound synthesized in the present Synthesis Example is mentioned below.

measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 2,2'-(ethane-1,2-diylbis(oxy))bis(ethan-1-ol) and 2-(2-isocyanatoethoxy)ethyl methacrylate as raw materials disappeared, and new peak of 16-hydroxy-7-oxo-3,8,11,14-tetraoxa-6-azahexadecyl methacrylate (molecular weight of 349.38) was confirmed. As a result of the FT-IR measurement, the disappearance of the isocyanate absorption at 2,280 to 2,250 cm$^{-1}$ and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 25.0 g (71.4 mmol) of the precursor compound synthesized by the above-mentioned operation, 14.7 g (71.4 mmol) of (3-isocyanatopropyl)trimethoxysilane was added dropwise while stirring so as not to cause boiling of tetrahydrofuran. After completion of the dropwise addition, the reaction was continued for 12

[Chemical Formula 19]

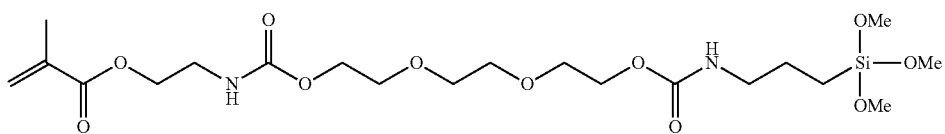

(Synthesis Example 5-II) Synthesis of Silane Coupling Agent 5-II Having a Radical Polymerizable Group In a four-necked flask (volume of 1 L) equipped with stirring blades, a thermometer, a dropping funnel and a condenser tube, 300 mL of tetrahydrofuran, 15.0 g (0.10 mol) of 2,2'-(ethane-1,2-diylbis(oxy))bis(ethan-1-ol), 25.0 mg of dibutyltin(IV) dilaurate and 12.5 mg of p-methoxyphenol were charged and dissolved. Subsequently, 9.96 g (0.05 mol) of 2-(2-isocyanatoethoxy)ethyl methacrylate was weighed in a beaker, 150 mL of tetrahydrofuran was added, followed by sufficient stirring and further liquid transfer to the dropping funnel. The four-necked flask was immersed in an oil bath heated to 75° C., and 2-(2-isocyanatoethoxy) ethyl methacrylate was added dropwise so as not to cause boiling of tetrahydrofuran. After completion of the dropwise addition, the reaction was continued for 5 hours while maintaining the temperature of the oil bath, leading to aging. After completion of the aging, the four-necked flask was removed from the oil bath and the reaction product was returned to room temperature, and then HPLC and FT-IR hours, leading to aging. After completion of the aging, HPLC and FT-IR measurements were performed. As a result of the HPLC measurement, peaks of 16-hydroxy-7-oxo-3,8,11,14-tetraoxa-6-azahexadecyl methacrylate and (3-isocyanatopropyl)trimethoxysilane as raw materials disappeared, and new peak of 3,3-dimethoxy-8,19-dioxo-2,9,12,15,18,23-hexaoxa-7,20-diaza-3-silapentacosan-25-yl methacrylate (molecular weight of 554.66) was confirmed. As a result of the FT-IR measurement, the disappearance of the hydroxy group absorption at around 3,300 cm$^{-1}$ was confirmed. The chemical structure of the compound synthesized in the present Synthesis Example is mentioned below.

[Chemical Formula 20]

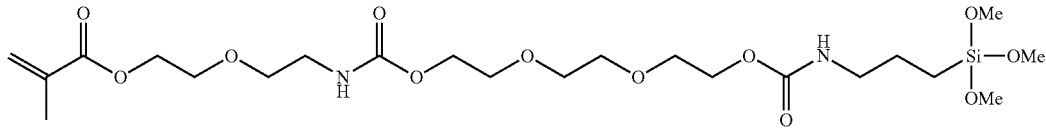

(Synthesis Example 6-II) Synthesis of Silane Coupling Agent 6-II Having a Radical Polymerizable Group In a four-necked flask (volume of 1 L) equipped with stirring blades, a thermometer, a dropping funnel and a condenser tube, 300 mL of tetrahydrofuran, 15.0 g (0.10 mol) of 2,2'-(ethane-1,2-diylbis(oxy))bis(ethan-1-ol), 27.0 mg of dibutyltin(IV) dilaurate and 13.5 mg of p-methoxyphenol were charged and dissolved. Subsequently, 12.0 g (0.05 mol) of 2-isocyanato-2-methylpropane-1,3-diyl diacrylate was weighed in a beaker and 150 mL of tetrahydrofuran was added, followed by sufficient stirring and further liquid transfer to the dropping funnel. The four-necked flask was immersed in an oil bath heated to 75° C., and 2-isocyanato-2-methylpropane-1,3-diyl diacrylate was added dropwise so as not to cause boiling of tetrahydrofuran. After completion of the dropwise addition, the reaction was continued for 5 hours while maintaining the temperature of the oil bath, leading to aging. After completion of the aging, the four-necked flask was removed from the oil bath and the reaction product was returned to room temperature, and then HPLC and FT-IR measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 2,2'-(ethane-1,2-diylbis(oxy))bis(ethan-1-ol) and 2-isocyanato-2-methylpropane-1,3-diyl diacrylate as raw materials disappeared, and new peak of 2-(((2-(2-(2-hydroxyethoxy)ethoxy)ethoxy)carbonyl)amino)-2-methylpropane-1,3-diyl diacrylate (molecular weight of 389.40) was confirmed. As a result of the FT-IR measurement, the disappearance of the isocyanate absorption at 2,280 to 2,250 cm$^{-1}$ and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 27.0 g (69.3 mmol) of the precursor compound synthesized by the above-mentioned operation, 14.2 g (69.3 mmol) of (3-isocyanatopropyl)trimethoxysilane was added dropwise while stirring so as not to cause boiling of tetrahydrofuran. After completion of the dropwise addition, the reaction was continued for 12 hours, leading to aging. After completion of the aging, HPLC and FT-IR measurements were performed. As a result of the HPLC measurement, peaks of 2-(((2-(2-(2-hydroxyethoxy)ethoxy)ethoxy)carbonyl)amino)-2-methylpropane-1,3-diyl diacrylate and (3-isocyanatopropyl)trimethoxysilane as raw materials disappeared, and new peak of 2-((3,3-dimethoxy-8-oxo-2,9,12,15,18-pentaoxa-7-aza-3-silanonadecan-19-oyl)amino)-2-methylpropane-1,3-diyl diacrylate (molecular weight of 594.69) was confirmed. As a result of the FT-IR measurement, the disappearance of the hydroxy group absorption at around 3,300 cm$^{-1}$ was confirmed. The chemical structure of the compound synthesized in the present Synthesis Example is mentioned below.

(Synthesis Example 7-II) Synthesis of Silane Coupling Agent 7-II Having a Radical Polymerizable Group In a four-necked flask (volume of 1 L) equipped with stirring blades, a thermometer, a dropping funnel and a condenser tube, 300 mL of tetrahydrofuran, 41.4 g (0.10 mol) of 3,6,9,12,15,18,21,24-octaoxahexacosan-1,26-diol, 48.5 mg of dibutyltin(IV) dilaurate and 24.2 mg of p-methoxyphenol were charged and dissolved. Subsequently, 7.06 g (0.05 mol) of 2-isocyanatoethyl acrylate was weighed in a beaker and 150 mL of tetrahydrofuran was added, followed by sufficient stirring and further liquid transfer to the dropping funnel. The four-necked flask was immersed in an oil bath heated to 75° C., and 2-isocyanatoethyl acrylate was added dropwise so as not to cause boiling of tetrahydrofuran. After completion of the dropwise addition, the reaction was continued for 5 hours while maintaining the temperature of the oil bath, leading to aging. After completion of the aging, the four-necked flask was removed from the oil bath and the reaction product was returned to room temperature, and then HPLC and FT-IR measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 3,6,9,12,15,18,21,24-octaoxahexacosan-1,26-diol and 2-isocyanatoethyl acrylate as raw materials disappeared, and new peak of 31-hydroxy-4-oxo-5,8,11,14,17,20,23,26,29-nonaoxa-3-azahentriacontyl acrylate (molecular weight of 555.62) was confirmed. As a result of the FT-IR measurement, the disappearance of the isocyanate absorption at 2,280 to 2,250 ca-1 and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 48.5 g (87.2 mmol) of the precursor compound synthesized by the above-mentioned operation, 17.9 g (87.2 mmol) of (3-isocyanatopropyl)trimethoxysilane was added dropwise while stirring so as not to cause boiling of tetrahydrofuran. After completion of the dropwise addition, the reaction was continued for 12 hours, leading to aging. After completion of the aging, HPLC and FT-IR measurements were performed. As a result of the HPLC measurement, peaks of 31-hydroxy-4-oxo-5,8,11,14,17,20,23,26,29-nonaoxa-3-azahentriacontyl acrylate and (3-isocyanatopropyl)trimethoxysilane as raw materials disappeared, and new peak of 3,3-dimethoxy-8,37-dioxo-2,9,12,15,18,21,24,27,30,33,36-undecaoxa-7,38-diaza-3-silatetracontan-40-yl acrylate (molecular weight of

[Chemical Formula 21]

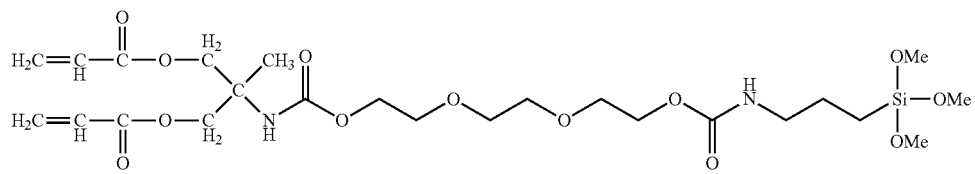

760.9) was confirmed. As a result of the FT-IR measurement, the disappearance of the hydroxy group absorption at around 3,300 cm$^{-1}$ was confirmed. The chemical structure of the compound synthesized in the present Synthesis Example is mentioned below.

manner as in the first stage reaction, a reaction was performed by immersed in an oil bath heated to 75° C. After completion of the dropwise addition, the reaction was continued for 24 hours, leading to aging. After completion of the aging, HPLC and FT-IR measurements were performed. As

[Chemical Formula 22]

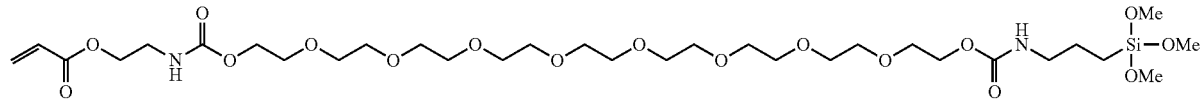

(Synthesis Example 1-III) Synthesis of Silane Coupling Agent 1-III Having a Radical Polymerizable Group In a four-necked flask (volume of 1 L) equipped with stirring blades, a thermometer, a dropping funnel and a condenser tube, 300 mL of tetrahydrofuran, 17.4 g (0.10 mol) of decane-1,10-diol and 12.6 mg of p-methoxyphenol were charged and dissolved. Subsequently, 7.76 g (0.05 mol) of 2-isocyanatoethyl methacrylate was weighed in a beaker and 150 mL of tetrahydrofuran was added, followed by sufficient stirring and further liquid transfer to the dropping funnel. The four-necked flask was immersed in an oil bath heated to 75° C., and 2-isocyanatoethyl methacrylate was added dropwise so as not to cause boiling of tetrahydrofuran. After completion of the dropwise addition, the reaction was continued for 24 hours while maintaining the temperature of the oil bath, leading to aging. After completion of the aging, the four-necked flask was removed from the oil bath and the reaction product was returned to room temperature, and then HPLC and FT-IR measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of decane-1,10-diol and 2-isocyanatoethyl methacrylate as raw materials disappeared, and new peak of 2-((((10-hydroxydecyl)oxy)carbonyl)amino)ethyl methacrylate (molecular weight of 329.44) was confirmed. As a result of the FT-IR measurement, the disappearance of the isocyanate absorption at 2,280 to 2,250 cm$^{-1}$ and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 25.2 g (76.4 mmol) of the precursor compound synthesized by the above-mentioned operation, 15.7 g (76.4 mmol) of (3-isocyanatopropyl)trimethoxysilane was added dropwise while stirring so as not to cause boiling of tetrahydrofuran. In the same a result of the HPLC measurement, peaks of 2-((((10-hydroxydecyl)oxy)carbonyl)amino)ethyl methacrylate and (3-isocyanatopropyl)trimethoxysilane as raw materials disappeared, and new peak of 3,3-dimethoxy-8,21-dioxo-2,9,20-trioxa-7,22-diaza-3-silatetracosan-24-yl methacrylate (molecular weight of 534.72) was confirmed. As a result of the FT-IR measurement, the disappearance of the hydroxy group absorption at around 3,300 cm$^{-1}$ was confirmed. The chemical structure of the compound synthesized in the present Synthesis Example is mentioned below.

[Chemical Formula 23]

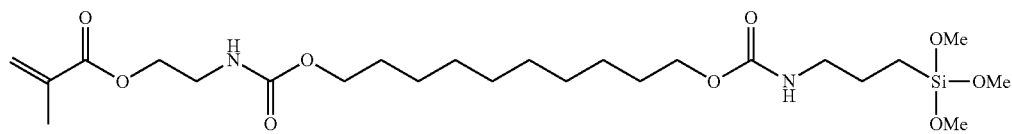

(Synthesis Example 2-III) Synthesis of Silane Coupling Agent 2-III Having a Radical Polymerizable Group In a four-necked flask (volume of 1 L) equipped with stirring blades, a thermometer, a dropping funnel and a condenser tube, 300 mL of tetrahydrofuran, 18.8 g (0.10 mol) of undecane-1,11-diol and 14.4 mg of p-methoxyphenol were charged and dissolved. Subsequently, 9.96 g (0.05 mol) of 2-(2-isocyanatoethoxy)ethyl methacrylate was weighed in a beaker and 150 mL of tetrahydrofuran was added, followed by sufficient stirring and further liquid transfer to the dropping funnel. The four-necked flask was immersed in an oil bath heated to 75° C., and 2-(2-isocyanatoethoxy)ethyl methacrylate was added dropwise so as not to cause boiling of tetrahydrofuran. After completion of the dropwise addition, the reaction was continued for 24 hours while maintaining the temperature of the oil bath, leading to aging. After completion of the aging, the four-necked flask was removed from the oil bath and the reaction product was returned to room temperature, and then HPLC and FT-IR measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of undecane-1,11-diol and 2-(2-isocyanatoethoxy)ethyl methacrylate as raw materials disappeared, and new peak of 2-(2-((((11-hydroxyundecyl)oxy)carbonyl)amino)ethoxy) ethyl methacrylate (molecular weight of 387.52) was confirmed. As a result of the FT-IR measurement, the disappearance of the isocyanate absorption at 2,280 to 2,250 cm$^{-1}$ and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 28.8 g (74.2 mmol) of the precursor compound synthesized by the above-mentioned operation, 15.2 g (74.2 mmol) of (3-isocyanatopropyl)trimethoxysilane was added dropwise while stirring so as not to cause boiling of tetrahydrofuran. In the same manner as in the first stage, a reaction was performed by immersing in an oil bath heated to 75° C. After completion of the dropwise addition, the reaction was continued for 24 hours, leading to aging. After completion of the aging, HPLC and FT-IR measurements were performed. As a result of the HPLC measurement, peaks of 2-(2-((((11-hydroxyundecyl)oxy)carbonyl)amino)ethoxy)ethyl methacrylate and (3-isocyanatopropyl)trimethoxysilane as raw materials disappeared, and new peak of 3,3-dimethoxy-8,22-dioxo-2,9,21,26-tetraoxa-7,23-diaza-3-silaoctacosan-28-ylmethacrylate (molecular weight of 592.80) was confirmed. As a result of the FT-IR measurement, the disappearance of the hydroxy group absorption at around 3,300 cm$^{-1}$ was confirmed. The chemical structure of the compound synthesized in the present Synthesis Example is mentioned below.

wise addition, the reaction was continued for 24 hours while maintaining the temperature of the oil bath, leading to aging. After completion of the aging, the four-necked flask was removed from the oil bath and the reaction product was returned to room temperature, and then HPLC and FT-IR measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 2,5,8-trimethyldodecane-1,11-diol and 2-isocyanatoethyl methacrylate as raw materials disappeared, and new peak of 2-((((12-hydroxy-5,8,11-trimethyldodecan-2-yl)oxy)carbonyl)amino)ethyl methacrylate (molecular weight of 399.57) was confirmed. As a result of the FT-IR measurement, the disappearance of the isocyanate absorption at 2,280 to 2,250 cm$^{-1}$ and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 32.2 g (80.6 mmol) of the precursor compound synthesized by the above-mentioned operation, 16.5 g (80.6 mmol) of (3-isocyanatopropyl)trimethoxysilane was added dropwise while stirring under tetrahydrofuran reflux. In the same manner as in the first stage, a reaction was

[Chemical Formula 24]

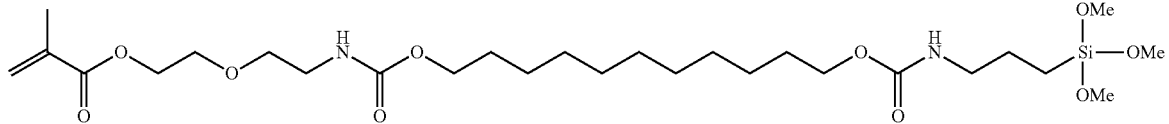

(Synthesis Example 3-III) Synthesis of Silane Coupling Agent 3-III Having a Radical Polymerizable Group In a four-necked flask (volume of 1 L) equipped with stirring blades, a thermometer, a dropping funnel and a condenser tube, 300 mL of tetrahydrofuran, 24.4 g (0.10 mol) of 2,5,8-trimethyldodecane-1,11-diol and 16.1 mg of p-methoxyphenol were charged and dissolved. Subsequently, 7.76 g (0.05 mol) of 2-isocyanatoethyl methacrylate was weighed in a beaker and 150 mL of tetrahydrofuran was added, followed by sufficient stirring and further liquid transfer to the dropping funnel. The four-necked flask was immersed in an oil bath heated to 85° C., and 2-isocyanatoethyl methacrylate was added dropwise while stirring under tetrahydrofuran reflux. After completion of the dropperformed by immersing in an oil bath heated to 85° C. After completion of the dropwise addition, the reaction was continued for 24 hours, leading to aging. After completion of the aging, HPLC and FT-IR measurements were performed. As a result of the HPLC measurement, peaks of 2-((((12-hydroxy-5,8,11-trimethyldodecan-2-yl)oxy)carbonyl) amino)ethyl methacrylate and (3-isocyanatopropyl) trimethoxysilane as raw materials disappeared, and new peak of 3,3-dimethoxy-11,14,17,20-tetramethyl-8,22-dioxo-2,9,21-trioxa-7,23-diaza-3-silapentacosan-25-yl methacrylate (molecular weight of 604.86) was confirmed. As a result of the FT-IR measurement, the disappearance of the hydroxy group absorption at around 3,300 cm$^{-1}$ was confirmed. The chemical structure of the compound synthesized in the present Synthesis Example is mentioned below.

[Chemical Formula 25]

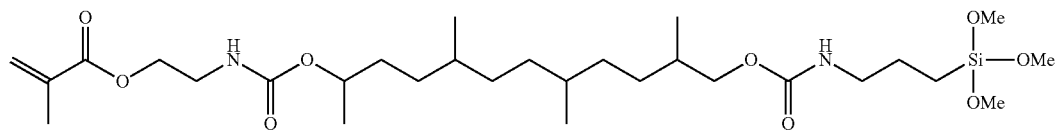

(Synthesis Example 4-III) Synthesis of Silane Coupling Agent 4-III Having a Radical Polymerizable Group In a four-necked flask (volume of 1 L) equipped with stirring blades, a thermometer, a dropping funnel and a condenser tube, 300 mL of tetrahydrofuran, 14.6 g (0.10 mol) of octane-1,8-diol and 11.2 mg of p-methoxyphenol were charged and dissolved. Subsequently, 7.76 g (0.05 mol) of 2-isocyanatoethyl methacrylate was weighed in a beaker and 150 mL of tetrahydrofuran was added, followed by sufficient stirring and further liquid transfer to the dropping funnel. The four-necked flask was immersed in an oil bath heated to 85° C., and 2-isocyanatoethyl methacrylate was added dropwise while stirring under tetrahydrofuran reflux. After completion of the dropwise addition, the reaction was continued for 24 hours while maintaining the temperature of the oil bath, leading to aging. After completion of the aging, the four-necked flask was removed from the oil bath and the reaction product was returned to room temperature, and then HPLC and FT-IR measurements were performed. In that case, a sample obtained by collecting a very small amount of the reaction product using a pipette and removing a solvent using evaporator was used. Analysis conditions of the HPLC measurement are as follows: a column of ZOR-BAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of octane-1,8-diol and 2-isocyanatoethyl methacrylate as raw materials disappeared, and new peak of 2-((((8-hydroxyoctyl)oxy)carbonyl)amino)ethyl methacrylate (molecular weight of 301.38) was confirmed. As a result of the FT-IR measurement, the disappearance of the isocyanate absorption at 2,280 to 2,250 cm$^{-1}$ and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 22.4 g (74.3 mmol) of the precursor compound synthesized by the above-mentioned operation, 15.3 g (74.3 mmol) of (3-isocyanatopropyl)trimethoxysilane was added dropwise while stirring under tetrahydrofuran reflux. In the same manner as in the first stage, a reaction was performed by immersing in an oil bath heated to 85° C. After completion of the dropwise addition, the reaction was continued for 24 hours, leading to aging. After completion of the aging, HPLC and FT-IR measurements were performed. As a result of the HPLC measurement, peaks of 2-((((8-hydroxyoctyl)oxy)carbonyl)amino)ethyl methacrylate and (3-isocyanatopropyl)trimethoxysilane as raw materials disappeared, and new peak of 3,3-dimethoxy-8,19-dioxo-2,9,18-trioxa-7,20-diaza-3-siladocosan-22-ylmethacrylate (molecular weight of 506.67) was confirmed. As a result of the FT-IR measurement, the disappearance of the hydroxy group absorption at around 3,300 cm$^{-1}$ was confirmed. The chemical structure of the compound synthesized in the present Synthesis Example is mentioned below.

(Synthesis Example 5-III) Synthesis of Silane Coupling Agent 5-III Having a Radical Polymerizable Group In a four-necked flask (volume of 1 L) equipped with stirring blades, a thermometer, a dropping funnel and a condenser tube, 300 mL of tetrahydrofuran, 14.6 g (0.10 mol) of octane-1,8-diol and 12.3 mg of p-methoxyphenol were charged and dissolved. Subsequently, 9.96 g (0.05 mol) of 2-(2-isocyanatoethoxy)ethyl methacrylate was weighed in a beaker and 150 mL of tetrahydrofuran was added, followed by sufficient stirring and further liquid transfer to the dropping funnel. The four-necked flask was immersed in an oil bath heated to 85° C., and 2-(2-isocyanatoethoxy)ethyl methacrylate was added dropwise while stirring under tetrahydrofuran reflux. After completion of the dropwise addition, the reaction was continued for 24 hours while maintaining the temperature of the oil bath, leading to aging. After completion of the aging, the four-necked flask was removed from the oil bath and the reaction product was returned to room temperature, and then HPLC and FT-IR measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of octane-1,8-diol and 2-(2-isocyanatoethoxy)ethyl methacrylate as raw materials disappeared, and new peak of 2-(2-((((8-hydroxyoctyl)oxy)carbonyl)amino)ethoxy)ethyl methacrylate (molecular weight of 345.44) was confirmed. As a result of the FT-IR measurement, the disappearance of the isocyanate absorption at 2,280 to 2,250 cm$^{-1}$ and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 24.6 g (71.2 mmol) of the precursor compound synthesized by the above-mentioned operation, 14.6 g (71.2 mmol) of (3-isocyanatopropyl)trimethoxysilane was added dropwise while stirring under tetrahydrofuran reflux. In the same manner as in the first stage, a reaction was performed by immersing in an oil bath heated to 75° C. After completion of the dropwise addition, the reaction was continued for 24 hours, leading to aging. After completion of the aging, HPLC and FT-IR measurements were performed. As a result of the HPLC measurement, peaks of 2-(2-((((8-hydroxyoctyl)oxy)carbonyl)amino)ethoxy)ethyl methacrylate and (3-isocyanatopropyl)trimethoxysilane as raw materials disappeared, and new peak of 3,3-dimethoxy-8,19-dioxo-2,9,18,23-tetraoxa-7,20-diaza-3-silapentacosan-25-yl methacrylate (molecular weight of 550.72) was confirmed. As a result of the FT-IR measurement, the disappearance of the hydroxy group absorption at around 3,300 cm$^{-1}$ was confirmed. The chemi-

[Chemical Formula 26]

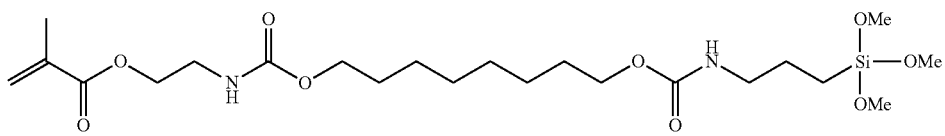

cal structure of the compound synthesized in the present Synthesis Example is mentioned below.

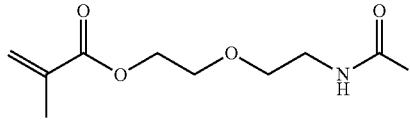

[Chemical Formula 27]

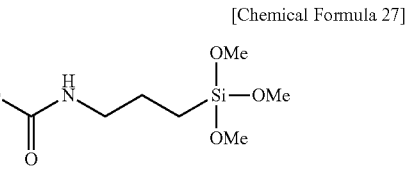

(Synthesis Example 6-III) Synthesis of Silane Coupling Agent 6-III Having a Radical Polymerizable Group In a four-necked flask (volume of 1 L) equipped with stirring blades, a thermometer, a dropping funnel and a condenser tube, 300 mL of tetrahydrofuran, 14.6 g (0.10 mol) of octane-1,8-diol and 13.3 mg of p-methoxyphenol were charged and dissolved. Subsequently, 12.0 g (0.05 mol) of 2-isocyanato-2-methylpropane-1,3-diyl diacrylate was weighed in a beaker and 150 mL of tetrahydrofuran was added, followed by sufficient stirring and further liquid transfer to the dropping funnel. The four-necked flask was immersed in an oil bath heated to 85° C., and 2-isocyanato-2-methylpropane-1,3-diyl diacrylate was added dropwise while stirring under tetrahydrofuran reflux. After completion of the dropwise addition, the reaction was continued for 24 hours while maintaining the temperature of the oil bath, leading to aging. After completion of the aging, the four-necked flask was removed from the oil bath and the reaction product was returned to room temperature, and then HPLC and FT-IR measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of octane-1,8-diol and 2-isocyanato-2-methylpropane-1,3-diyl diacrylate as raw materials disappeared, and new peak of 2-((((8-hydroxyoctyl)oxy)carbonyl)amino)-2-methylpropane-1,3-diyl diacrylate (molecular weight of 385.46) was confirmed. As a result of the FT-IR measurement, the disappearance of the isocyanate absorption at 2,280 to 2,250 $cm^{-1}$ and a decrease in intensity of the hydroxy group absorption at around 3,300 $cm^{-1}$ were confirmed, and the absorption attributed to a urethane group was newly confirmed at 1,250 $cm^{-1}$. Subsequently, to a tetrahydrofuran solution containing 26.6 g (69.0 mmol) of the precursor compound synthesized by the above-mentioned operation, 14.2 g (69.0 mmol) of (3-isocyanatopropyl)trimethoxysilane was added dropwise while stirring under tetrahydrofuran reflux. In the same manner as in the first stage, a reaction was performed by immersing in an oil bath heated to 85° C. After completion of the dropwise addition, the reaction was continued for 24 hours, leading to aging. After completion of the aging, HPLC and FT-IR measurements were performed. As a result of the HPLC measurement, peaks of 2-((((8-hydroxyoctyl)oxy)carbonyl)amino)-2-methylpropane-1,3-diyl diacrylate and (3-isocyanatopropyl)trimethoxysilane as raw materials disappeared, and new peak of 2-((3,3-dimethoxy-8-oxo-2,9,18-trioxa-7-aza-3-silanonadecan-19-oyl)amino)-2-methylpropane-1,3-diyl diacrylate (molecular weight of 590.74) was confirmed. As a result of the FT-IR measurement, the disappearance of the hydroxy group absorption at around 3,300 $cm^{-1}$ was confirmed. The chemical structure of the compound synthesized in the present Synthesis Example is mentioned below.

[Chemical Formula 28]

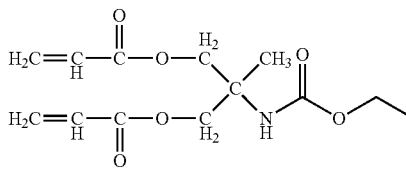

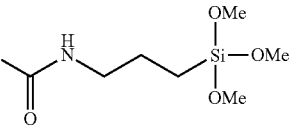

(Synthesis Example 7-III) Synthesis of Silane Coupling Agent 7-III Having a Radical Polymerizable Group In a pressure-resistant reaction vessel (volume of 1 L) equipped with stirring blades and a thermometer, 450 mL of tetrahydrofuran, 39.9 g (0.10 mol) of hexacosane-1,26-diol, 7.06 g (0.05 mol) of 2-isocyanatoethyl acrylate and 23.5 mg of p-methoxyphenol were charged and dissolved by sufficiently stirring. Subsequently, a pressure of 0.5 MPa was applied to the pressure-resistant reaction vessel using an argon gas. The pressure-resistant reaction vessel was immersed in an oil bath heated to 90° C. and a reaction was performed while stirring for 12 hours. After completion of the reaction, the pressure-resistant reaction vessel was removed from the oil bath and the reaction product was returned to room temperature, and then the argon gas was slowly removed and the pressure was returned to normal pressure. Subsequently, HPLC and FT-IR measurements were performed. In that case, a sample obtained by collecting a very small amount of the reaction product using a pipette and removing a solvent using evaporator was used. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of hexacosane-1,26-diol and 2-isocyanatoethyl acrylate as raw materials disappeared, and new peak of 2-((((26-hydroxyhexacosyl)oxy)carbonyl)amino)ethyl acrylate (molecular weight of 539.84) was confirmed. As a result of the FT-IR measurement, the disappearance of the isocyanate absorption at 2,280 to 2,250 cm$^{-1}$ and a decrease in intensity of the hydroxy group absorption at around 3,300 cm$^{-1}$ were confirmed, and the absorption attributed to a urethane group was newly confirmed at 1,250 cm$^{-1}$. Subsequently, to a tetrahydrofuran solution containing 47.0 g (87.0 mmol) of the precursor compound synthesized by the above-mentioned operation, 17.9 g (87.0 mmol) of (3-isocyanatopropyl)trimethoxysilane was added and then a reaction of the second stage was performed. In the same manner as in the first stage, the reaction was performed by immersing the pressure-resistant reaction vessel in an oil bath heated to 90° C. under 0.5 MPa argon gas for 12 hours. After completion of the reaction, the pressure-resistant reaction vessel was removed from the oil bath and the reaction product was returned to room temperature, and then the argon gas was slowly removed and the pressure was returned to normal pressure. Subsequently, HPLC and FT-IR measurements were performed. As a result of the HPLC measurement, peaks of 2-((((26-hydroxyhexacosyl)oxy)carbonyl)amino)ethyl acrylate and (3-isocyanatopropyl)trimethoxysilane as raw materials disappeared, and new peak of 3,3-dimethoxy-8,37-dioxo-2,9,36-trioxa-7,38-diaza-3-silatetracontan-40-yl acrylate (molecular weight of 745.13) was confirmed. As a result of the FT-IR measurement, the disappearance of the hydroxy group absorption at around 3,300 cm$^{-1}$ was confirmed. The chemical structure of the compound synthesized in the present Synthesis Example is mentioned below.

oil bath heated to 75° C., and 2-isocyanatoethyl methacrylate was added dropwise while stirring so that the inner temperature did not exceed 80° C. After completion of the dropwise addition, the reaction was continued while maintaining the temperature of an oil bath for 5 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 10-undecen-1-ol and 2-isocyanatoethyl methacrylate as raw materials disappeared, and new peak of 2-(((undec-10-en-1-yloxy)carbonyl)amino)ethyl methacrylate (molecular weight of 325.45) was confirmed. As a result of the FT-IR measurement, the isocyanate absorption at 2,280 to 2,250 cm$^{-1}$ and the disappearance of the hydroxy group absorption at around 3,300 cm$^{-1}$ was confirmed, and the absorption attributed to a urethane group was newly confirmed at 1,250 cm$^{-1}$. Subsequently, in a four-necked flask (volume of 100 mL) equipped with stirring blades, a thermometer, a dropping funnel and a condenser tube, 32.5 g (0.10 mol) of the precursor compound synthesized by the above-mentioned operation and 4.9 mg (corresponding to 100 ppm) of platinum(0)-1,3-divinyl-1,1,3,3-tetramethyldisiloxane were added, followed by sufficient stirring so as to obtain a uniform mixture. Separately, 16.4 g (0.10 mol) of triethoxysilane was weighed in the dropping funnel. In the four-necked flask, triethoxysilane was added dropwise at room temperature while stirring so that the inner temperature did not exceed 35° C. After completion of the dropwise

[Chemical Formula 29]

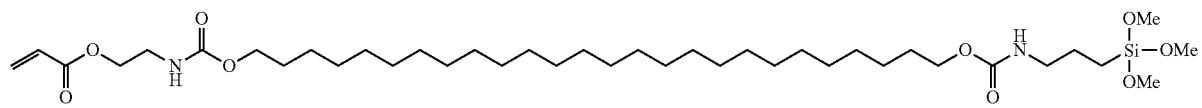

(Comparative Synthesis Example 1) Synthesis of Comparative Silane Coupling Agent 1 Having a Radical Polymerizable Group In a four-necked flask (volume of 100 mL) equipped with stirring blades, a thermometer, a dropping funnel and a condenser tube, 17.0 g (0.10 mol) of 10-undecen-1-ol, 32.5 mg (corresponding to 1,000 ppm) of dibutyltin(IV) dilaurate and 16.3 mg (corresponding to 500 ppm) of p-methoxyphenol were charged and dissolved. Subsequently, 15.5 g (0.10 mol) of 2-isocyanatoethyl methacrylate was weighed in the dropping funnel. The four-necked flask was immersed in an addition, the reaction was continued at room temperature for 12 hours, leading to aging. After completion of the aging, HPLC and FT-IR measurements were performed. As a result of the HPLC measurement, peaks of 2-(((undec-10-en-1-yloxy)carbonyl)amino)ethyl methacrylate and triethoxysilane as raw materials disappeared, and new peak of 4,4-diethoxy-17-oxo-3,16-dioxa-18-aza-4-silaicosan-20-yl methacrylate (molecular weight of 489.72) was confirmed. As a result of the FT-IR measurement, the disappearance of the silane group absorption at 2,190 cm$^{-1}$ was confirmed. The chemical structure of the compound synthesized in the present Synthesis Example is mentioned below.

[Chemical Formula 30]

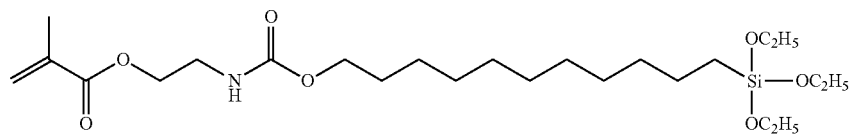

(Comparative Synthesis Example 2) Synthesis of Comparative Silane Coupling Agent 2 Having a Radical Polymerizable Group In a four-necked flask (volume of 100 mL) equipped with stirring blades, a thermometer, a dropping funnel and a condenser tube, 17.0 g (0.10 mol) of 10-undecen-1-ol, 40.9 mg (corresponding to 1,000 ppm) of dibutyltin(IV) dilaurate and 20.5 mg (corresponding to 500 ppm) of p-methoxyphenol were charged and dissolved. Subsequently, 23.9 g (0.10 mol) of 8-isocyanatooctyl methacrylate was weighed in the dropping funnel. The four-necked flask was immersed in an oil bath heated to 75° C., and 8-isocyanatooctyl methacrylate was added dropwise while stirring so that the inner temperature did not exceed 80° C. After completion of the dropwise addition, the reaction was continued while maintaining the temperature of an oil bath for 5 hours, leading to aging. After completion of the aging, the four-necked flask was removed from the oil bath and the reaction product was returned to room temperature, and then HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 10-undecen-1-ol and 8-isocyanatooctyl methacrylate as raw materials disappeared, and new peak of 8-(((undec-10-en-1-yloxy)carbonyl)amino)octyl methacrylate (molecular weight of 409.61) was confirmed. As a result of the FT-IR measurement, the isocyanate absorption at 2,280 to 2,250 cm$^{-1}$ and the disappearance of the hydroxy group absorption at around 3,300 cm$^{-1}$ was confirmed, and the absorption attributed to a urethane group was newly confirmed at 1,250 cm$^{-1}$. Subsequently, in a four-necked flask (volume of 100 mL) equipped with stirring blades, a thermometer, a dropping funnel and a condenser tube, 41.0 g (0.10 mol) of the precursor compound synthesized by the above-mentioned operation and 5.7 mg (corresponding to 100 ppm) of platinum(0)-1,3-divinyl-1,1,3,3-tetramethyldisiloxane were added, followed by sufficient stirring so as to obtain a uniform mixture. Separately, 16.4 g (0.10 mol) of triethoxysilane was weighed in the dropping funnel. In the four-necked flask, triethoxysilane was added dropwise at room temperature while stirring so that the inner temperature did not exceed 35° C. After completion of the dropwise addition, the reaction was continued at room temperature for 12 hours, leading to aging. After completion of the aging, HPLC and FT-IR measurements were performed. As a result of the HPLC measurement, peaks of 8-(((undec-10-en-1-yloxy)carbonyl)amino)octyl methacrylate and triethoxysilane as raw materials disappeared, and new peak of 4,4-diethoxy-17-oxo-3,16-dioxa-18-aza-4-silahexacosan-26-yl methacrylate (molecular weight of 573.89) was confirmed. As a result of the FT-IR measurement, the disappearance of the silane group absorption at 2,190 cm$^{-1}$ was confirmed. The chemical structure of the compound synthesized in the present Synthesis Example is mentioned below.

(Comparative Synthesis Example 3) Synthesis of Comparative Silane Coupling Agent 3 Having a Radical Polymerizable Group In a four-necked flask (volume of 100 mL) equipped with stirring blades, a thermometer, a dropping funnel and a condenser tube, 17.0 g (0.10 mol) of 10-undecen-1-ol, 45.1 mg (corresponding to 1,000 ppm) of dibutyltin(IV) dilaurate and 22.6 mg (corresponding to 500 ppm) of p-methoxyphenol were charged and dissolved. Subsequently, 28.1 g (0.10 mol) of 11-isocyanatoundecyl methacrylate was weighed in the dropping funnel. The four-necked flask was immersed in an oil bath heated to 75° C., and 8-isocyanatooctyl methacrylate was added dropwise while stirring so that the inner temperature did not exceed 80° C. After completion of the dropwise addition, the reaction was continued while maintaining the temperature of an oil bath for 5 hours, leading to aging. After completion of the aging, the four-necked flask was removed from the oil bath and the reaction product was returned to room temperature, HPLC and FT-IR measurements were performed. Analysis conditions of the HPLC measurement are as follows: a column of ZORBAX-ODS, acetonitrile/distilled water of 7/3, a flow rate of 0.5 mL/min, a multi-scanning UV detector, an RI detector and an MS detector. The FT-IR measurement was performed by an ATR method. As a result of the HPLC measurement, peaks of 10-undecen-1-ol and 11-isocyanatoundecyl methacrylate as raw materials disappeared, and new peak of 11-(((undec-10-en-1-yloxy)carbonyl)amino)undecyl methacrylate (molecular weight of 451.69) was confirmed. As a result of the FT-IR measurement, the isocyanate absorption at 2,280 to 2,250 cm$^{-1}$ and the disappearance of the hydroxy group absorption at around 3,300 cm$^{-1}$ was confirmed, and the absorption attributed to a urethane group was newly confirmed at 1,250 cm$^{-1}$ Subsequently, a four-necked flask (volume of 200 mL) equipped with stirring blades, a thermometer, a dropping funnel and a condenser tube, 45.2 g (0.10 mol) of the precursor compound synthesized by the above-mentioned operation and 6.2 mg (corresponding to 100 ppm) of platinum(0)-1,3-divinyl-1,1,3,3-tetramethyldisiloxane were added, followed by sufficient stirring so as to obtain a uniform mixture. Separately, 16.4 g (0.10 mol) of triethoxysilane was weighed in the dropping funnel. In the four-necked flask, triethoxysilane was added dropwise at room temperature while stirring so that the inner temperature did not exceed 35° C. After completion of the dropwise addition, the reaction was continued at room temperature for 12 hours, leading to aging. After completion of the aging, HPLC and FT-IR measurements were performed. As a result of the HPLC measurement, peaks of 11-(((undec-10-en-1-yloxy)carbonyl)amino)undecyl methacrylate and triethoxysilane as raw materials disappeared, and new peak of 4,4-diethoxy-17-oxo-3,16-dioxa-18-aza-4-silanonacosan-29-yl methacrylate (molecular weight of 615.97) was confirmed. As a result of the FT-IR measurement, the disap-

[Chemical Formula 31]

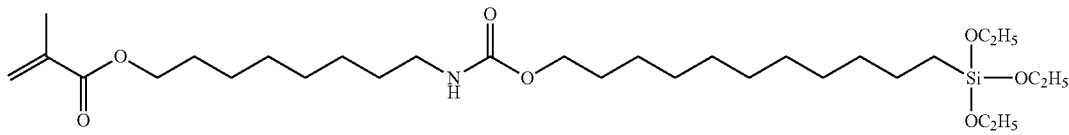

pearance of the silane group absorption at 2,190 cm$^{-1}$ was confirmed. The chemical structure of the compound synthesized in the present Synthesis Example is mentioned below.

[Chemical Formula 32]

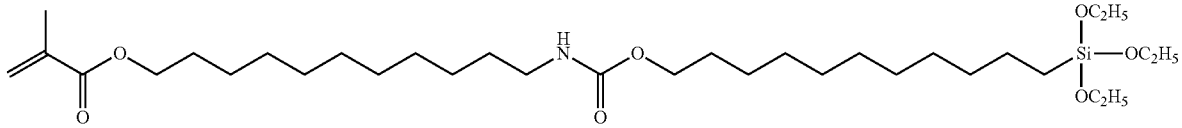

Examples 1-1-I to 1-7-I, Examples 1-1-II to 1-7-II and Examples 1-1-III to 1-7-III (Preparation of Medical and/or Dental Composite Resins—Inorganic Matter Filling Rate of 70% by Weight)

Using polymerizable silane coupling agents synthesized in Synthesis Examples 1-I to 7-I, Synthesis Examples 1-II to 7-II or Synthesis Examples 1-III to 7-III, surface modification with OX-50 (manufactured by NIPPON AEROSIL CO., LTD.) and Fuselex (manufactured by TATSUMORI LTD.) and preparation of medical and/or dental composite resins were performed. Specific surface modification method will be mentioned below. Each synthesized silane coupling agent in the amount mentioned in Tables 1-1-I to III was dissolved in 300 mL of ethanol and then the resulting solution was added in a 500 mL recovery flask charged with 15.0 g of OX-50 and 45.0 g of Fuselex. Subsequently, a magnetic stirrer was put in the recovery flask, followed by stirring for 10 minutes stirring and further dispersion using a 28 KHz-150 W ultrasonic disperser for 5 minutes. After completion of the dispersion, 2.4 g of distilled water and 1.2 g of an aqueous 1% by weight phosphoric acid solution were added under stirring, and then the flask was immersed in a boiling water bath and refluxed for 5 hours. After completion of the reflux, the inner temperature was returned to room temperature and a binder solution (UDMA, 2G) and a photopolymerization initiator mentioned in Table 1 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain medical and/or dental composite resins.

Examples 2-1-I to 2-7-I, Examples 2-1-II to 2-7-II and Examples 2-1-III to 2-7-III (Preparation of Medical and/or Dental Composite Resins—Inorganic Matter Filling Rate of 85% by Weight)

Using polymerizable silane coupling agents synthesized in Synthesis Examples 1-I to 7-I, Synthesis Examples 1-II to 7-II or Synthesis Examples 1-III to 7-III, surface modification with OX-50 (manufactured by NIPPON AEROSIL CO., LTD.) and Fuselex (manufactured by TATSUMORI LTD.) and preparation of medical and/or dental composite resins were performed. Specific surface modification method will be mentioned below. Each synthesized silane coupling agent in the amount mentioned in Tables 1-2-I to III was dissolved in 300 mL of ethanol and then the resulting solution was added in a 500 mL recovery flask charged with 15.0 g of OX-50 and 45.0 g of Fuselex. Subsequently, a magnetic stirrer was put in the recovery flask, followed by stirring for 10 minutes stirring and further dispersion using a 28 KHz-150 W ultrasonic disperser for 5 minutes. After completion of the dispersion, 2.4 g of distilled water and 1.2 g of an aqueous 1% by weight phosphoric acid solution were added under stirring, and then the flask was immersed in a boiling water bath and refluxed for 5 hours. After completion of the reflux, the inner temperature was returned to room temperature and a binder solution (UDMA, 2G) and a photopolymerization initiator mentioned in Table 1 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain medical and/or dental composite resins.

Examples 3-1-I to 3-7-I and Examples 3-1-II to 3-7-II (Preparation of Pressure-Sensitive Adhesive Pastes)

Using polymerizable silane coupling agents synthesized in Synthesis Examples 1-I to 7-I or Synthesis Examples 1-II to 7-II, surface modification with OX-50 (manufactured by NIPPON AEROSIL CO., LTD.) and preparation of pressure-sensitive adhesive pastes were performed. Specific surface modification method will be mentioned below. Each synthesized silane coupling agent in the amount mentioned in Tables 1-3-I to II was dissolved in 300 mL of ethanol and then the resulting solution was added in a 500 mL recovery flask charged with 15.0 g of OX-50. Subsequently, a magnetic stirrer was put in the recovery flask, followed by stirring for 10 minutes stirring and further dispersion using a 28 KHz-150 W ultrasonic disperser for 5 minutes. After completion of the dispersion, 0.65 g of distilled water and 0.33 g of an aqueous 1% by weight phosphoric acid solution were added under stirring, and then the flask was immersed in a boiling water bath and refluxed for 5 hours. After completion of the reflux, the inner temperature was returned to room temperature and a binder solution (UDMA, 2G) and a photopolymerization initiator mentioned in Table 1-3 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain pressure-sensitive adhesive pastes.

Comparative Examples 1-1 to 1-5

(Preparation of Medical and/or Dental Composite Resins—Inorganic Matter Filling Rate of 70% by Weight)

Using polymerizable silane coupling agents synthesized in Comparative Synthesis Examples 1 to 3 or two types of polymerizable silane coupling agents [KBM-503: 3-(trimethoxysilyl)propyl methacrylate, KBE-503: 3-(triethoxysilyl)propyl methacrylate] available from Shin-Etsu Chemical Co., Ltd., surface modification with OX-50

(manufactured by NIPPON AEROSIL CO., LTD.) and Fuselex (manufactured by TATSUMORI LTD.) and preparation of medical and/or dental composite resins were performed. Specific surface modification method will be mentioned below. Each synthesized silane coupling agent in the amount mentioned in Table 1-1-C was dissolved in 300 mL of ethanol and then the resulting solution was added in a 500 mL recovery flask charged with 15.0 g of OX-50 and 45.0 g of Fuselex. Subsequently, a magnetic stirrer was put in the recovery flask, followed by stirring for 10 minutes stirring and further dispersion using a 28 KHz-150 W ultrasonic disperser for 5 minutes. After completion of the dispersion, 2.4 g of distilled water and 1.2 g of an aqueous 1% by weight phosphoric acid solution were added under stirring, and then the flask was immersed in a boiling water bath and refluxed for 5 hours. After completion of the reflux, the inner temperature was returned to room temperature and a binder solution (UDMA, 2G) and a photopolymerization initiator mentioned in Table 1-1 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain medical and/or dental composite resins.

Comparative Examples 2-1 to 2-5

(Preparation of Medical and/or Dental Composite Resin—Inorganic Matter Filling Rate of 85% by Weight)

Using polymerizable silane coupling agents synthesized in Comparative Synthesis Examples 1 to 3 or two types of polymerizable silane coupling agents [KBM-503: 3-(trimethoxysilyl)propyl methacrylate, KBE-503: 3-(triethoxysilyl)propyl methacrylate] available from Shin-Etsu Chemical Co., Ltd., surface modification with OX-50 (manufactured by NIPPON AEROSIL CO., LTD.) and Fuselex (manufactured by TATSUMORI LTD.) and preparation of medical and/or dental composite resins were performed. Specific surface modification method will be mentioned below. Each synthesized silane coupling agent in the amount mentioned in Table 1-2-C was dissolved in 300 mL of ethanol and then the resulting solution was added in a 500 mL recovery flask charged with 15.0 g of OX-50 and 45.0 g of Fuselex. Subsequently, a magnetic stirrer was put in the recovery flask, followed by stirring for 10 minutes stirring and further dispersion using a 28 KHz-150 W ultrasonic disperser for 5 minutes. After completion of the dispersion, 2.4 g of distilled water and 1.2 g of an aqueous 1% by weight phosphoric acid solution were added under stirring, and then the flask was immersed in a boiling water bath and refluxed for 5 hours. After completion of the reflux, the inner temperature was returned to room temperature and a binder solution (UDMA, 2G) and a photopolymerization initiator mentioned in Table 1-2 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain medical and/or dental composite resins.

Comparative Examples 3-1 to 3-3

(Preparation of Pressure-Sensitive Adhesive Pastes)

Using polymerizable silane coupling agents synthesized in Comparative Synthesis Examples 1 to 3, surface modification with OX-50 (manufactured by NIPPON AEROSIL CO., LTD.) and preparation of pressure-sensitive adhesive pastes were performed. Specific surface modification method will be mentioned below. Each synthesized silane coupling agent in the amount mentioned in Table 1-3-C was dissolved in 300 mL of ethanol and then the resulting solution was added in a 500 mL recovery flask charged with 15.0 g of OX-50. Subsequently, a magnetic stirrer was put in the recovery flask, followed by stirring for 10 minutes stirring and further dispersion using a 28 KHz-150 W ultrasonic disperser for 5 minutes. After completion of the dispersion, 0.65 g of distilled water and 0.33 g of an aqueous 1% by weight phosphoric acid solution were added under stirring, and then the flask was immersed in a boiling water bath and refluxed for 5 hours. After completion of the reflux, the inner temperature was returned to room temperature and a binder solution (UDMA, 2G) and a photopolymerization initiator mentioned in Table 1-3 were added under a shading condition. After uniformly stirring, ethanol was distilled off by an evaporator. Subsequently, the solvent was completely removed by Planetary Vacuum mixer ARV-310 manufactured by THINKY CORPORATION under the conditions of 1,000 rpm and 5 KPa for 15 minutes to obtain pressure-sensitive adhesive pastes.

[Test Methods]

Bending Strength Test

Using medical and/or dental composite resins prepared in Examples 1-1-I to 1-7-I, 1-1-II to 1-7-II, 1-1-III to 1-7-III, 2-1-I to 2-7-I, 2-1-II to 2-7-II and 2-1-III to 2-7-III, and Comparative Examples 1-1 to 1-5, 2-1 to 2-5, cured bodies were fabricated in accordance with ISO4049. Using an Instron universal testing machine (Instron 5567, manufactured by Instron Corporation), the bending strength was determined. Photopolymerization was performed by photoirradiation for 30 seconds using Griplight II manufactured by SHOFU INC.

Tensile Strength Test and Elongation Test

Each of pressure-sensitive adhesive pastes prepared in Examples 3-1-I to 3-7-I and 3-1-II to 3-7-II, and Comparative Examples 3-1 to 3-3 was poured into a mold made of SUS304 (24 mm in width, 200 mm in length and 0.2 mm in thickness) coated with a mold releasing agent, followed by pressure welding using a plate made of SUS304 coated with a mold releasing agent and further curing with heating in an oven at 50° C. for 12 hours. In accordance with JIS Z 0237 (pressure-sensitive adhesive tape test method), the tensile strength and the elongation of the resulting specimens were determined. In Example 3-1, the silane coupling agent synthesized in Synthesis Example 1 was used. In Example 3-2, the silane coupling agent synthesized in Synthesis Example 2 was used.

Adhesion Test (Pressure-Sensitive Adhesion Test) to Glass/Metal/Plastic

Each of pressure-sensitive adhesive pastes prepared in Examples 3-1-I to 3-7-I and 3-1-II to 3-7-II, and Comparative Examples 3-1 to 3-3 was interposed between an adherend so as to form the bonding site of 20 mm in width, 50 mm in length and 0.2 mm in thickness, followed by curing with heating in an oven at 50° C. for 12 hours. In accordance with JIS Z 0237 (pressure-sensitive adhesive tape test method), the shear pressure-sensitive adhesive force (unit: $N/cm^2$) of the resulting specimens were determined. The adherends used are (1) a SUS304 plate (20 mm in width, 100 mm in length and 6 mm in thickness) obtained by fusing a silicate glass onto an adherend surface, (2) a metal plate SUS304 (20 mm in width, 100 mm in length and 5 mm in thickness), (3) a plastic plate obtained by pouring a mixed solution of 69.0% by weight of di(methacryloxyethyl)trimethylhexamethylene diurethane, 30.0% by weight of diethylene glycol dimethacrylate and 1.0% by weight of BPO into a mold made of SUS304 (20 mm in width, 100 mm in length and 5 mm in thickness) coated with a mold releasing agent, followed by pressure welding using a plate made of SUS304 coated with a mold releasing agent and further curing with heating in an oven at 50° C. for 12 hours. Using six types of combinations of the above-mentioned adherends (1) to (3), a test was performed. All of adherend surfaces used are polished and smoothened using a waterproof abrasive paper #600.

Polymerization Shrinkage Rate

Each of medical and/or dental composite resins prepared in Examples 1-1-I to 1-7-I, 1-1-II to 1-7-II, 2-1-I to 2-7-I and 2-1-II to 2-7-II, and Comparative Examples 1-1 to 1-5 and 2-1 to 2-5 was filled in a mold made of a stainless steel (10 mm in inner diameter and 2 mm in thickness) and a cover glass was placed on both surfaces thereof, followed by pressure welding and further photoirradiation from both surfaces for each 3 minute using a visible light irradiator (Solidilite V: manufactured by SHOFU INC.) to obtain cured bodies. Using a gas pycnometer (AccuPyc 1303: manufactured by Micromeritics Instrument Corporation), the density before and after curing was measured. In accordance with (Equation 1), the polymerization shrinkage rate was calculated from the resulting measurement values. The density was measured at 25° C.

$$\text{Polymerization shrinkage rate (vol \%)} = (1 - D_{before}/D_{after}) \times 100 \quad \text{(Equation 1)}$$

($D_{before}$: density before curing, $D_{after}$: density after curing)

Color Tone Stability Test of Silane Coupling Agent

Each of 9.0 ml of silane coupling agents synthesized in Synthesis Examples 1-III to 7-III, and Comparative Synthesis Example 1 and two types of polymerizable silane coupling agents [KBM-503: 3-(trimethoxysilyl)propyl methacrylate (C-SC4), KBE-503: 3-(triethoxysilyl)propyl methacrylate (C-SC5)] available from Shin-Etsu Chemical Co., Ltd. was transferred to a 10 mL-volume colorless transparent glass vial and then the Hazen color index was measured. After storing the same sample under a shading condition in a thermostat at 50° C. for a month, the Hazen color index was measured.

Color Tone Stability Test of Medical and/or Dental Composite Resin Cured Bodies Fabricated Using medical and/or dental composite resins thus prepared, cured bodies (circular disk of 15 mm in diameter and 1.0 mm in thickness) were fabricated in accordance with ISO4049, and then the color tone stability of each cured body was determined by a light resistance tester (Atlas SUNTEST CPS+, manufactured by TOYO SEIKI SEISAKU-SHO, LTD.). Photopolymerization was performed by photoirradiation for 30 seconds using Griplight 2 manufactured by SHOFU INC.

[Evaluation Results]

The bending strength test results of medical and/or dental composite resins prepared based on Examples are shown in [Table 2-1] and [Table 2-2]. As is apparent from these results, medical and/or dental composite resins including fine particles prepared using silane coupling agents synthesized (Synthesis Examples 1-I to 7-I, 1-II to 7-II and 1-III to 7-III) by the present invention have obviously high bending strength properties as compared with medical and/or dental composite resins using long chain silane coupling agents having no ethylene oxide group (ether bond) (Comparative Synthesis Examples 1 to 3) or commercially available silane coupling agents. It is particularly apparent that breaking energy properties are significantly improved. In other words, by surface-treating an inorganic filler with the silane coupling agent of the embodiments of the present invention, a medical and/or dental composite resin cured body exhibits toughness, thus imparting high mechanical strength to a medical and/or dental material.

It is assumed that the above results are involved in the fact that the flexibility is imparted by the ethylene oxide group (ether bond). Meanwhile, as mentioned in Comparative Examples, bending strength properties of the medical and/or dental composite resin cured body including the inorganic filler surface-treated with the silane coupling agent having no ethylene oxide group (ether bond) tends to improve as the alkylene chain becomes longer. However, it was absolutely impossible to say that the effect is remarkable as compared with the case where the silane coupling agent of the embodiments of the present invention is used. Subsequently, the tensile strength test and elongation test results of the pressure-sensitive adhesive paste are shown in the evaluation results [Table 2-3]. As is apparent from the results, the elongation significantly increased as the number of the ethylene oxide groups (ether bonds) increased. It is assumed that this is because the flexibility was imparted by the ethylene oxide group (ether bond), like the bending strength test results. In Comparative Examples using a silane coupling agent of the structure having no ethylene oxide group (ether bond), the elongation exhibited a remarkably low value. The reason is considered that carbon-carbon bonding of the alkylene chain is inferior in flexibility as compared with the ethylene oxide group (ether bond). The adhesion (pressure-sensitive adhesion) test results of the pressure-sensitive adhesive paste between various adherends are shown in the evaluation results [Table 2-4]. As is apparent from these results, the pressure-sensitive adhesive paste using the silane coupling agent having an ethylene oxide group (ether bond) of the embodiments of the present invention exhibited satisfactory adhesion (pressure-sensitive adhesion) to glass, metal and plastic. It is considered that this factor is also attributed to polarity of the ethylene oxide group (ether bond). Finally, the polymerization shrinkage rate test results are shown in the evaluation results [Table 2-5][Table 2-6]. As is apparent from these test results, the medical and/or dental composite resins including fine particles prepared using silane coupling agents synthesized by the present invention (Synthesis Examples 1-I to 7-I, 1-II to 7-II and 1-III to 7-III) exhibited significant improvement in polymerization shrinkage as compared with the medical and/or dental composite resins using long chain silane coupling agents having no ethylene oxide group (ether bond) (Comparative Synthesis Examples 1 to 3). The reason is considered that the ethylene oxide group (ether bond) is extended so as to release shrinkage stress during polymerization. This high adhesion (pressure-sensitive adhesion) has a high application value not only in a medical and/or dental material, but also in bonding of electronic component material substrates including smartphones and bonding to automotive materials in the general industrial field. As is apparent from the above evaluation results, the silane coupling agent having an ether bond such as an ethylene oxide group in the present invention made it possible to provide a medical and/or dental curable composition having high mechanical strength that could not been achieved by the prior art, and applications thereof in the general industrial field such as for bonding of electronic component material substrates including smartphones and automotive materials.

It is assumed that the above results are also involved in the fact that the long chain alkylene group and a plurality of urethane groups are imparted. As is apparent from the bending strength test results, the silane coupling agent having a long chain alkylene group and a plurality of urethane groups of the embodiments of the present invention made it possible to provide a medical and/or dental curable composition having high mechanical strength that could not been achieved by the prior art, and applications thereof in the general industrial field such as for bonding of electronic component material substrates including smartphones and automotive materials. Subsequently, the measurement results of the Hazen color index determined by a color tone stability test are shown in Table 2-7. As is apparent from these measurement results, there was no large difference in Hazen color index between the polymerizable silane coupling agents including no platinum complex synthesized in Synthesis Examples 1 to 7 and two types of polymerizable silane coupling agents [3-(trimethoxysilyl)propyl methacrylate, 3-(triethoxysilyl)propyl methacrylate] available from Shin-Etsu Chemical Co., Ltd., immediately after synthesis and purchasing, and after storing under a shading condition at 50° C. for a month. Meanwhile, there was a large difference in Hazen color index between the polymerizable silane coupling agent including a platinum complex synthesized in Comparative Synthesis Example 1, immediately after synthesis, and after storing under a shading condition at 50° C. for a month. It is considered that this large change in color tone is attributed to the remaining platinum complex. Subsequently, the measurement results relating to the color tone stability of the cured body are shown in Table 2-8. As is apparent from these measurement results, there was no large change in color tone of the medical and/or dental composite resin cured bodies including an inorganic filler surface-modified with the polymerizable silane coupling agents including no platinum complex synthesized in Synthesis Examples 1 to 7 and two types of polymerizable silane coupling agents [3-(trimethoxysilyl)propyl methacrylate, 3-(triethoxysilyl)propyl methacrylate] available from Shin-Etsu Chemical Co., Ltd. Meanwhile, there arose a large difference in color tone of the medical and/or dental composite resin cured body including an inorganic filler surface-modified with the polymerizable silane coupling agents including a platinum complex synthesized in Comparative Synthesis Example 1, leading to remarkable yellowing. As is apparent from these test results, it is revolutionary in that no discoloration due to aesthetically important noble metal is not observed in the medical and/or dental curable composition. Since no noble metal as a hydrosilylation catalyst is used during synthesis, it became possible to decrease manufacturing costs.

Abbreviations in tables have the following meanings.
SC: Silane coupling agent
C-SC: Comparative-silane coupling agent
C-SC4: 3-(Trimethoxysilyl)propyl methacrylate
C-SC5: 3-(Triethoxysilyl)propyl methacrylate
UDMA: Di(methacryloxyethyl)trimethylhexamethylene diurethane
2G: Diethylene glycol dimethacrylate In the preparation of medical and/or dental composite resins (Tables 1-1 to 1-2), diphenyl(2,4,6-trimethylbenzoyl) phosphine oxide was used as the initiator. In the preparation of pressure-sensitive adhesive pastes (Table 1-3), BPO (benzoyl peroxide) was used as the initiator.

(Preparation of Medical and/or Dental Composite Resins—Inorganic Matter Filling Rate of 70% by Weight)

TABLE 1-1-I

Unit: g

| | Example 1-1-I | Example 1-2-I | Example 1-3-I | Example 1-4-I | Example 1-5-I | Example 1-6-I | Example 1-7-I |
|---|---|---|---|---|---|---|---|
| SC-I | 9.45 | — | — | — | — | — | — |
| SC2-I | — | 10.23 | — | — | — | — | — |
| SC3-I | — | — | 11.01 | — | — | — | — |
| SC4-I | — | — | — | 8.46 | — | — | — |
| SC5-I | — | — | — | — | 7.96 | — | — |
| SC6-I | — | — | — | — | — | 7.47 | — |
| SC7-I | — | — | — | — | — | — | 8.25 |
| OX-50 | 15.0 | 15.0 | 15.0 | 15.0 | 15.0 | 15.0 | 15.0 |
| Fuselex | 40.0 | 40.0 | 40.0 | 40.0 | 40.0 | 40.0 | 40.0 |
| UDMA | 16.5 | 16.5 | 16.5 | 16.5 | 16.5 | 16.5 | 16.5 |
| 2G | 7.1 | 7.1 | 7.1 | 7.1 | 7.1 | 7.1 | 7.1 |
| Initiator | 0.24 | 0.24 | 0.24 | 0.24 | 0.24 | 0.24 | 0.24 |

TABLE 1-1-II

Unit: g

| | Example 1-1-II | Example 1-2-II | Example 1-3-II | Example 1-4-II | Example 1-5-II | Example 1-6-II | Example 1-7-II |
|---|---|---|---|---|---|---|---|
| SC1-II | 9.82 | — | — | — | — | — | — |
| SC2-II | — | 10.60 | — | — | — | — | — |
| SC3-II | — | — | 10.82 | — | — | — | — |
| SC4-II | — | — | — | 9.04 | — | — | — |
| SC5-II | — | — | — | — | 9.82 | — | — |
| SC6-II | — | — | — | — | — | 10.53 | — |
| SC7-II | — | — | — | — | — | — | 13.48 |
| OX-50 | 15.0 | 15.0 | 15.0 | 15.0 | 15.0 | 15.0 | 15.0 |
| Fuselex | 40.0 | 40.0 | 40.0 | 40.0 | 40.0 | 40.0 | 40.0 |
| UDMA | 16.5 | 16.5 | 16.5 | 16.5 | 16.5 | 16.5 | 16.5 |
| 2G | 7.1 | 7.1 | 7.1 | 7.1 | 7.1 | 7.1 | 7.1 |
| Initiator | 0.24 | 0.24 | 0.24 | 0.24 | 0.24 | 0.24 | 0.24 |

TABLE 1-1-III

Unit: g

| | Example 1-1-III | Example 1-2-III | Example 1-3-III | Example 1-4-III | Example 1-5-III | Example 1-6-III | Example 1-7-III |
|---|---|---|---|---|---|---|---|
| SC1-III | 9.47 | — | — | — | — | — | — |
| SC2-III | — | 10.50 | — | — | — | — | — |
| SC3-III | — | — | 10.71 | — | — | — | — |
| SC4-III | — | — | — | 8.97 | — | — | — |
| SCS-III | — | — | — | — | 9.75 | — | — |
| SC6-III | — | — | — | — | — | 10.46 | — |
| SC7-III | — | — | — | — | — | — | 13.20 |
| OX-50 | 15.0 | 15.0 | 15.0 | 15.0 | 15.0 | 15.0 | 15.0 |
| Fuselex | 40.0 | 40.0 | 40.0 | 40.0 | 40.0 | 40.0 | 40.0 |
| UDMA | 16.5 | 16.5 | 16.5 | 16.5 | 16.5 | 16.5 | 16.5 |
| 2G | 7.1 | 7.1 | 7.1 | 7.1 | 7.1 | 7.1 | 7.1 |
| Initiator | 0.24 | 0.24 | 0.24 | 0.24 | 0.24 | 0.24 | 0.24 |

TABLE 1-1-C

Unit: g

| | Comparative Example 1-1 | Comparative Example 1-2 | Comparative Example 1-3 | Comparative Example 1-4 | Comparative Example 1-5 |
|---|---|---|---|---|---|
| C-SC1 | 8.67 | — | — | — | — |
| C-SC2 | — | 10.16 | — | — | — |
| C-SC3 | — | — | 10.91 | — | — |

TABLE 1-1-C-continued

|  | Comparative Example 1-1 | Comparative Example 1-2 | Comparative Example 1-3 | Comparative Example 1-4 | Unit: g Comparative Example 1-5 |
|---|---|---|---|---|---|
| C-SC4 | — | — | — | 4.40 | — |
| C-SC5 | — | — | — | — | 5.14 |
| OX-50 | 15.0 | 15.0 | 15.0 | 15.0 | 15.0 |
| Fuselex | 40.0 | 40.0 | 40.0 | 40.0 | 40.0 |
| UDMA | 16.5 | 16.5 | 16.5 | 16.5 | 16.5 |
| 2G | 7.1 | 7.1 | 7.1 | 7.1 | 7.1 |
| initiator | 0.24 | 0.24 | 0.24 | 0.24 | 0.24 |

(Preparation of Medical and/or Dental Composite Resin—Inorganic Matter Filling Rate of 85% by Weight)

TABLE 1-2-I

|  | Example 2-1-I | Example 2-2-I | Example 2-3-I | Example 2-4-I | Example 2-5-I | Example 2-6-I | Unit: g Example 2-7-I |
|---|---|---|---|---|---|---|---|
| SC1-I | 9.45 | — | — | — | — | — | — |
| SC2-I | — | 10.23 | — | — | — | — | — |
| SC3-I | — | — | 11.01 | — | — | — | — |
| SC4-I | — | — | — | 8.46 | — | — | — |
| SC5-I | — | — | — | — | 7.96 | — | — |
| SC6-I | — | — | — | — | — | 7.47 | — |
| SC7-I | — | — | — | — | — | — | 8.25 |
| OX-50 | 15.0 | 15.0 | 15.0 | 15.0 | 15.0 | 15.0 | 15.0 |
| Fuselex | 40.0 | 40.0 | 40.0 | 40.0 | 40.0 | 40.0 | 40.0 |
| UDMA | 6.8 | 6.8 | 6.8 | 6.8 | 6.8 | 6.8 | 6.8 |
| 2G | 2.9 | 2.9 | 2.9 | 2.9 | 2.9 | 2.9 | 2.9 |
| Initiator | 0.1 | 0.1 | 0.1 | 0.1 | 0.1 | 0.1 | 0.1 |

TABLE 1-2-II

|  | Example 2-1-II | Example 2-2-II | Example 2-3-II | Example 2-4-II | Example 2-5-II | Example 2-6-II | Unit: g Example 2-7-II |
|---|---|---|---|---|---|---|---|
| SC1-II | 9.82 | — | — | — | — | — | — |
| SC2-II | — | 10.60 | — | — | — | — | — |
| SC3-II | — | — | 10.82 | — | — | — | — |
| SC4-II | — | — | — | 9.04 | — | — | — |
| SC5-II | — | — | — | — | 9.82 | — | — |
| SC6-II | — | — | — | — | — | 10.53 | — |
| SC7-II | — | — | — | — | — | — | 13.48 |
| OX-50 | 15.0 | 15.0 | 15.0 | 15.0 | 15.0 | 15.0 | 15.0 |
| Fuselex | 40.0 | 40.0 | 40.0 | 40.0 | 40.0 | 40.0 | 40.0 |
| UDMA | 6.8 | 6.8 | 6.8 | 6.8 | 6.8 | 6.8 | 6.8 |
| 2G | 2.9 | 2.9 | 2.9 | 2.9 | 2.9 | 2.9 | 2.9 |
| Initiator | 0.1 | 0.1 | 0.1 | 0.1 | 0.1 | 0.1 | 0.1 |

TABLE 1-2-III

|  | Example 2-1-III | Example 2-2-III | Example 2-3-III | Example 2-4-III | Example 2-5-III | Example 2-6-III | Unit: g Example 2-7-III |
|---|---|---|---|---|---|---|---|
| SC1-III | 9.47 | — | — | — | — | — | — |
| SC2-III | — | 10.50 | — | — | — | — | — |
| SC3-III | — | — | 10.71 | — | — | — | — |
| SC4-III | — | — | — | 8.97 | — | — | — |
| SC5-III | — | — | — | — | 9.75 | — | — |
| SC6-III | — | — | — | — | — | 10.46 | — |
| SC7-III | — | — | — | — | — | — | 13.20 |
| OX-50 | 15.0 | 15.0 | 15.0 | 15.0 | 15.0 | 15.0 | 15.0 |
| Fuselex | 40.0 | 40.0 | 40.0 | 40.0 | 40.0 | 40.0 | 40.0 |
| UDMA | 6.8 | 6.8 | 6.8 | 6.8 | 6.8 | 6.8 | 6.8 |
| 2G | 2.9 | 2.9 | 2.9 | 2.9 | 2.9 | 2.9 | 2.9 |
| Initiator | 0.1 | 0.1 | 0.1 | 0.1 | 0.1 | 0.1 | 0.1 |

TABLE 1-2-C

Filling rate of 85% by weight

|  | Comparative Example 2-1 | Comparative Example 2-2 | Comparative Example 2-3 | Comparative Example 2-4 | Unit: g Comparative Example 2-5 |
|---|---|---|---|---|---|
| C-SC1 | 8.67 | — | — | — | — |
| C-SC2 | — | 10.16 | — | — | — |
| C-SC3 | — | — | 10.91 | — | — |
| C-SC4 | — | — | — | 4.40 | — |
| C-SC5 | — | — | — | — | 5.14 |
| OX-50 | 15.0 | 15.0 | 15.0 | 15.0 | 15.0 |
| Fuselex | 40.0 | 40.0 | 40.0 | 40.0 | 40.0 |
| UDMA | 6.8 | 6.8 | 6.8 | 6.8 | 6.8 |
| 2G | 2.9 | 2.9 | 2.9 | 2.9 | 2.9 |
| Initiator | 0.1 | 0.1 | 0.1 | 0.1 | 0.1 |

(Preparation of Pressure-Sensitive Adhesive Paste)

TABLE 1-3-I

|  | Example 3-1-I | Example 3-2-I | Example 3-3-I | Example 3-4-I | Example 3-5-I | Example 3-6-I | Unit: g Example 3-7-I |
|---|---|---|---|---|---|---|---|
| SC1-I | 2.58 | — | — | — | — | — | — |
| SC2-I | — | 2.79 | — | — | — | — | — |
| SC3-I | — | — | 3.00 | — | — | — | — |
| SC4-I | — | — | — | 2.31 | — | — | — |
| SC5-I | — | — | — | — | 2.17 | — | — |
| SC6-I | — | — | — | — | — | 2.04 | — |
| SC7-I | — | — | — | — | — | — | 2.25 |
| OX-50 | 15.0 | 15.0 | 15.0 | 15.0 | 15.0 | 15.0 | 15.0 |
| UDMA | 16.5 | 16.5 | 16.5 | 16.5 | 16.5 | 16.5 | 16.5 |
| 2G | 7.1 | 7.1 | 7.1 | 7.1 | 7.1 | 7.1 | 7.1 |
| Initiator | 0.24 | 0.24 | 0.24 | 0.24 | 0.24 | 0.24 | 0.24 |

TABLE 1-3-II

|  | Example 3-1-II | Example 3-2-II | Example 3-3-II | Example 3-4-II | Example 3-5-II | Example 3-6-II | Unit: g Example 3-7-II |
|---|---|---|---|---|---|---|---|
| SC1-II | 2.68 | — | — | — | — | — | — |
| SC2-II | — | 2.89 | — | — | — | — | — |
| SC3-II | — | — | 2.95 | — | — | — | — |
| SC4-II | — | — | — | 2.47 | — | — | — |
| SC5-II | — | — | — | — | 2.68 | — | — |
| SC6-II | — | — | — | — | — | 2.87 | — |
| SC7-II | — | — | — | — | — | — | 3.68 |
| OX-50 | 15.0 | 15.0 | 15.0 | 15.0 | 15.0 | 15.0 | 15.0 |
| UDMA | 16.5 | 16.5 | 16.5 | 16.5 | 16.5 | 16.5 | 16.5 |
| 2G | 7.1 | 7.1 | 7.1 | 7.1 | 7.1 | 7.1 | 7.1 |
| Initiator | 0.24 | 0.24 | 0.24 | 0.24 | 0.24 | 0.24 | 0.24 |

TABLE 1-3-C

|  | Comparative Example 3-1 | Comparative Example 3-2 | Unit: g Comparative Example 3-3 |
|---|---|---|---|
| C-SC1 | 2.37 | — | — |
| C-SC2 | — | 2.77 | — |
| C-SC3 | — | — | 2.98 |
| OX-50 | 15.0 | 15.0 | 15.0 |
| UDMA | 16.5 | 16.5 | 16.5 |

TABLE 1-3-C-continued

|  | Comparative Example 3-1 | Comparative Example 3-2 | Unit: g Comparative Example 3-3 |
|---|---|---|---|
| 2G | 7.1 | 7.1 | 7.1 |
| Initiator | 0.24 | 0.24 | 0.24 |

Bending Strength Test (Inorganic Matter Filling Rate of 70% by Weight)

TABLE 2-1

| | | Bending test results (bending stress: MPa, breaking energy: Kgf-mm) | | | | | | |
|---|---|---|---|---|---|---|---|---|
| | | Example 1-1-I | Example 1-2-I | Example 1-3-I | Example 1-4-I | Example 1-5-I | Example 1-6-I | Example 1-7-I |
| 70% by weight | MPa Kgf-mm | 145 2.51 | 147 2.72 | 151 2.91 | 146 2.35 | 145 2.30 | 145 2.31 | 149 2.70 |
| | | Example 1-1-II | Example 1-2-II | Example 1-3-II | Example 1-4-II | Example 1-5-II | Example 1-6-II | Example 1-7-II |
| 70% by weight | MPa Kgf-mm | 146 2.98 | 147 3.05 | 152 2.93 | 148 2.70 | 146 3.00 | 151 2.62 | 150 3.10 |
| | | Example 1-1-III | Example 1-2-III | Example 1-3-III | Example 1-4-III | Example 1-5-III | Example 1-6-III | Example 1-7-III |
| 70% by weight | MPa Kgf-mm | 135 2.51 | 137 2.72 | 141 2.91 | 136 2.35 | 135 2.30 | 135 2.31 | 139 2.70 |
| | | Comparative Example 1-1 | Comparative Example 1-2 | Comparative Example 1-3 | Comparative Example 1-4 | Comparative Example 1-5 | | |
| 70% by weight | MPa Kgf-mm | 129 1.82 | 130 1.93 | 132 1.95 | 105 1.23 | 106 1.25 | | |

Bending Strength Test (Inorganic Matter Filling Rate of 85% by Weight)

TABLE 2-2

| | | Bending test results (bending stress: MPa, breaking energy: Kgf-mm) | | | | | | |
|---|---|---|---|---|---|---|---|---|
| | | Example 2-1-I | Example 2-2-I | Example 2-3-I | Example 2-4-I | Example 2-5-I | Example 2-6-I | Example 2-7-I |
| 85% by weight | MPa Kgf-mm | 161 2.81 | 160 3.01 | 166 3.22 | 160 2.59 | 159 2.51 | 158 2.54 | 163 3.10 |
| | | Example 2-1-II | Example 2-2-II | Example 2-3-II | Example 2-4-II | Example 2-5-II | Example 2-6-II | Example 2-7-II |
| 85% by weight | MPa Kgf-mm | 165 3.20 | 161 3.35 | 165 3.22 | 160 3.05 | 158 3.21 | 165 3.10 | 162 3.50 |
| | | Example 2-1-III | Example 2-2-III | Example 2-3-III | Example 2-4-III | Example 2-5-III | Example 2-6-III | Example 2-7-III |
| 85% by weight | MPa Kgf-mm | 151 2.81 | 150 3.01 | 156 3.22 | 150 2.59 | 149 2.51 | 148 2.54 | 153 3.10 |
| | | Comparative Example 2-1 | Comparative Example 2-2 | Comparative Example 2-3 | Comparative Example 2-4 | Comparative Example 2-5 | | |
| 85% by weight | MPa Kgf-mm | 139 1.99 | 144 2.01 | 142 2.03 | 115 1.35 | 113 1.31 | | |

Tensile Strength Test and Elongation Test

TABLE 2-3

|  | Example 3-1-I | Example 3-2-I | Example 3-3-I | Example 3-4-I | Example 3-5-I | Example 3-6-I | Example 3-7-I |
|---|---|---|---|---|---|---|---|
| Breaking strength: MPa | 22.5 | 25.7 | 33.7 | 22.1 | 21.8 | 21.5 | 25.1 |
| Elongation: % | 35.6 | 38.7 | 50.3 | 35.3 | 35.1 | 35.0 | 38.6 |

|  | Example 3-1-II | Example 3-2-II | Example 3-3-II | Example 3-4-II | Example 3-5-II | Example 3-6-II | Example 3-7-II |
|---|---|---|---|---|---|---|---|
| Breaking strength: MPa | 27.1 | 28.0 | 27.0 | 25.5 | 27.8 | 26.2 | 28.3 |
| Elongation: % | 35.7 | 28.9 | 35.5 | 35.2 | 28.3 | 34.9 | 55.2 |

|  | Comparative Example 3-1 | Comparative Example 3-2 | Comparative Example 3-3 |
|---|---|---|---|
| Breaking strength: MPa | 19.2 | 20.1 | 20.3 |
| Elongation: % | 8.2 | 8.5 | 8.4 |

Test of Adhesion (Test of Pressure-Sensitive Adhesion) to Glass/Metal/Plastic

TABLE 2-4

Adhesion test (pressure-sensitive adhesion test) N/cm²

| Adherend | Example 3-1-I | Example 3-2-I | Example 3-3-I | Example 3-4-I | Example 3-5-I | Example 3-6-I | Example 3-7-I |
|---|---|---|---|---|---|---|---|
| (1) × (1) | 75.3 | 99.2 | 105 | 75.6 | 75.1 | 75.0 | 99.5 |
| (1) × (2) | 75.1 | 100 | 106 | 75.2 | 75.0 | 75.0 | 99.9 |
| (1) × (3) | 74.9 | 99.5 | 104 | 75.5 | 75.2 | 75.3 | 100 |
| (2) × (2) | 75.2 | 101 | 107 | 75.5 | 75.1 | 75.1 | 101 |
| (2) × (3) | 75.3 | 99.9 | 105 | 75.3 | 75.3 | 76.1 | 100 |
| (3) × (3) | 75.3 | 102 | 104 | 75.7 | 75.4 | 76.2 | 102 |

| Adherend | Example 3-1-II | Example 3-2-II | Example 3-3-II | Example 3-4-II | Example 3-5-II | Example 3-6-II | Example 3-7-II |
|---|---|---|---|---|---|---|---|
| (1) × (1) | 75.2 | 100 | 75.3 | 75.5 | 99.5 | 75.0 | 105 |
| (1) × (2) | 75.1 | 102 | 75.5 | 75.1 | 98.3 | 75.2 | 107 |
| (1) × (3) | 76.1 | 103 | 75.9 | 75.3 | 99.7 | 75.9 | 104 |
| (2) × (2) | 75.0 | 101 | 75.1 | 75.6 | 100 | 75.2 | 106 |
| (2) × (3) | 75.3 | 100 | 75.7 | 75.7 | 99.9 | 76.3 | 108 |
| (3) × (3) | 75.1 | 101 | 75.1 | 75.4 | 101 | 76.5 | 103 |

| Adherend | Comparative Example 3-1 | Comparative Example 3-2 | Comparative Example 3-3 |
|---|---|---|---|
| (1) × (1) | 5.1 | 5.3 | 5.3 |
| (1) × (2) | 5.0 | 5.2 | 5.3 |
| (1) × (3) | 7.8 | 7.5 | 7.7 |
| (2) × (2) | 5.2 | 5.1 | 5.1 |
| (2) × (3) | 7.9 | 7.6 | 7.5 |
| (3) × (3) | 9.9 | 10.1 | 11.3 |

(1) SUS304 plate in which silicate glass is fused to adherend surface (2) Metal plate SUS304

(3) Plastic plate

Polymerization Shrinkage Rate

[2-5]
Polymerization shrinkage rate (%)

| | Example 1-1-I | Example 1-2-I | Example 1-3-I | Example 1-4-I | Example 1-5-I | Example 1-6-I | Example 1-7-I |
|---|---|---|---|---|---|---|---|
| Filling rate 70% | 3.5 | 3.1 | 2.8 | 3.4 | 3.4 | 3.5 | 3.1 |

| | Example 1-1-II | Example 1-2-II | Example 1-3-II | Example 1-4-II | Example 1-5-II | Example 1-6-II | Example 1-7-II |
|---|---|---|---|---|---|---|---|
| Filling rate 70% | 3.4 | 2.9 | 3.3 | 3.4 | 3.1 | 3.5 | 2.7 |

| | Comparative Example 1-1 | Comparative Example 1-2 | Comparative Example 1-3 |
|---|---|---|---|
| Filling rate 70% | 5.5 | 5.3 | 5.1 |

TABLE 2-6

Polymerization shrinkage rate(%)

| | Example 2-1-I | Example 2-2-I | Example 2-3-I | Example 2-4-I | Example 2-5-I | Example 2-6-I | Example 2-7-I |
|---|---|---|---|---|---|---|---|
| Filling rate 85% | 1.5 | 1.3 | 1.1 | 1.5 | 1.4 | 1.5 | 1.4 |

| | Example 2-1-II | Example 2-2-II | Example 2-3-II | Example 2-4-II | Example 2-5-II | Example 2-6-II | Example 2-7-II |
|---|---|---|---|---|---|---|---|
| Filling rate 85% | 1.4 | 1.3 | 1.3 | 1.5 | 1.5 | 1.7 | 1.2 |

| | Comparative Example 1-1 | Comparative Example 1-2 | Comparative Example 1-3 |
|---|---|---|---|
| Filling rate 85% | 3.5 | 3.3 | 3.2 |

Color Tone Stability Test of Silane Coupling Agent

TABLE 2-7

| Hazen Color Index | | | | | | | |
|---|---|---|---|---|---|---|---|
| | SC1-III | SC2-III | SC3-III | SC4-III | SC5-III | SC6-III | SC7-III |
| Immediately after synthesis | 15 | 15 | 15 | 15 | 15 | 15 | 15 |
| After 1 month at 50° C. | 20 | 20 | 20 | 20 | 20 | 20 | 20 |

TABLE 2-7-continued

| Hazen Color Index | | | |
|---|---|---|---|
| | C-SC1 | C-SC4 | C-SC5 |
| Immediately after synthesis | 20 | 12 | 12 |
| After 1 month at 50° C. | 300 | 18 | 19 |

Color Tone Stability Test of Medical and/or Dental Composite Resin Cured Body Fabricated

TABLE 2-8

| Color tone stability (L/a*/b*) of cured body | | | | | | | |
|---|---|---|---|---|---|---|---|
| | Example 1-1-III | Example 1-2-III | Example 1-3-III | Example 1-4-III | Example 1-5-III | Example 1-6-III | Example 1-7-III |
| Control | 80.0/−2.0/5.0 | 80.0/−2.0/5.0 | 80.0/−2.0/5.0 | 80.0/−2.0/5.0 | 80.0/−2.0/5.0 | 80.0/−2.0/5.0 | 80.0/−2.1/5.0 |
| In water | 79.9/−2.1/5.1 | 79.9/−2.0/5.1 | 79.9/−2.1/5.0 | 79.9/−2.0/5.1 | 79.9/−2.1/5.1 | 79.9/−2.1/5.0 | 79.9/−2.0/5.1 |

TABLE 2-8-continued

| Color tone stability (L/a*/b*) of cured body | | | | | | | |
|---|---|---|---|---|---|---|---|
| After photoirradiation | 79.0/−3.0/5.3 | 79.1/−3.0/5.2 | 79.2/−3.0/5.2 | 79.0/−3.0/5.3 | 79.1/−3.0/5.2 | 79.2/−3.0/5.3 | 79.1/−3.0/5.2 |

| | Comparative Example 1-1 | Comparative Example 1-4 | Comparative Example 1-5 |
|---|---|---|---|
| Control | 80.0/−2.0/5.0 | 80.0/−2.0/5.0 | 80.0/−2.0/5.0 |
| In water | 75.9/−2.9/5.1 | 79.9/−2.1/5.0 | 80.0/−2.0/5.1 |
| After photoirradiation | 72.1/−3.9/5.9 | 79.0/−2.9/5.3 | 79.2/−3.0/5.2 |

Regarding the silane coupling agent that is currently being used, not limited to the medical and/or dental field and the general industrial field, compounds having a long alkylene chain are used to improve various physical properties. However, the alkylene chain is nonpolar and has properties that are inferior in elasticity. Therefore, as compared with a low molecular weight silane coupling agent (number of alkylene chains: 3, etc.), although the effect of an improvement in various physical properties was recognized, the silane coupling agent was inferior in adhesion, flexibility and pressure-sensitive adhesion. The silane coupling agent of the present invention has solved those problems, so that it is possible to say that its industrial applicability is great.

What is claimed is:

1. A silane coupling agent having:
   a polymerizable group,
   a reactive silyl group, and
   a spacer group connecting the polymerizable group and the reactive silyl group,
   wherein the spacer group is the following spacer group I:
   Spacer group I:

—Z¹—NH—C(O)OR³—  Formula (I)

wherein, $Z^1$ is a C2-C30 linear or branched saturated aliphatic hydrocarbon group, and has at least one or more of —CH₂—CH₂—O—, —O—CH(CH₃)—CH₂— and —O—CH₂—CH(CH₃)— groups, and $R^3$ is a C7-C30 linear or branched alkylene group, and may have one or more of —S—, —NH—, —NR″— wherein R″ represents an alkylene group, —CH₂—C₆H₄— wherein C₆H₄ represents a phenylene group, —C(O)—O—, —O—, —CH₂—CH₂—O—, —O—CH(CH₃)—CH₂— and —O—CH₂—CH(CH₃)— groups.

2. The silane coupling agent according to claim 1, which is represented by the following formula:

$(A-B)_a\text{-Q-Si}—(OR^1)_nR^2_{(3-n)}$ wherein
   $(A-B)_a$- represents a polymerizable group, A represents a H₂C=CH—, H₂C=C(CH₃)— or H₂C=CH—C₆H₄— group wherein C₆H₄ represents a phenylene group, B represents —C(O)—O—, —C(O)—S—, —C(O)—NH—, —NH—C(O)—NH—, —NH—C(O)—S— or —NH—C(O)—O—, a represents an integer of 1 to 6,
   —Si—(OR¹)ₙR²₍₃₋ₙ₎ represents a reactive silyl group, $R^1$ represents a C1-C6 linear or branched alkyl group, $R^2$ represents a C1-C16 linear or branched alkyl group, a phenyl group or a halogen atom and n represents an integer of 0 to 3, and when n is 0, at least one or more halogen atoms are bonded to Si, and
   -Q- represents the spacer group.

3. The silane coupling agent according to claim 1, which is synthesized using a compound having any one of the following structures (2-(2-isocyanatoethoxy)ethyl methacrylate or 2-(2-isocyanatoethoxy)ethyl acrylate):

CH₂=C(CH₃)—C(O)—O—CH₂—CH₂—O—CH₂—CH₂—NCO

CH₂=CH—C(O)—O—CH₂—CH₂—O—CH₂—CH₂—NCO.

4. An inorganic filler which is surface-treated with the silane coupling agent according to claim 1.

5. A medical and/or dental curable composition comprising the inorganic filler according to claim 4, a radical polymerizable monomer other than the silane coupling agent, and either a polymerization initiator or a polymerization accelerator.

* * * * *